United States Patent [19]
Ramasamy et al.

[11] Patent Number: 5,969,135
[45] Date of Patent: Oct. 19, 1999

[54] OLIGONUCLEOTIDE ANALOGS WITH AN AMINO ACID OR A MODIFIED AMINO ALCOHOL RESIDUE

[75] Inventors: Kandasamy Ramasamy, Laguna Hills; Wilfried E. Seifert, La Jolla, both of Calif.

[73] Assignee: ICN Pharmaceuticals, Inc., Costa Mesa, Calif.

[21] Appl. No.: 08/551,947

[22] Filed: Nov. 2, 1995

[51] Int. Cl.$^6$ .............................. C07D 473/00; C07F 9/02
[52] U.S. Cl. ........................ 544/264; 544/265; 544/243
[58] Field of Search .................................. 544/264, 265, 544/243

[56] References Cited

U.S. PATENT DOCUMENTS

| | | | |
|---|---|---|---|
| 4,774,325 | 9/1988 | Casadio et al. | 544/265 |
| 5,175,288 | 12/1992 | Grinter et al. | 544/230 |
| 5,208,221 | 5/1993 | Kim et al. | 514/81 |
| 5,216,141 | 6/1993 | Benner | 536/27.13 |
| 5,284,837 | 2/1994 | Lindberg et al. | 514/81 |
| 5,298,621 | 3/1994 | Marzi et al. | 544/265 |
| 5,656,744 | 8/1997 | Arnold, Jr. et al. | 536/25.3 |

FOREIGN PATENT DOCUMENTS

| | | |
|---|---|---|
| 0152316 | 1/1985 | European Pat. Off. . |
| 95/23160 | 8/1995 | WIPO . |

*Primary Examiner*—Mukund J. Shah
*Assistant Examiner*—Tamthom T. Ngo
*Attorney, Agent, or Firm*—Crockett & Fish; Robert D. Fish

[57] ABSTRACT

The present invention provides various novel oligonucleotide analogs having one or more properties that make the subject compounds superior to conventional oligonucleotides for use in procedures employing oligonucleotides. The compounds of the invention are oligonucleotide analogs in which the furanose ring of a naturally occurring nucleic acid is replaced with an amino acid or a modified amino alcohol residue. Some embodiments of the novel compounds of the invention are particularly useful for the antisense control of gene expression. The compounds of the invention may also be used as nucleic acid hybridization probes or as primers. Another aspect of the invention is to provide monomeric precursors of the oligonucleotide analogs of the invention. These monomeric precursors may be used to synthesize the subject polynucleotide analogs. Another aspect of the invention is to provide formulations of the subject polynucleotide analogs that are designed for the treatment or prevention of disease conditions. Yet another aspect of the invention is to provide methods for treating or preventing diseases, particularly viral infections and cell growth disorders. The subject disease treatment methods comprise the step of administering an effective amount of the subject polynucleotide analogs for use as antisense inhibitors.

9 Claims, 33 Drawing Sheets a) ICH2CONMe2 and Zn, b) H2O/NaHCO3, c) Ac2O, d) Ph3P, CCl4, e) NH3, f) NaOH/H2O, g) BrCH2B, where B is protected nucleobase, h) Fmoc-Cl, i) TBDMSi-Cl.

a) NaCN, b) NH4OH, c) Ac2O, d) Ph3P, CCl4, e) CH3NO2, f) NaOH/H2O, g) TBDMSi-Cl and Pd/C, h) BrCH2B, where B is protected nucleobase, i) Fmoc-Cl.

a) $CH_2(COOET)_2$, b) $H_2O/NaHCO_3$, c) Heating,
d) $BrCH_2CH_2B$, where B is protected nucleobase,
e) $NH_4OH$, f) TBDMSi-Cl, g) $Ph_3P/CCl_4$, h) $NH_3$, i) Fmoc-Cl.

OLIGONUCLEOTIDE ANALOGS WITH AN AMINO ACID OR A MODIFIED AMINO ALCOHOL RESIDUE

FIELD OF THE INVENTION

The invention is in the field of polynucleotide analogs lacking furanose rings.

BACKGROUND OF THE INVENTION

Oligonucleotides that bind sequence specifically to complementary nucleic acids (i.e. sense strand) by hydrogen bonding so as to inhibit gene expression are commonly referred to as antisense oligonucleotides. These synthetic oligonucleotides bind to target (MRNA) and thereby inhibit translation of the messenger RNA. This antisense principle (Uhlmann, E. et al., *Chem. Reviews*, 1990, 90, 543–584; and Stein, C. A. et al., *Cancer Res.*, 1988, 48, 2659–2688) is used in nature to regulate gene expression. This antisense principle has been used in the laboratory not only to inhibit but also to activate gene expression. Zamecnik and Stephenson were the first to propose, in 1978, the use of synthetic oligonucleotides for therapeutic purposes (Stephenson, M. L.; and Zamecnik, P. C., *Proc. Natl. Acad. Sci. USA*, 1978, 75, 280 and 285). The specific inhibition of antisense polynucleotide is based on the specific Watson-Crick base pairing between the heterocyclic bases of the antisense oligonucleotide and of viral nucleic acid. The process of binding of the oligonucleotides to a complementary nucleic acid is called hybridization. An oligomer having a base sequence complementary to that of an mRNA which encodes protein necessary for the progress of the disease is of particular interest. By hybridizing specifically to the mRNA, the synthesis of proteins encoded by the mRNA may be disturbed.

The preparation of unmodified oligonucleotides, i.e., oligonucleotides having a DNA structure, has been the center of interest for many research groups in the past decade. The synthesis via phosphoramidites according to Caruthers (McBride, L. J.; and Caruthers, M. H., *Tetrahedron Letts.*, 1983, 24, 245), originally introduced by Letsinger (Letsinger, R. L.; and Lunsford, W. B., *J. Amer. Chem. Soc.*, 1976, 98, 3655) as the phosphite triester method, is currently the most efficient method for the preparation phosphodiester oligonucleotides. When normal, i.e., unmodified, oligonucleotides are used as antisense oligonucleotides, the problems of instability to nucleases and insufficient membrane penetration have arisen. For antisense oligonucleotides to be able to inhibit translation they must reach the interior of the cell unaltered. The properties useful for oligonucleotides to be used for antisense inhibition include: (i) stability of the oligonucleotides towards extra- and intracellular enzymes; (ii) ability to penetrate through the cell membrane; and (iii) ability to hybridize the target DNA or RNA (Agarwal, K. L. et al., *Nucleic Acids Res.*, 1979, 6, 3009; Agawal, S. et al., *Proc Natl Acad Sci. USA*. 1988, 85, 7079). Thus, it is of interest to provide polynucleotide analogs that have superior properties for use as antisense or for use as primers or hybridization, probes.

Modified polynucleotides have been synthesized in the past, these polynucleotide modifications include methylphophonates, phosphorothioates, various amidates and the sugar moieties of the nucleic acid species. These backbone substitutions confer enhanced stability to some degree but suffer from the drawback that they result in a chiral phosphorous in the linkage, thus leading to the formation of $2^n$ diastereomers where n is the number of modified diester linkages in the oligomer. The presence of these multiple diastereomers considerably weakens the capability of the modified olgonucleotide to hybridize to target sequences. Some of these substitutions also retain the ability to support a negative charge and the presence of charged groups decreases the ability of the compounds to penetrate cell membranes. There are numerous other disadvantages associated with these modified linkages, depending on the precise nature of the linkage.

Some oligonucleotide analogs containing sugar modifications have been synthesized. Previously used sugar modifications of (deoxy)ribose nucleic acids include α-DNA, homo DNA, morpholino and thio nucleosides and Peptide Nucleic Acids (PNA) to provide what has been perceived to be improved structures, especially structures which have improved cell uptake. The general synthetic scheme for arriving at such analogs has been to involve the primary hydroxyl group of a nucleoside or its nucleotide, either bound to a polymeric carrier or to a sequence-specified 3'-nucleotide with phosphorus atom in either the pentavalent or trivalent oxidation state. Specific coupling procedures have been referred to as the phosphite triester (phosphoramidite), the phosphorus diester, and the hydrogen phosphonate procedures. Commercially available monomers and polymeric carriers-bound monomers are available for such methods having protected bases (G, A, C, T, U and other heterocycles) along with protected phosphorus atoms to allow storage and prevent non-specific reactions during the coupling process.

Nucleic acid species containing modified sugars, nonionic backbones or acyclic polyamides (PNA) having, to some degree, one or more of the following properties useful for gene modulation: to enhance the duplex stability (hybridization efficiency), increased target specificity, stability against nucleases, improved cellular uptake, and assistance in the important terminating events of nucleic acids (e.g. RNase H activity, catalytic cleavage, hybridization arrest, and others). It has also been suggested to use carbonate diesters. However, these compounds are highly unstable, and the carbonate diester link does not maintain a tetrahedral configuration exhibited by the phosphorous in the phosphodiester. Similarly, carbamate linkages, while achiral, confer trigonal symmetry and it has been shown that poly dT having this linkage does not hybridize strongly with poly dA (Coull, J. M. et al., *Tetrahedron Letts.*, 1987, 28, 745; Stirchak, E. P. et al., *J. Org. Chem.*, 1987, 52, 4202).

More recently, reports of acyclic sugar analogs have appeared in the literature (Augustyns, K. A. et al., *Nucleic Acids Res.*, 1991, 19, 2587–2593). Incorporation of these acyclic nucleosides into oligonucleotides caused a drop in Tm, depending on the number of linkers built in the oligomers. These oligonucleotides are found to be enzymatically stable and form base pairing with the complementary sequence. Given the shortcomings of polynucleotides and known polynucleotide analogs, it is of interest to provide new polynucleotide analogs for use in antisense inhibition and other techniques employing oligomers.

Such attempts at modifying both the sugar and the backbone components have some shortcomings for use as therapeutics and in other methods. Hence, still greater improvements in these qualities is required before effective therapeutics, diagnostics and research tools become available. Accordingly, there is a long-felt need for improved oligomer analogs of oligonucleotides as pharmaceuticals compounds.

The present invention provides novel oligonucleotides, and structural precursor thereof, which have improved resistance to nuclease digestion, and which have increased stability under physiological conditions, and which can be neutral or positively charged that could enhance cell permeation. Furthermore, the novel oligonucleotides of the present invention improved hybridization properties with respect to nucleic acid hybridization targets.

The oligomers of the present invention are generally characterized as comprising a series of constrained linkers or monomers that is appropriate for binding of heterocyclic bases to a target nucleic acid in a sequence specific manner. The constrained linkers described herein, when incorporated into oligomers, may have a force greater than a single hydrogen bond, thereby favoring formation of the binding competent conformation.

The nucleomonomers of the present invention are generally characterized as moieties or residues that replace the furanose ring, that is found in naturally occurring nucleotides, with an amino acid or a modified amino alcohol residues. Exemplary monomers and oligomers of the invention are shown in formulae 1 through 41. Incorporation of these monomers described herein into oligonucleotides permits synthesis of compounds with improved properties, these improved properties include (i) increased lipophilicity which results from eliminating the charge associated with phosphodiester linkages (Dalge, J. M. et al., *Nucleic Acids Res.*, 1991, 19, 1805) and (ii) resistance to degradation by enzymes such as nucleases. Oligomers containing these monomers may be quite stable for hybridization to target sequences and superior to unmodified nucleoside residues in one or more applications.

SUMMARY OF THE INVENTION

The present invention provides various novel oligonucleotide analogs having one or more properties that make the subject compounds superior to conventional oligonucleotides for use in procedures employing oligonucleotides. The compounds of the invention are oligonucleotide analogs in which the furanose ring of a naturally occurring nucleic acid is replaced with an amino acid or a modified amino alcohol residue. Some embodiments of the novel compounds of the invention are particularly useful for the antisense control of gene expression. The compounds of the invention may also be used as nucleic acid hybridization probes or as primers.

Another aspect of the invention is to provide monomeric precursors of the oligonucleotide analogs of the invention. These monomeric precursors may be used to synthesize the subject polynucleotide analogs.

Another aspect of the invention is to provide formulations of the subject polynucleotide analogs that are designed for the treatment or prevention of disease conditions. Yet another aspect of the invention is to provide methods for treating or preventing diseases, particularly viral infections and cell growth disorders. The subject disease treatment methods comprise the step of administering an effective amount of the subject polynucleotide analogs for use as antisense inhibitors.

BRIEF DESCRIPTION OF THE FIGURES

FIG. 1 shows the synthesis of L-serinol coupled thymine monomer phosphoramidite with a —$CH_2$—CO— linkage between thymine and serinol.

FIG. 2 shows the synthesis of L-serinol coupled thymine monomer phosphoramidite with a —$CH_2$—$CH_2$— linkage between thymine and serinol.

FIG. 3 and 4 depicts the synthesis of substituted L-serinol coupled thymine monomer phosphoramidites with a —$CH_2$—CO— linkage between thymine and serinol.

FIG. 5 shows the synthesis of T—T dimer with 5 atom long inter nucleotide linkage having hydroxylamine in the middle of the internucleotide linkage with a —$CH_2$—CO— linkage between thymine and serinol.

FIG. 6 depicts the synthesis of thymine monomer phosphoramidite in which thymine is connected to an N-ethylhydroxylamine through a —$CH_2$—CO— linkage.

FIG. 7 shows the synthesis of L-serinol coupled thymine monomer phosphoramidite in which the $NH_2$ group of L-serine is connected to 2-hydroxyacetyl group and the hydroxy function is blocked with DMT group. This building block is used for 2'-5' connection. This figure also depicts the synthesis of thymine monomer in which the $NH_2$ group of L-serine is connected to a 2'-hydroxyethyl function.

FIG. 8 shows the synthesis T—T dimer having a hydroxamate backbone with 2'-5' linkage. In this dimer one building block is made from L-aspartic acid and thymine and the other is from L-serine and thymine. This dimer has two additional amide bond in the backbone.

FIG. 9 depicts the synthesis T—T dimer having hydroxamate backbone with 2'-5' linkage. In this dimer one building block is made from L-aspartic acid and thymine and the other is from L-serine and thymine. This dimer lacks amide bond between in the backbone.

FIG. 10 shows the synthesis of L-serinol-b-alanine coupled thymine monomer phosphoramidite in which β-alanine links thymine and serinol.

FIG. 11 shows the synthesis of L-serinol-akylamine coupled thymine monomer phosphoramidite with alkyamine links thymine and serinol.

FIG. 12 depicts the synthesis T—T dimer having hydroxamate backbone with 4'-5' linkage. In this, the dimer is made from two L-aspartic acid units and two thymine units with an acetyl linker between thymine and aspartic acid.

FIG. 13 depicts the synthesis T—T dimer having hydroxamate backbone with 4'-5' linkage. In this, the dimer is made from two L-aspartic acid units and two thymine units with an ethyl linker between thymine and aspartic acid.

FIG. 14 shows the synthesis of N-hydroxyamino acid coupled thymine building block.

FIG. 15 shows the synthesis of L-aspartic acid coupled thymine building block with an N-hydroxylamine linker between thymine and aspartic acid.

FIG. 16 depicts the synthesis T—T dimer having a hydroxamate backbone with 4'-5' linkage. In this, the carboxylic acid group is coupled to thymine building block through an N-hydroxylamine linker.

FIG. 17 depicts the synthesis thymidineacetic acid substituted N-hydroxyamino acid building block 150 and its analogue 149. These monomer building blocks are useful to create nucleic acid with hydroxamate backbones.

FIG. 18 shows the synthesis of thymidineacetic acid substituted hydroxylamine containing amino acid building blocks 157 and 158. These monomers are useful to design nucleic acid having amide backbone with hydroxylamine functionality.

FIG. 19 shows the synthesis of L-serinol coupled thymidine building block 166 having a hydroxylamine moiety between thymine and serinol. This building block is useful to devise nucleic acid of 4'-5' linkages.

FIG. 20 depicts the synthesis of glutamic acid-glycine coupled Thymidine monomer 174. This monomer building block is useful to generate nucleic acid with amide backbones and 2'-5' linkages.

FIG. 21 shows the synthesis of glycinol-glycine coupled thymidine building block 181 and 182 having a hydroxylamine moiety between thymine and glycinol. These building blocks are useful to prepare nucleic acid of 2'-5' linkages.

FIGS. 22 through 24 indicate the synthesis of ribose amino acid coupled thymidine building blocks 191, 199 and 207. These building blocks are useful to prepare oligonucleotides having ribose-amide backbone.

FIG. 25 depicts the solid phase synthesis of oligonucleotide 211 having ribose-amide backbone.

DETAILED DESCRIPTION OF THE SPECIFIC EMBODIMENTS

A. Definitions and Abbreviations

Figure 1:
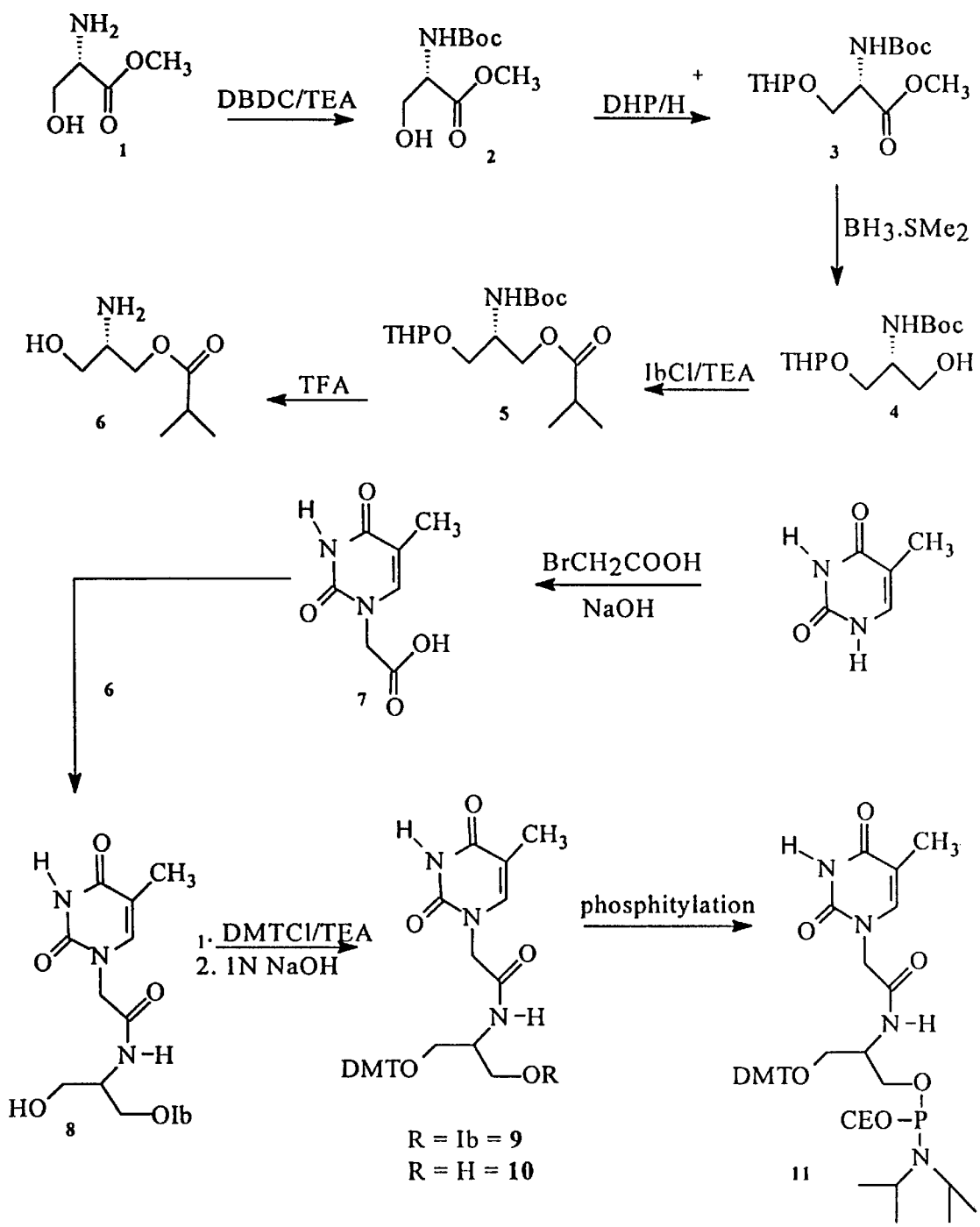
FIGS. 1 through 25 are depictions of chemical reaction sequences usable for synthesizing monomers and oligonucleotides of the present invention. More specifically.

In describing the present invention, the following terms will be employed, and are intended to be defined as indicated below.

As used herein, "antisense" therapy refers to administration or in situ generation of DNA or RNA oligomers, or their analogs thereof, which bind specifically to a complementary target nucleic acid sequence. The binding may be by conventional base pair complementarily, or the binding may through other mechanisms, for example, in the case of binding to DNA duplexes, through specific interactions in the major groove of the double helix. In general, "antisense" refers to a range of techniques generally employed under this description in the art, and includes any therapy which relies on specific binding to oligonucleotide sequences. The techniques of antisense gene regulation are well known to the person of ordinary skill in the art of molecular biology descriptions of antisense gene regulation can be found, for example, in U.S. Pat. No. 5,107,065, U.S. Pat. No. 5,166, 195, U.S. Pat. No. 5,087,617, and Crooke, Annual Review Pharmacology Toxicology 1992 32; 329–376.

The terms "Oligomer" or "Oligonucleotide" are used interchangeably and include naturally occurring compounds such as RNA and DNA, as well as synthetic analogs thereof, including compounds of the invention. Unless indicated otherwise, the terms "oligomer" and "oligonucleotide" refer to both DNA/RNA and to synthetic analogs thereof. The term "oligomer" refers to compounds comprising two or more nucleomonomers covalently attached to each other by a phosphodiester linkage or any other substitute linkages. Unless indicated otherwise, a lengthy limitation should not be read into the term "oligomer". Thus, an oligomer can have as few as two covalently linked nucleomonomers ( a dimer )or may be significantly longer. Oligomers can be binding competent and, thus, can base pair with single-stranded or double-stranded nucleic acid sequences. Oligomers (e.g. dimers-hexamers) are also useful as synthons for longer oligomers as described herein. Oligomers may contain abasic sites and pseudonucleosides.

The Oligomers includes oligonucleotides, oligonucleosides, polydeoxyribo-nucleotides (containing 2'-deoxy-D-ribose or modified forms thereof), i.e., DNA, polyribonucleotides ( containing D-ribose or modified forms thereof), i.e., RNA, and any other type of polynucleotide which is an N-glycoside or C-glycoside of purine or pyrimidine base, or modified purine or pyrimidine base. Oligomer as used herein is also intended to include compounds where adjacent nucleomonomers are linked via hydroxamate linkages. Elements ordinarily found in oligomers, such as the furanose ring and/or the phosphodiester linkage can be replaced with any suitable functionally equivalent element. The term "Oligomer" is intended to include any structure that serves as a chassis or support for the bases wherein the chassis permits binding to target nucleic acids in a sequence-dependent manner. Oligomers that are currently known can be defined into four groups that can be characterized as having (i) phosphodiester or phosphodiester analog (phosphorothiaoate, methylphosphonate, etc) linkages, (ii) substitute linkages that contain a non-phosphorous isostere (riboacetal, formacetal, carbamate, etc), (iii) morpholino residues, carbocyclic residues or other furanose sugars, such as arabinose, or a hexose in place of ribose or deoxyribose and (iv) nucleomonomers linked via amide bonds or acyclic nucleomonomers linked via any suitable substitute linkage.

The term "Nucleomonomer" as used herein refers to a moiety comprising (1) a base covalently linked to (2) a second moiety. Nucleomonomers include nucleosides, nucleotides or bases connected to an amino alcohol. Nucleomonomers can be linked to form oligomers that bind to target or complementary base sequences of nucleic acids in a sequence specific manner.

A "second moiety" as used herein refers to a compound linked to a Nucleomonomer, and includes an amino acid/ amino alcohol moiety, usually serinol, aspartic acid, glutamic acid, glycine, and those species which contain modifications of the amino acid moiety, for example, wherein one or more of the hydrogen is replaced with other functionality (see formulae 24–41), or one carboxylic acid is functionalized to an alcohol, amines, thiols, hydroxylamines, and the like. Nucleomonomers as defined herein are also intended to include a base linked to an amino acid or amino alcohol and/or amino acid/alcohol analog having a free carboxyl/hydroxyl group and/or a free amino group and/or protected forms thereof.

The term "Nucleoside" as used herein refers to an amino acid and amino alcohol derivative thereof, as described further below, carrying a purine, pyrimidine, or analogous forms thereof, as defined below, but lacking a linking moiety such as a phosphodiester analog or a modified internucleoside linkage. By "5'" nucleoside is meant the nucleoside which provides the 5' carbon coupling point to the linker. The "5'" end of the linker couples to the 5' nucleoside. The "3'" end of the linker joins to the 3' position on the next nucleoside. If a modified nucleoside is present which does not precisely include a 3' and/or a 5' carbon, it is understood by the person skilled in the art that this "3'" and "5'" terminology to describe strand polarity used by analogy to DNA and RNA.

The term "Nucleoside" as used herein refers to a base covalently attached to an amino alcohol/amino acid analog and which contain a linker between base and the amino acid/amino alcohol. The term nucleoside normally includes ribonucleosides, deoxyribonucleosides, or any other nucleoside which is an N-glycoside or C-glycoside of a base.

The term "Nucleotide" as used herein refers to a nucleoside having a phosphate group or a phosphate analog (groups with phosphorous in the same oxidation state as in the phosphate group e.g. thiophosphate, amidate).

The term "Base" as used herein refers to a wide variety of nucleoside base, including purine and pyrimidine heterocycles and heterocyclic analogs and tautomers thereof. Purines include adenine, guanine and xanthine and exemplary purine analogs include 8-oxo-$N_6$-methyladenine and 7-deazaxanthine. Pyrimidines include uracil and cytosine and their analogs such as 5-methylcytosine, 5-(1-propynyluracil), 5-(1-propynylcytosine), 5-methyluracil and 4,4-ethanocytosine. "Bases", when joined to a suitable molecular framework, e.g. a phophodiester backbone, are capable of entering into a base pairing relationship that occur in double-stranded DNA or other double-stranded nucleic acid of similar structure. Bases may also be capable of entering into a base pairing relationship in a triple helix nucleic acid.

The term "Sugar Modification" as used herein refers to any amino acid or amino alcohol moiety other than 2'-deoxyribose.

The term "Amino Acids/Alcohol" as used herein refers to any natural amino acids and alcohols of both "R'" and "S" isomers.

The term "Nucleoside Linkages" as used herein refers to the linkage that exists within the monomer.

The term "Linkage" as used herein refers to the moiety that is used to connect the base with amino acid/amino alcohol and derivatives thereof.

The term "Internucleotide Linkages" as used herein refers to a phophodiester moiety (—O—P(O)(O)—O—) or any other functionally equivalent moiety that covalently connects adjacent nucleomonomers.

The term "Substitute Linkages" as used herein refers to any analog of the native group or any suitable moiety that covalently couples adjacent nucleomonomers. Substitute linkages include phosphodiester analogs, e.g. such as phosphorothioate and methylphosphonate, and nonphosphorus containing linkages, e.g. such as amides, hydroxamates, hydroxylamine. Substitute linkages include the nonphosphorous containing linkages (2',5' linkages, 3',5' linkages and 4',5' linkages) of the invention.

The term "Crosslinking moiety" as used herein refers to a group or moiety in an oligomer that forms a covalent bond with a target nucleic acid. Crosslinking moieties include covalent binding species that covalently link an oligomer to target nucleic acids either spontaneously (e.g. $N^4,N^4$-ethanocytosine) or via photoactivation (e.g. psoralen) and the like.

The term "Blocking Groups" as used herein refers to a substituent other than H that is covalently coupled to oligomers or nucleomonomers, either as a protecting group, a coupling group for synthesis, $OPO_{3-2}$, or other conventional conjugate such as a solid support, label, antibody, monoclonal antibody or fragment thereof and the like. As used herein, "blocking group" is not intended to be construed solely as a protecting group, according to slang terminology, but is meant also to include, for example, coupling groups such as a H-phosphonate or a phosphoramidite.

The term "protecting group" as used herein refers to any group capable of protecting the O-atom, S-atom or N-atom to which it is attached from participating in a reaction or bonding. Such protecting groups for N-atoms on a base moiety in a Nucleomonomer and their introduction are conventionally known in the art. Non-limiting examples of suitable protecting groups include: diisobutylformamidine, benzoyl, silyl and the like. Suitable protecting groups for O-atoms and S-atoms are, for example, DMT, MMT, FMOC or esters. "Protecting groups" as used herein includes any group capable of preventing the O-atom, S-atom, or N-atom to which it is attached from participating in a reaction or binding. Such protecting groups for O-, S-, and N-atoms in nucleomonomers are described and the methods for their introduction are conventionally known in the art. Protecting groups also include any group capable of preventing reactions and bonding at carboxylic acids, thiols and the like.

The term "Coupling group" as used herein refers to any group suitable for generating a linkages or substitute linkage between nucleomonomers such as a hydrogen phosphonate and a phosphoramidite.

The term "Conjugate" or "conjugate moiety" as used herein refers to any group attached to the oligomer at a terminal end or within the oligomer itself. Conjugates include solid supports, such as silica gel, controlled pore glass and polystyrene; labels, such as fluorescent, chemiluminescent, radioactive atoms or molecules, enzymatic moieties and reporter groups; oligomer transport agents, such as polycations, serum proteins and glycoproteins and polymers and the like. Other conjugate moities include O-cholesterol, polyethylene glycol (PEG), amino acids, intercalators, polynucleotide clearing moieties, crosslinking functionalities, lipids, hydroxamates, alkylating agents and the like.

The term "Synthon" as used herein refers to a structural unit within an oligonucleotide analog of the invention.

The term "Transfection" as used herein refers to any method that is suitable for enhanced delivery of oligomers into cells.

The term "Subject" as used herein refers to a plant or animal, including mammal, particularly a human.

The term "Derivatives" and monomeric constituents thereof oligomers include those conventionally recognized in the art. For instance, the oligonucleotides may be covalently linked to various moieties such as intercalators, substances which interact specially with the minor groove of the DNA double helix and other arbitrarily chosen conjugates, such as labels (radioactive, fluorescent, enzyme, etc.). These additional moieties may be (but need not be) derivatized through the modified backbone linkage as part of the linkage itself. For example, intercalators, such as acridine can be linked through an R—$CH_2$— attached through any available —OH or SH, e.g.., at the terminal 5' position of RNA or DNA, the 2' position of RNA, or an OH or SH engineered into the 5 position of pyrimidines, e.g., instead of the 5 methyl of cytosine, a derivatized form which contains —$CH_2CH_2CH_2OH$ or —$CH_2CH_2CH_2SH$ in the 5 position. A wide variety of substituents can be attached, including those bound through conventional linkages. Accordingly the indicated OH moieties in the oligomer of formula (1) may be replaced by phosphonate groups, protected by standard protecting groups, or activated to prepare additional linkages to other nucleotides, or may be bound to the conjugated substituent. The 5' terminal OH is conventionally phosphorylated; the 2'—OH or OH substituents at the 3' terminus may also be phosphorylated. The hydroxyls may also be derivatized to standard protecting groups.

The term "phosphodiester analog" as used herein refers to an analog of the conventional phosphodiester linkage as well as alternative linking groups. These alternative linking groups include, but are not limited to embodiments wherein the O—P(O) is replaced with P(O)S, P(O)NR$_2$, P(O)R, P(O)OR', where R is H or alkyl (1–7C) and R' is alkyl (1–7C). Not all phosphodiester analogs in the same oligomer need to identical, the only requirement being that at least one of these linkages is a modified internucleotide linkage as described herein.

"Analogous" forms of purines and pyrimidines are those generally known in the art, many of which are used as chemotherapeutic agents. An exemplary but not exhaustive list includes 4-acetylcytosine, 8-hydroxy-N$^6$-methyladenine, aziridinylcytosine, pseudoisocytosine, 5-(carboxyhydroxymethyl) uracil, 5-fluorouracil, 5-bromouracil, 5-carboxvmethylaminomethyl-2-thiouracil, 5-carboxymethylaminomethyluracil, dihydrouracil, inosine, N$_6$-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N$_6$-methyladenine, 7-methyladenine, 7-methylguanine, 5-methylaminomethyluracil, 5-methoxyaminomethyl-2-thiouracil, beta-D-mannosylguanosine, 5'-methoxycarbonylmethyluracil, 5-methoxyuracil, 2-methylthio-N$_6$-isopentenyladenine, uracil-5-oxyacetic acid methylester, uracil-5-oxyacetic acid, oxybutoxosine, pseudouracil, gueosine, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

A particularly preferred analog is 5-methylcytosine (abbreviated herein as "Cme").

The term "Isosteric" as used herein refers to the spatial and orientation properties of an internucleoside linkage and the fact that these properties are so similar to those of the native phosphodiester linkage that the modified oligonucleotide containing an isosteric bond will replace, substitute for, mimic and/ or hybridize with a native oligonucleotide.

The term "Ribose-amide" as used herein refers to the internucleotide linkage that exists between two nucleobases. The ribose-amide internucleotide linkage has combination of ribose/(2'-deoxy) and amino acid functionalities.

Various abbreviations are used in this application to refer to functional groups and compounds. These abbreviations are readily understood by the person skilled in the art of organic chemistry, for example, "Ph" refers to phenyl, "Me" refers to methyl, "(1–7C)" indicates that a given chain contains anywhere from 1 to 7 carbons, etc.

DESCRIPTION OF THE INVENTION

The present invention provides novel oligonucleotide analogs containing modified amino acid/amino alcohol linkages between the bases and the backbones (phosphodiester, phosphorothioates and others as shown in table 1) also referred to as modified nucleotide linkages. The modifications or functional equivalent thereof, replacing the sugar moiety that lies between the backbone and the bases with an amino acid derivatives, for example as shown in formulae 24. The present invention is also provides novel nucleomonomers and methods for their incorporation into oligomers containing the nucleomonomers.

The invention provides various nucleomonomer compounds aving the structures of formulae 1–23.

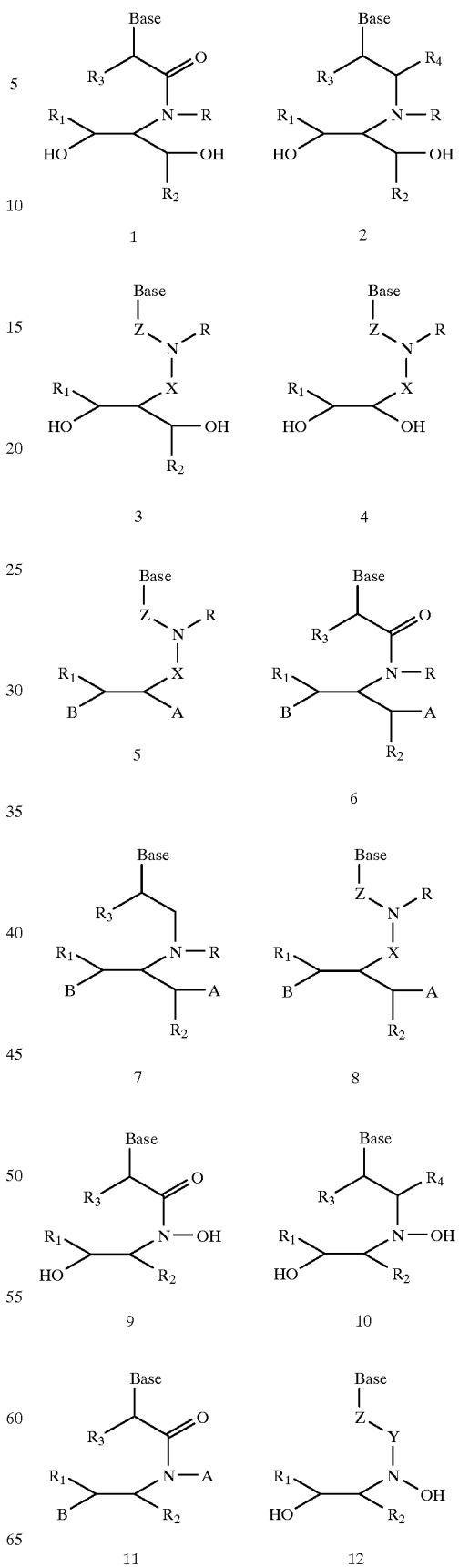

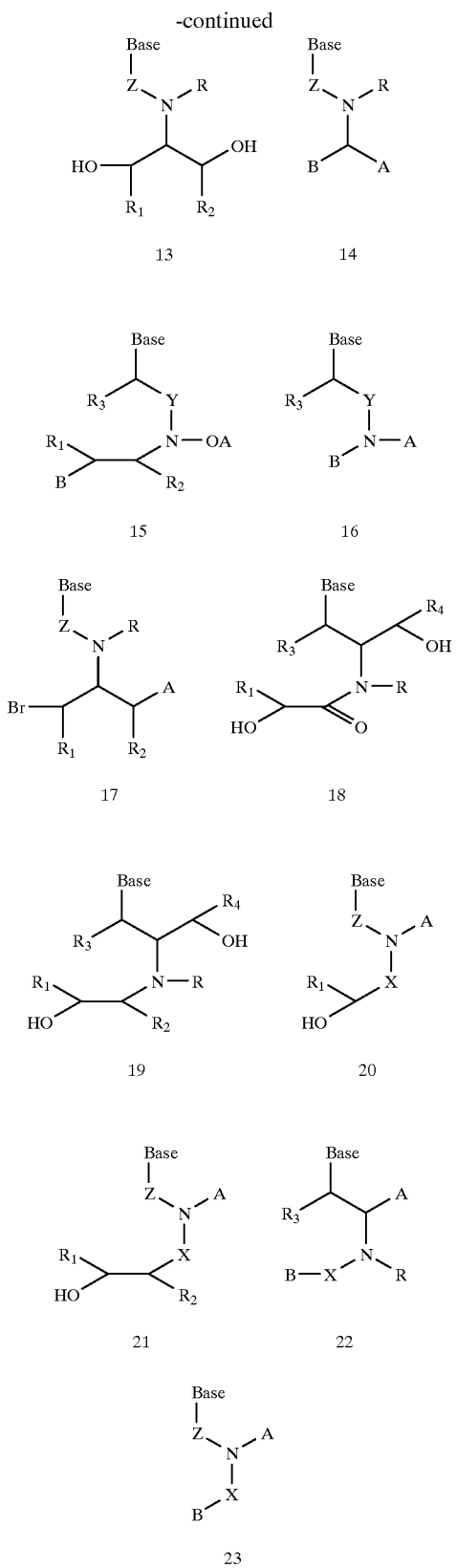
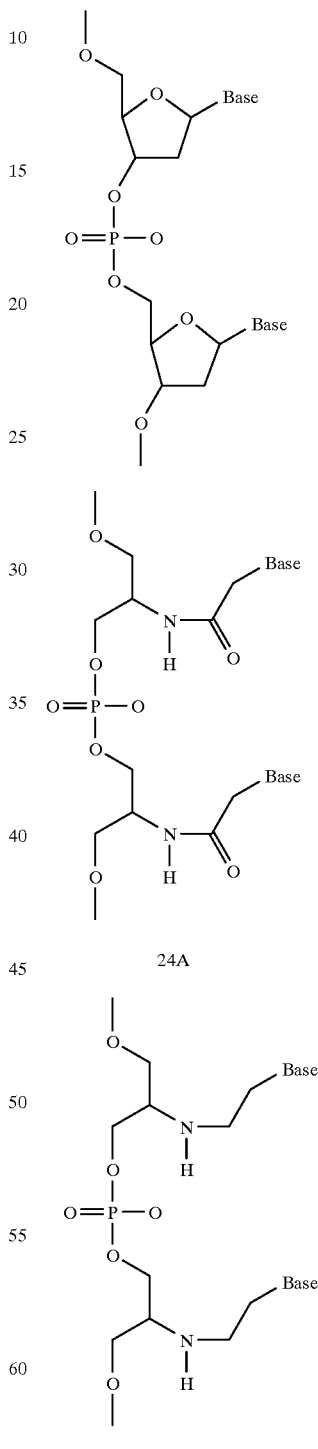

oligomers of the invention comprises two or more nucleomonomers and many comprises virtually any number of nucleomonomers, although oligomers of 200 or less nucleomonomers are generally easier to synthesize. Compounds of formulae 1–23, may be joined to one another through 4'–5' linkages, 3'–5' linkages, and 2'–5' linkages, as can be seen in formulae 24–41.

The oligomers of the invention are polymers comprising one or more of the subject monomer compounds joined so as to provide a structural analog of DNA or RNA. The nucleotide linkages in the compounds of the invention are made from amino acids serine and glycine or derivatives thereof. The oligonucleotides of the invention are stable in vivo, resistant to endogenous nucleases and are able to hybridize to target nucleotide sequences. Exemplary compounds of this invention are shown in formulae 24 through 41 and are conformationally more restricted relative to the phosphodiester linkages found in unmodified DNA or RNA. This conformational restriction may, in part, contribute to the enhanced binding properties of the subject compounds to complementary polynucleotide target sequences; however, the use of the invention is not dependent upon this theory for enhanced binding properties.

In another embodiment, the present invention is directed to a modified oligonucleotide or derivatives thereof, wherein the furanose moiety of a natural oligonucleotide, e.g., DNA or RNA is replaced with amino acid/amino alcohol moiety and other modifications that comprises substitution at the amino acid positions are shown in the formulae 25 to 41. The internucleotide linkages between adjacent nucleomonomers is a linkage between the 4' and 5' position of adjacent nucleomonomers. In other words, the phosphodiester internucleotide linkage, or functional equivalent thereof, originates from 5'-position of one nucleomonomer and connects the 4'-position of adjacent monomer as exemplified by the compounds of formulae 24–33:

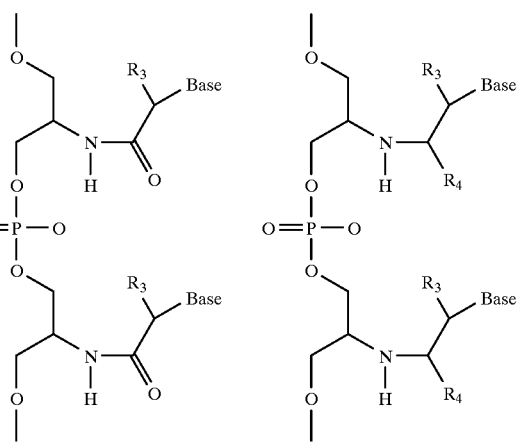

27A 27B

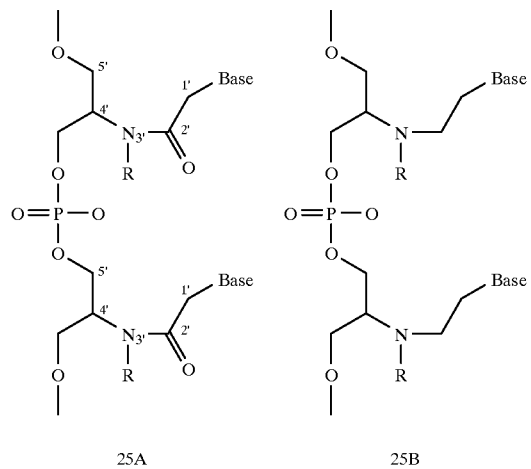

25A 25B

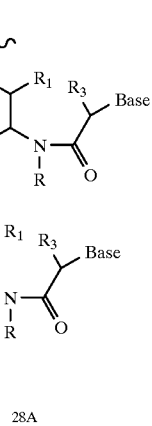
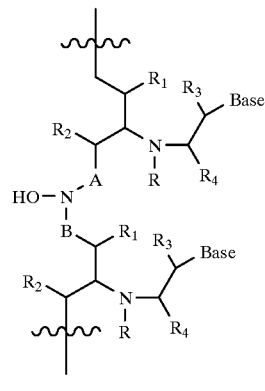

28A 28B

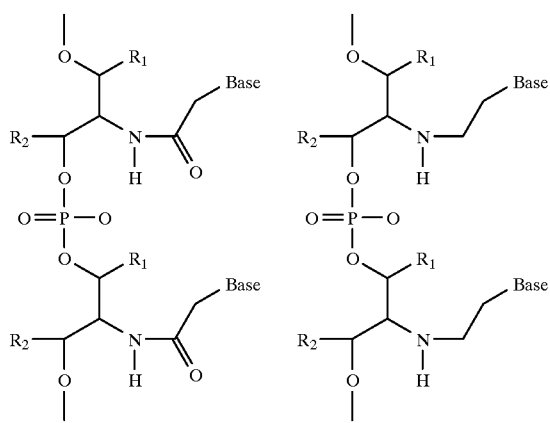

26A 26B

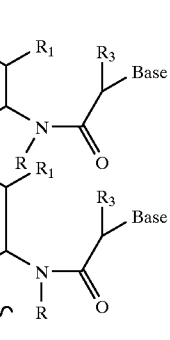
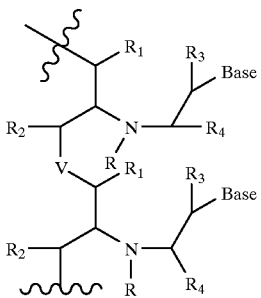

29A 29B

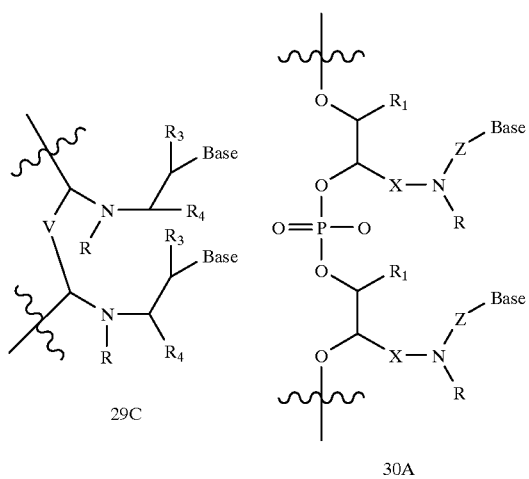

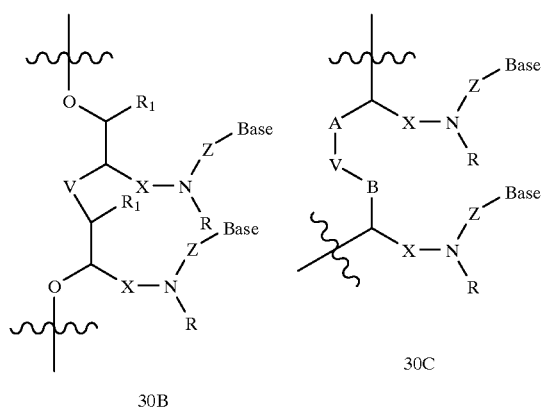

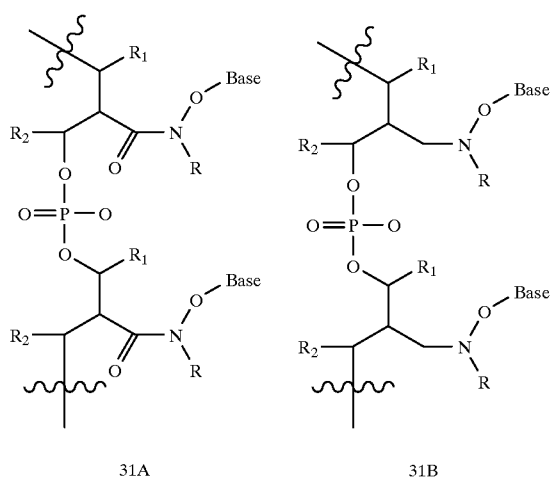

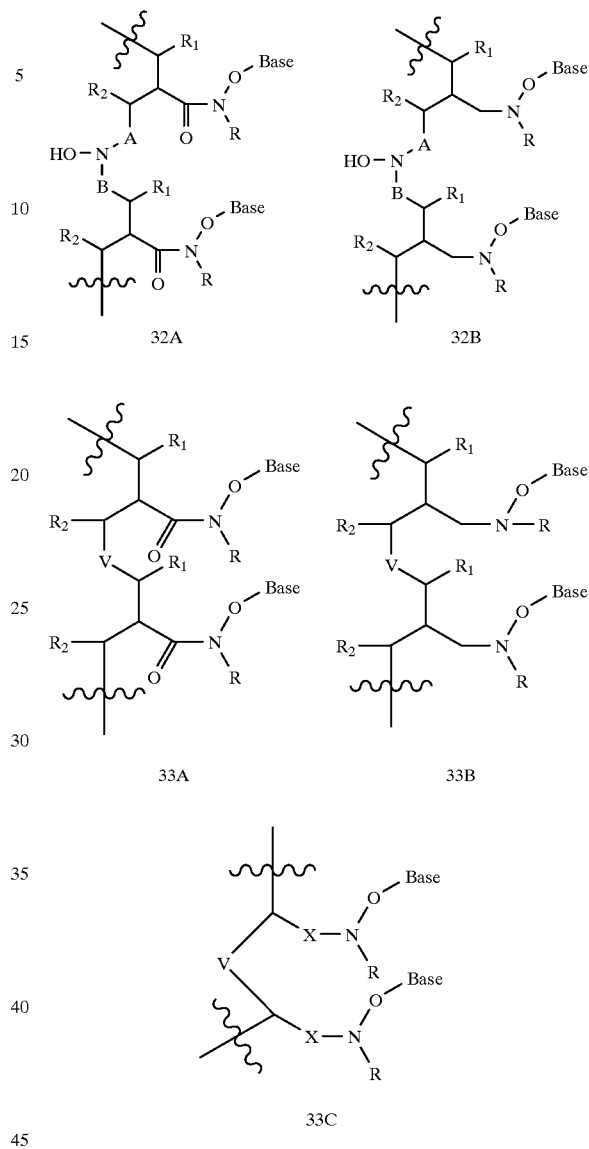

Wherein each "R" is independently H, OH, SH, CN, CH$_3$, OCH$_3$, SCH$_3$, ONH$_2$, ONH(CH$_3$), Ph, —(CH$_2$)$_x$—F; where "x" is 1–7 carbon and "F" is NH$_2$, SH, OH, COOH, OCH$_3$, SCH$_3$, SPh, NOH, NOH(CH$_3$), SNH$_2$, S(O)NH$_2$, S(O)(O)NH$_2$, CH$_3$, Ph.

Wherein each "Base" is independently a nucleoside base.

Wherein each "R$_1$" is independently H, OH, SH, CN, CH$_3$, OCH$_3$, SCH$_3$, ONH$_2$, ONH(CH$_3$), Ph, —(CH$_2$)$_x$—F; where "x" is 1–7 carbon and "F" is NH$_2$, SH, OH, COOH, OCH$_3$, SCH$_3$, SPh, NOH, NOH(CH$_3$), SNH$_2$, S(O)NH$_2$, S(O)(O) NH$_2$, CH$_3$, Ph.

Wherein each "R$_2$" is independently H, OH, SH, CN, CH$_3$, OCH$_3$, SCH$_3$, ONH$_2$, ONH(CH$_3$), Ph, —(CH$_2$)$_x$—F; where "x" is 1–7 carbon and "F" is NH$_2$, SH, OH, COOH, OCH$_3$, SCH$_3$, SPh, NOH, NOH(CH$_3$), SNH$_2$, S(O)NH$_2$, S(O) (O)NH$_2$, CH$_3$, Ph.

Wherein each "R$_2$" is independently H, OH, SH, CN, CH$_3$OCH$_3$, SCH$_3$, ONH$_2$, ONH(CH$_3$), Ph, —(CH$_2$)$_x$—F; where "x" is 1–7 carbon and "F" is NH$_2$, SH, OH, COOH, OCH₃, SCH₃, SPh, NOH, NOH(CH₃), SNH₂, S(O)NH₂, S(O) (O)NH₂, CH₃, Ph.

Wherein each "R₄" is independently H, OH, SH, CN, CH₃, OCH₃, SCH₃, ONH₂, ONH(CH₃), Ph, —(CH₂)ₓ—F; where "x" is 1–7 carbon and "F" is NH₂, SH, OH, COOH, OCH₃, SCH₃, SPh, NOH, NOH(CH₃), SNH₂, S(O)NH₂, S(O) (O)NH₂, CH₃, Ph.

Wherein each "A" is independently (CH₂)ₓ, CO, CS, S, S(O), S(O)(O), NH, NOH, NCH₃, NR₅, and Se, where "x" is 1–7 carbon.

Wherein each "B" is independently (CH₂)ₓ, CO, CS, S, S(O), S(O) (O), NH, NOH, NCH₃, NR₅, and Se, where "x" is 1–7 carbon.

Wherein each "X" is independently (CH₂)ₓ, CO, CS, O, S, S(O), S(O) (O), NH, NOH, NCH₃ and NR₅, where "x" is 1–7 carbon.

Wherein each "Z" is independently (CH₂)ₓ, CO, CS, S, S(O), S(O)(O), NH, NOH, NCH₃ and NR₅, where "x" is 1–7 carbon.

R₅ is a H, OH, OMe, CN, NH, NOH, ONCH₃, ONH₂, ethyl, propyl, lower alkyl (1–7C), Me, heteroalkyl (1–7C), aryl(6–7C), —(CH₂)ₓF; where "x" is 1–7C, and "F" is independently H, OH, SH, OCH₃, CN, SCH₃, ONH₂, ONH (CH₃), SNH₂, S(O)NH₂, S(O)(O)NH₂, CH₃, Ph.

Wherein each "V" is independently a phosphodiester analog, phosphorothioates, methylphosphonates, phosphorodithioates, boronphosphonates, selenophosphonates, phosphoramidates, acetamidate, oxyformamido, oxyacetamido, diisopropylsilyl, carbamate, dimethylene sulfide, dimethylene sulfoxide, dimethylene sulfone and/ or two to four atom long internucleoside linkage is selected from carbon, nitrogen, oxygen, sulfur and selenium. The length of the oligomer may vary from a diner to a 200 mer, or longer. Preferred modified internucleotide linkages include the structures for "V" are shown in Table I.

Additionally, the compounds of formulae may be conjugated to one or more conjugate moiety. Suitably, conjugate moieties include O-cholesterol, polyethylene glycol, amino acids, intercalators, cleaving moieties (e.g., imdazole), crosslinking functionalities (e.g., psoralen), lipids, peptides, alkylating agents, hydroxamaes, and fluorescent labels. The conjugate moiety may independently replace one or more of R, R₁, R₂, R₃, R₄, and R₅.

In yet other embodiments, the subject invention provides oligomer structures as indicated in formulae 34–36 and derivatives thereof:

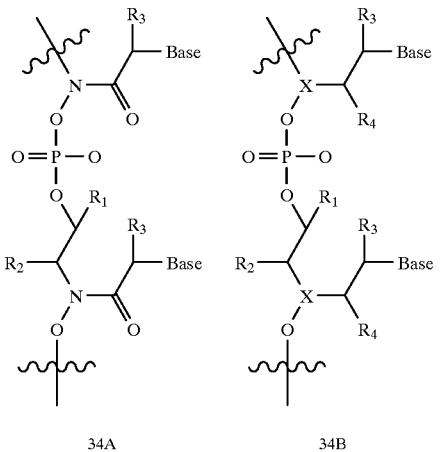

34A  34B

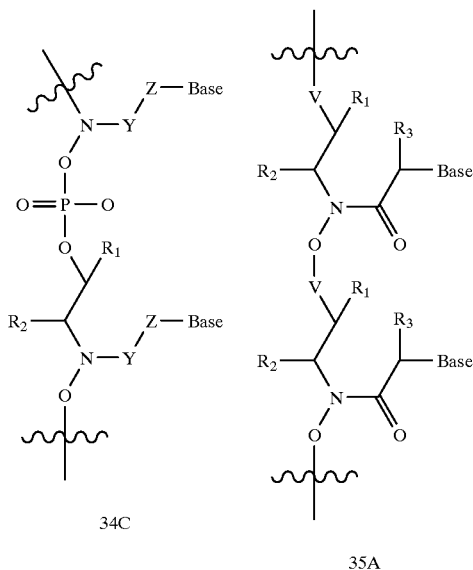

34C

35A

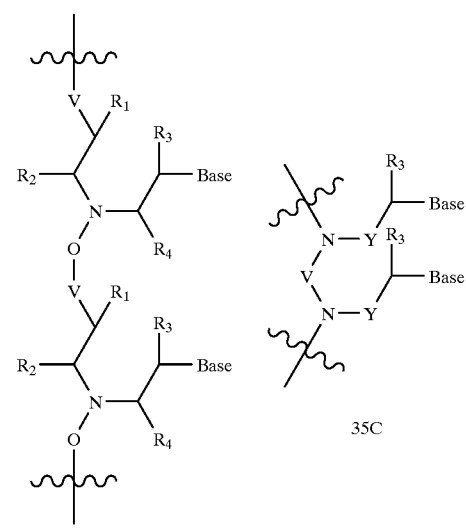

35B  35C

Formula 34

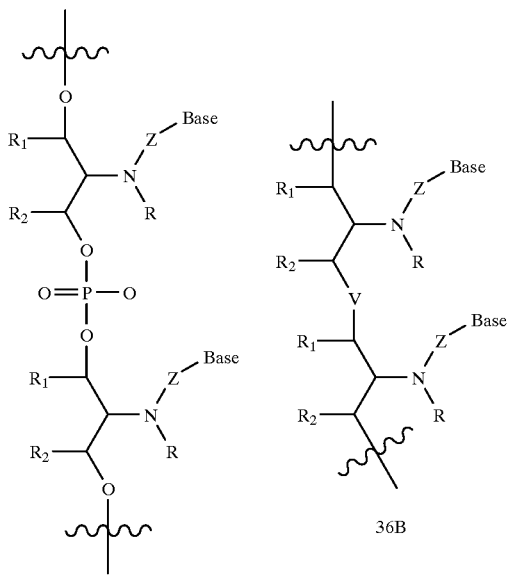

36A

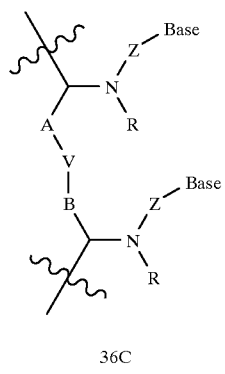

36B

36C

In the compounds of formulae 34–36, the linkages between adjacent nucleomonomers are 3' to 5' linkages.

Wherein each "R" is independently H, OH, SH, CN, CH$_3$, OCH$_3$, SCH$_3$, ONH$_2$, ONH(CH$_3$), Ph, —(CH$_2$)$_x$—F; where "x" is 1–7 carbon and "F" is NH$_2$, SH, OH, COOH, OCH$_3$, SCH$_3$, SPh, NOH, NOH (CH$_3$), SNH$_2$, S(O) NH$_2$, S(O)(O) NH$_2$, CH$_3$, Ph.

Wherein each "Base" is independently a nucleoside base.

Wherein each "R$_1$" is independently H, OH, SH, CN, CH$_3$, OCH$_3$, SCH$_3$, ONH$_2$, ONH(CH$_3$), Ph, —(CH$_2$)$_x$—F; where "x" is 1–7 carbon and "F" is NH$_2$, SH, OH, COOH, OCH$_3$, SCH$_3$, SPh, NOH, NOH(CH$_3$), SNH$_2$, S(O)NH$_2$, S(O) (O)NH$_2$, CH$_3$, Ph.

Wherein each "R$_2$" is independently H, OH, SH, CN, CH$_3$, OCH$_3$, SCH$_3$, ONH$_2$, ONH(CH$_3$), Ph, —(CH$_2$)$_x$—F; where "x" is 1–7 carbon and "F" is NH$_2$, SH, OH, COOH, OCH$_3$, SCH$_3$, SPh, NOH, NOH(CH$_3$), SNH$_2$, S(O)NH$_2$, S(O) (O)NH$_2$, CH$_3$, Ph.

Wherein each "R$_3$" is independently H, OH, SH, CN, CH$_3$, OCH$_3$, SCH$_3$, ONH, ONH(CH$_3$), Ph, —(CH$_2$)$_x$—F; where "x" is 1–7 carbon and "F" is NH$_2$, SH, OH, COOH, OCH$_3$, SCH$_3$, SPh, NOH, NOH(CH$_3$), SNH$_2$, S(O)NH$_2$, S(O) (O)NH$_2$, CH$_3$, Ph.

Wherein each "R$_4$" is independently H, OH, SH, CN, CH$_3$, OCH$_3$, SCH$_3$, ONH$_2$, ONH(CH$_3$), Ph, —(CH$_2$)$_x$—F; where "x" is 1–7 carbon and "F" is NH$_2$, SH, OH, COOH, OCH$_3$, SCH$_3$, SPh, NOH, NOH(CH$_3$), SNH$_2$, S(O)NH$_2$, S(O) (O)NH$_2$, CH$_3$, Ph.

Wherein each "A" is independently (CH$_2$)$_x$, CO, CS, S, S(O), S(O) (O), NH, NOH, NCH$_3$, NR$_5$ and Se. Where "x" is 1–7.

Wherein each "B" is independently (CH$_2$)$_x$, CO, CS, S, S(O), S(O) (O), NH, NOH, NCH$_3$, NR$_5$ and Se. Where "x" is 1–7.

Wherein each "X" is independently (CH$_2$)$_x$, CO, CS, O, S, S(O), S(O)(O), NH, NOH, NCH$_3$ and NR$_5$. Where "x" is 1–7.

Wherein each "Y" is independently (CH$_2$)$_x$, CO, CS, O, S, S(O), S(O) (O), NH, NOH, NCH$_3$ and NR$_5$. Where "x" is 1–7.

Wherein each "Z" is independently (CH$_2$)$_x$, CO, CS, S, S(O), S(O) (O), NH, NOH, NCH$_3$ and NR$_5$. Where "x" is 1–7.

R$_5$ is a H, OH, OMe, CN, NH, NOH, ONCH$_3$, ONH$_2$, ethyl, propyl, lower alkyl (1–7C), Me, heteroalkyl (1–7C), aryl(6–7C), —(CH$_2$)$_x$F; where "x" is 1–7C, and "F" is independently H, OH, SH, OCH$_3$, CN, SCH$_3$, ONH$_2$, ONH (CH$_3$), SNH$_2$, S(O)NH$_2$, S(O) (O)NH$_2$, CH$_3$, Ph.

Wherein each "V" is independently a phosphodiester analog, phosphorothioates, methylphosphonates, phosphorodithioates, boronphosphonates, selenophosphonates, phosphoramidates and/ or two to four atom long internucleoside linkage is selected from carbon, nitrogen, oxygen, sulfur and selenium. The length of the oligomers may vary from a dimer to a 200 mer, or longer. Preferred modified internucleotide linkages include the structures for "V" are shown in Table I.

In another embodiment of the invention, the subject invention provides oligomers having formulae 37 to 41, or variants thereof, oligomers comprising novel internucleotide linkages that are 2',5' linkages. These oligonucleotides are stable in vivo, have improved resistance to endogenous nucleases, and are able to hybridize to target oligonucleotide sequences.

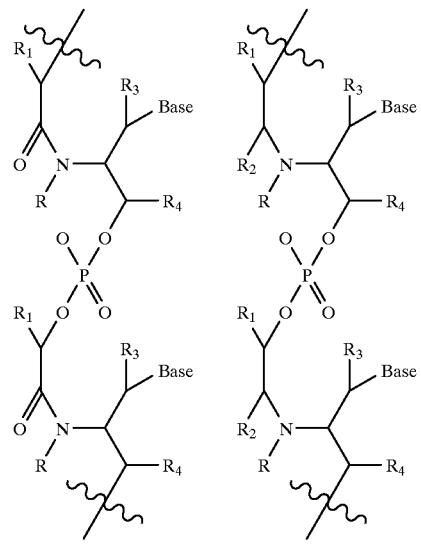

37A 37B

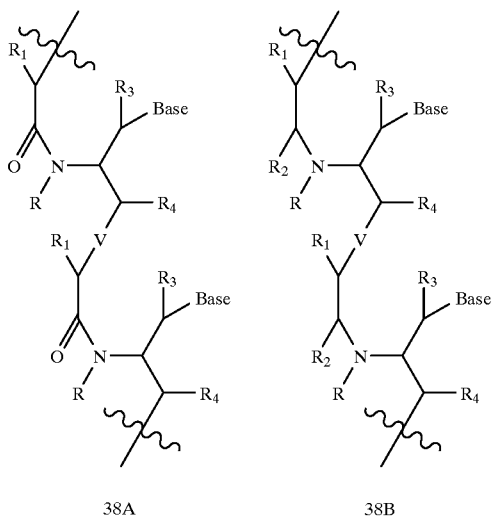

38A      38B

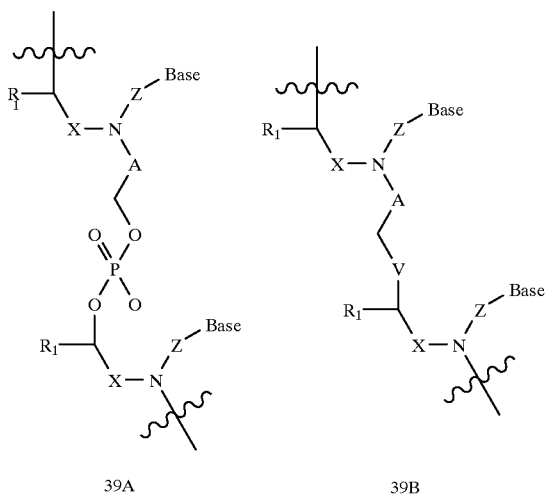

39A      39B

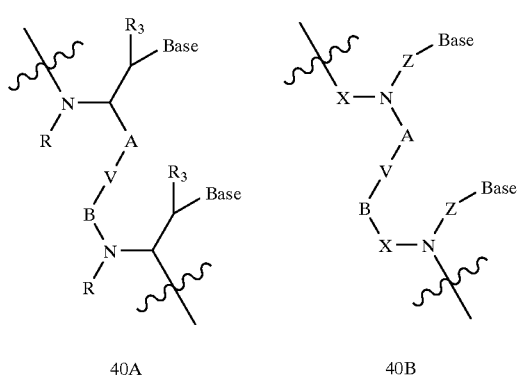

40A      40B

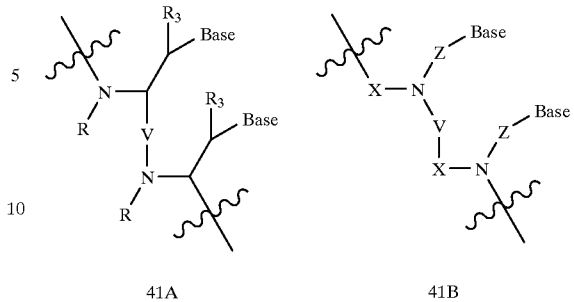

41A      41B

Wherein each "R" is independently H, OH, SH, CN, $CH_3$, $OCH_3$, $SCH_3$, $ONH_2$, $ONH(CH_3)$, Ph, —$(CH_2)_x$—F; where "x" is 1–7 carbon and "F" is $NH_2$, SH, OH, COOH, $OCH_3$, $SCH_3$, SPh, NOH, $NOH(CH_3)$, $SNH_2$, $S(O)NH_2$, $S(O)(O)NH_2$, $CH_3$, Ph.

Wherein each "Base" is independently a nucleoside base.

Wherein each "$R_1$" is independently H, OH, SH, CN, $CH_3$, $OCH_3$, $SCH_3$, $ONH_2$, $ONH(CH_3)$, Ph, —$(CH_2)_x$—F; where "x" is 1–7 carbon and "F" is $NH_2$, SH, OH, COOH, $OCH_3$, $SCH_3$, SPh, NOH, $NOH(CH_3)$, $SNH_2$, $S(O)NH_2$, $S(O)(O)NH_2$, $CH_3$, Ph.

Wherein each "$R_2$" is independently H, OH, SH, CN, $CH_3$, $OCH_3$, $SCH_3$, $ONH_2$, ONH $(CH_3)$, Ph, —$(CH_2)_x$—F; where "x" is 1–7 carbon and "F" is $NH_2$, SH, OH, COOH, $OCH_3$, $SCH_3$, SPh, NOH, $NOH(CH_3)$, $SNH_2$, $S(O)NH_2$, $S(O)(O)NH_2$, $CH_3$, Ph.

Wherein each "$R_3$" is independently H, OH, SH, CN, $CH_3$, $OCH_3$, $SCH_3$, $ONH_2$, $ONH(CH_3)$, Ph, —$(CH_2)_x$—F; where "x" is 1–7 carbon and "F" is $NH_2$, SH, OH, COOH, $OCH_3$, $SCH_3$, SPh, NOH, NOH $(CH_3)$, $SNH_2$, $S(O)$ $NH_2$, $S(O)(O)$ $NH_2$, $CH_3$, Ph.

Wherein each "$R_4$" is independently H, OH, SH, CN, $CH_3$, $OCH_3$, $SCH_3$, $ONH_2$, $ONH(CH_3)$, Ph, —$(CH_2)_x$—F; where "x" is 1–7 carbon and "F" is $NH_2$, SH, OH, COOH, $OCH_3$, $SCH_3$, SPh, NOH, $NOH(CH_3)$, $SNH_2$, $S(O)NH_2$, $S(O)(O)NH_2$, $CH_3$, Ph.

Wherein each "A" is independently $(CH_2)_x$, CO, CS, S, S(O), S(O)(O), NH, NOH, $NCH_3$, $NR_5$ and Se; where "x" is 1–7 carbon.

Wherein each "B" is independently $(CH_2)_x$, CO, CS, S, S(O), S(O)(O), NH, NOH, $NCH_3$, $NR_5$ and Se; where "x" is 1–7 carbon.

Wherein each "X" is independently $(CH_2)_x$, CO, CS, O, S, S(O), S(O)(O), NH, NOH, $NCH_3$ and $NR_5$; where "x" is 1–7 carbon.

Wherein each "Z" is independently $(CH_2)_x$, CO, CS, S, S(O), S(O)(O), NH, NOH, $NCH_3$ and $NR_5$; where "x" is 1–7 carbon.

$R_5$ is a H, OH, OMe, CN, NH, NOH, $ONCH_3$, $ONH_2$, ethyl, propyl, lower alkyl (1–7C), Me, heteroalkyl (1–7C), aryl(6–7C), —$(CH_2)_xF$; where "x" is 1–7C, and "F" is independently H, OH, SH, $OCH_3$, CN, $SCH_3$, $ONH_2$, ONH $(CH_3)$, $SNH_2$, S(O) $NH_2$, S(O) (O)$NH_2$, $CH_3$, Ph.

Wherein each "V" is independently a phosphodiester analog, phosphorothioates, methylphosphonates, phosphorodithioates, boronphosphonates, selenophosphonates, phosphoramidates and/ or two to four atom long internucleoside linkage is selected from carbon, nitrogen, oxygen, sulfur and selenium. The length of the oligomer varies from dimer to 200 mer. Preferred modified internucleotide linkages include the structures for "V" are shown in Table I.

In other embodiments, the invention provides methods for treating diseases mediated by the presence of a nucleotidseqsequence which comprise administering to a subject in need of such treatment an amount of the above modified oligonucleotides capable of specifically binding the nucleotide sequence effective to inactivate the nucleotide sequence.

In the oligonucleotides of the invention, at least one of the phosphodiester groups included within the "Vs" of Formulae 24–41 is substituted by the modified internucleoside linkages described herein. Desirably, multiple phosphodiester linkages in the unmodified oligonucleotide are substituted by the modified internucleoside linkage may be used repeatedly in this structure, or, if desired, a variety of modified internucleotide linkages may be used in an individual oligonucleotide. In a preferred embodiment of the subject oligonucleotides these substituent linkages are non-chiral so as to enhance the ability of the oligonucleotide to hybridize to a desired target; however, useful compounds of the invention include those embodiments in which chiral forms are used.

Perferred modified internucleotide linkages include the structures for "V" are shown in the Table 1.

TABLE I

—(O)—
—S—
—S(O)—
—S(O)(O)—
—Se—
—Si—
—C(O)—
—C(S)—
—NH—
—NOH—
—NCH$_3$—
—NR$_5$—
—CH$_2$—
—O—CH$_2$—
—CH$_2$—O—
—O—CH$_2$—CH$_2$—
—CH$_2$—CH$_2$—O—
—CH$_2$—O—CH$_2$—
—O—CH$_2$—O—
—S—CH$_2$—
—CH$_2$—S—
—S—CH$_2$—CH$_2$—
—CH$_2$—CH$_2$—S—
—CH$_2$—S—CH$_2$—
—S—CH$_2$—S—
—O—CH$_2$—S—
—S—CH$_2$—O—
—S(O)—CH$_2$—
—CH$_2$—S(O)—
—S(O)—CH$_2$—CH$_2$—
—CH$_2$—CH$_2$—S(O)—
—CH$_2$—S(O)—CH$_2$—
—S(O)—CH$_2$—S(O)—
—O—CH$_2$—S(O)—
—S(O)—CH$_2$—O—
—S(O)(O)—CH$_2$—
—CH$_2$—S(O)(O)—
—S(O)(O)—CH$_2$—CH$_2$—
—CH$_2$—CH$_2$—S(O)(O)—
—CH$_2$—S(O)(O)—CH$_2$—
—S(O)(O)—CH$_2$—S(O)(O)—
—O—CH$_2$—S(O)(O)—
—S(O)(O)—CH$_2$—O—
—S—S—
—S(O)—S(O)—
—S(O)(O)—S(O)—(O)—
—Se—CH$_2$—
—CH$_2$—Se—
—Se—CH$_2$—CH$_2$—
—CH$_2$—CH$_2$—Se—
—CH$_2$—Se—CH$_2$—
—Se—CH$_2$—Se—

TABLE I-continued

—O—CH$_2$—Se—
—Se—CH$_2$—O—
—Se(O)—CH$_2$—
—CH$_2$—Se(O)—
—Se(O)—CH$_2$—CH$_2$—
—CH$_2$—CH$_2$—Se(O)—
—CH$_2$—Se(O)—CH$_2$
—Se(O)—CH$_2$—Se(O)—
—O—CH$_2$—Se(O)—
—Se(O)—CH$_2$—O—
—Se(O)(O)—CH$_2$—
—CH$_2$—Se(O)(O)—
—Se(O)(O)—CH$_2$—CH$_2$—
—CH$_2$—CH$_2$—Se(O)(O)—
—CH$_2$—Se(O)(O)—CH$_2$—
—Se(O)(O)—CH$_2$—Se(O)(O)—
—Se—Se—
—Se(O)—Se(O)—
—Se(O)(O)—Se(O)—(O)—
—O—CH$_2$—Se(O)(O)—
—Se(O)(O)—CH$_2$—O—
—S—CH$_2$—Se—
—Se—CH$_2$—S—
—S(O)—CH$_2$—Se(O)—
—Se(O)—CH$_2$—S(O)—
—S(O)(O)—CH$_2$—Se(O)(O)—
—Se(O)(O)—CH$_2$—S(O)(O)—
—S—S—
—S(O)—S(O)—
—S(O)(O)—S(O)(O)—
—Se—Se—
—Se(O)—Se(O)—
—Se(O)(O)—Se(O)(O)—
—N(R$_5$)—CH$_2$—
—CH$_2$—N(R$_5$)—
—N(R$_5$)—CH$_2$—CH$_2$—
—CH$_2$—CH$_2$—N(R$_5$)—
—CH$_2$—N(R$_5$)—CH$_2$—
—N(R$_5$)—O—
—O—N(R$_5$)—
—N(R$_5$)—O—CH$_2$—
—CH$_2$—O—N(R$_5$)—
—CH$_2$—N(R$_5$)—O—
—O—N(R$_5$)—CH$_2$—
—O—CH$_2$—N(R$_5$)—
—N(R$_5$)—CH$_2$—O—
—N(R$_5$)—S—
—S—N(R$_5$)—
—N(R$_5$)—S—CH$_2$—
—CH$_2$—S—N(R$_5$)—
—CH$_2$—N(R$_5$)—S—
—S—N(R$_5$)—CH$_2$—
—S—CH$_2$—N(R$_5$)—
—N(R$_5$)—CH$_2$—S—
—N(R$_5$)—S(O)—
—S(O)—N(R$_5$)—
—N(R$_5$)—S(O)—CH$_2$—
—CH$_2$—S(O)—N(R$_5$)—
—CH$_2$—N(R$_5$)—S(O)—
—S(O)—N(R$_5$)—CH$_2$—
—S(O)—CH$_2$—N(R$_5$)—
—N(R$_5$)—CH$_2$—S(O)—
—N(R$_5$)—S(O)(O)—
—S(O)(O)—N(R$_5$)—
—N(R$_5$)—S(O)(O)—CH$_2$—
—CH$_2$—S(O)(O)—N(R$_5$)—
—CH$_2$—N(R$_5$)—S(O)(O)—
—S(O)(O)—N(R$_5$)—CH$_2$—
—S(O)(O)—CH$_2$—N(R$_5$)—
—N(R$_5$)—CH$_2$—S(O)(O)—
—O—N(R$_5$)—S—
—S—N(R$_5$)—O—
—O—N(R$_5$)—S(O)—
—S(O)—N(R$_5$)—O—
—O—N(R$_5$)—S(O)(O)—
—S(O)(O)—N(R$_5$)—O—
—O—S—O—
—O—S(O)—O—
—O—S(O)(O)—O—

TABLE I-continued

—N(R$_5$)—S—N(R$_5$)—
—N(R$_5$)—S(O)—N(R$_5$)—
—N(R$_5$)—S(O)(O)—N(R$_5$)—
—CH$_2$—S—O—
—CH$_2$—S(O)—O—
—CH$_2$—S(O)(O)—O—
—CH$_2$—C(O)—O—
—CH$_2$—C(S)—O—
—CH$_2$—N(R$_5$)—C(O)—O—
—CH$_2$—N(R$_5$)—C(S)—O—
—N(R$_5$)—C(O)—O—CH$_2$—
—N(R$_5$)—C(S)—O—CH$_2$—
—O—C(O)—N(R$_5$)—O—
—O—C(S)—N(R$_5$)—O—
—O—C(O)—N(R$_5$)—CH$_2$—
—O—C(S)—N(R$_5$)—CH$_2$—
—O—C(O)—CH$_2$—N(R$_5$)—
—O—C(S)—CH$_2$—N(R$_5$)—
—O—C(O)—CH$_2$—O—N(R$_5$)—
—O—C(S)—CH$_2$—O—N(R$_5$)—
—O—C(O)—N(R$_5$)—O—CH$_2$—
—O—C(S)—N(R$_5$)—O—CH$_2$—
—O—N(R$_5$)—C(O)—O—CH$_2$—
—O—N(R$_5$)—C(S)—O—CH$_2$—
—CH$_2$—O—C(O)—N(R$_5$)—O—
—CH$_2$—O—C(S)—N(R$_5$)—O—
—CH$_2$—O—C(O)—N(R$_5$)—CH$_2$—
—CH$_2$—O—C(S)—N(R$_5$)—CH$_2$—
—CH$_2$—O—C(O)—CH$_2$—N(R$_5$)—
—CH$_2$—O—C(S)—CH$_2$—N(R$_5$)—
—CH$_2$—O—C(O)—N(R$_5$)—
—CH$_2$—O—C(S)—N(R$_5$)—
—CH$_2$—O—C(O)—N(R$_5$)—O—
—CH$_2$—O—C(S)—N(R$_5$)—O—
—CH$_2$—O—N(R$_5$)—C(O)—O—
—CH$_2$—O—N(R$_5$)—C(S)—O—
—CH$_2$—N(R$_5$)—C(O)—S—
—CH$_2$—N(R$_5$)—C(S)—S—
—N(R$_5$)—C(O)—S—CH$_2$—
—N(R$_5$)—C(S)—S—CH$_2$—
—S—C(O)—N(R$_5$)—O—
—O—C(S)—N(R$_5$)—S—
—S—C(O)—N(R$_5$)—CH$_2$—
—S—C(S)—N(R$_5$)—CH$_2$—
—S—C(O)—CH$_2$—N(R$_5$)—
—S—C(S)—CH$_2$—N(R$_5$)—
—S—C(O)—CH$_2$—O—N(R$_5$)—
—O—C(S)—CH$_2$—S—N(R$_5$)—
—O—C(O)—N(R$_5$)—S—CH$_2$—
—S—C(S)—N(R$_5$)—O—CH$_2$—
—S—N(R$_5$)—C(O)—O—CH$_2$—
—O—N(R$_5$)—C(S)—S—CH$_2$—
—CH$_2$—S—C(O)—N(R$_5$)—O—
—CH$_2$—O—C(S)—N(R$_5$)—S—
—CH$_2$—S—C(O)—N(R$_5$)—CH$_2$—
—CH$_2$—S—C(S)—N(R$_5$)—CH$_2$—
—CH$_2$—S—C(O)—CH$_2$—N(R$_5$)—
—CH$_2$—S—C(S)—CH$_2$—N(R$_5$)—
—CH$_2$—S—C(O)—N(R$_5$)—
—CH$_2$—S—C(S)—N(R$_5$)—
—CH$_2$—S—C(O)—N(R$_5$)—O—
—CH$_2$—S—C(S)—N(R$_5$)—O—
—CH$_2$—S—N(R$_5$)—C(O)—O—
—CH$_2$—S—N(R$_5$)—C(S)—O—
—CH$_2$—O—C(O)—N(R$_5$)—S—
—CH$_2$—O—C(S)—N(R$_5$)—S—
—CH$_2$—O—N(R$_5$)—C(O)—S—
—CH$_2$—O—N(R$_5$)—C(S)—S—
—N(R$_5$)—N(R$_5$)—
—N(R$_5$)—N(R$_5$)—CH$_2$—
—CH$_2$—N(R$_5$)—N(R$_5$)—
—N=C(NH$_2$)—N(R$_5$)—
—N(R$_5$)—N=C(NH$_2$)—
—S(O)—CH$_2$—O—
—O—CH$_2$—S(O)—
—S—CH(R$_5$)—O—
—O—CH(R$_5$)—S—
—O—CH$_2$—CH=CH—
—S—CH$_2$—CH=CH—

TABLE I-continued

—S—CH$_2$—C=C—
—N(R$_5$)—CH$_2$—N(R$_5$)—
—N(R$_5$)—C(O)—N(R$_5$)—
—N(R$_5$)—C(S)—N(R$_5$)—
—N(R$_5$)—C(O)—S—
—N(R$_5$)—C(S)—S—
—N(R$_5$)—C(S)—O—
—N(R$_5$)—C(O)—O—
—O—C(O)—N(R$_5$)—
—O—C(S)—N(R$_5$)—
—S—C(O)—N(R$_5$)—
—S—C(S)—N(R$_5$)—

R$_5$ is a H, OH, OMe, CN, NH, NOH, ONCH$_3$, ONH$_2$, ethyl, propyl, lower alkyl (1–7C), Me, heteroalkyl (1–7C), aryl (6–7C), —(CH$_2$)$_x$F; where "x" is 1–7C, and "F" is independently H, OH, SH, OCH$_3$, CN, SCH$_3$, ONH$_2$, ONH (CH$_3$), SNH$_2$, S(O)NH$_2$, S(O) (O)NH$_2$,CH$_3$, Ph. Additionally, conjugate one or more moieties may be joined to the linkage so as to produce an oligomer conjugate. Suitable conjugate moieties include, O-cholesterol, polyethylene glycol, amino acids, intercalulators, cleaving moieties (e.g., imdazole), crosslinking functionalities (e.g., psoralen), lipids, peptides, alkylating agents, hydroxamates, and fluorescent labels.

Particularly preferred 4'-5' linkages include phosphodiester, phosphorothiates, metylphosphonates, carboxamide, thiocarboxamide, hydroxamate, sulfonamide, hydroxylamine and carbamate. The same modifications are preferred for 2'-5' and 3'-5' linkages as well.

The oligomers of the invention are not limited to oligomers of homogeneous linkage type, and that alternating or randomly distributed substitute linkages including the 2', 5' linkages are included. Since the oligomers of the invention can be synthesized one nucleomonomer residue at a time, each individual linkage, and/or substitute linkage, and the nature of each individual "Base" substituent may be selected independently so as to produce oligonucleotides having a desired sequence.

The oligomers of the invention may contain any desired number of the substitute linkages. These substitute linkages may be identical to each other or different by virtue of the embodiments chosen for "V" including other noninvention substitute linkages. Since the oligomers are prepared sequentially, any pattern of linkage or substitute linkage types, bases and sugar modifications may be used.

In preferred embodiments of the invention, the substitute linkages of the invention alternate in a regular pattern. For example, one substitute linkage is followed by two phosphodiester linkages followed by one invention substitute linkage, etc. Additional embodiments include, for example, alternating linkages such as a substitute linkage followed by a phosphodiester analog (e.g., thioate, etc.), followed by a substitute linkage of the invention followed by a phosphodiester analog, etc., i.e., the oligomer of the invention may comprise a one-by-one alternation of the two types of substitute linkages. Oligomers of the invention comprising more than one type of linkage may have any of a number of regular patterns formed by alternations between the different linkage types present between the subunits of the oligomer.

Sugar modifications may be made to one or more nucleomonomer residues in oligomers of the invention; however, 4'-5', 3'-5' and 2'-5' nucleotide linkage between amino acid residues are preferred when such modifications are to be incorporated. Where this is the case, further abbreviation may be used to represent the base sequence of the oligonucleotide analog. For example, in standard DNA (or RNA)

the sequences are generally denoted by the sequence of bases alone, such as, for example, ATG CGC TGA. In general, it is simply stated in advance whether this represents an RNA or DNA sequence. A corresponding notation system is used herein so as to represent oligonucleotide analogs with a given base sequence.

Additional Nucleomonomer Modifications

Oligomers of the invention may also comprise of various modifications in addition to the substitute linkages of the invention. Additional modifications include oligomers where (i) one or more nucleomonomer residues are modified at the 2', 3', 4', and 5' positions, (ii) one or more covalent crosslinking moieties are incorporated, (iii) other noninvention substitute linkages are included, (iv) other base analogs, such as 8-oxo-$N^6$-methyladenine, are included and (v) conjugates such as intercalating agents or polylysine that respectively enhance binding affinity to target nucleic acid sequences or that enhance association of the oligomer with cells are included.

The sequence-specific polynucleotide binding properties of the oligomers of the invention for single-stranded and duplex targets is compatible with further modifications to the oligomer. These further modifications may also confer other useful properties such as stability to nuclease cleavage (e.g. in a domain of an oligomer of the invention having phosphodiester linkages), or enhance their ability to permeate cell membranes, and the like.

The oligomers of the invention may comprise one or more substitute linkages such as sulfide or sulfone linkages (Benner, S. A., International Publication No. WO 89/12060), sulfamate linkages (International Publication No. WO 91/15500), carbamate or other substitute linkages in morpholino-linked oligomers (Stirchak, E. P. et al *Nucleic Acids Rest,* 1989, 17, 6129–6141; Summerton, J., et al International Publication No. 216 860) and related linkages.

Thus, exemplary embodiments of invention oligomers include oligomers having (1) at least one substitute linkage and an amino acid that is linked to an adjacent monomer and (2) one or more non-invention substitute linkages selected from the group consisting of phosphorothioate, methylphosphonate and thionomethylphosphonate and/or (3) one or more phosphodiester linkages and/or (4) purine or pyrimidine analogs that enhance binding affinity for complementary target sequences. Other exemplary oligomers would include (1) an oligomer having invention substitute linkages at the 3' and/or 5' ends and phosphorothioate linkages elsewhere in the oligomer; (2) oligomers having invention substitute linkages and standard purine or pyrimidine bases (e.g. adenine, guanine, cytosine, thymine, or uracil); (3) oligomers having invention substitute linkages and one or more bases that enhance binding affinity or permeation competence of the oligomer (e.g. 5-methylcytosine, 5'(1-propynyl) uracil, 5-(1-propynl) cytosine. Also included are oligomers containing nucleomonomer residues linked via hydroxamates.

Synthesis of Oligomers

The oligomers of the invention may be formed using nucleomonomers of the invention alone or in combination with conventional nucleomonomers and synthesized using standard solid phase (or solution phase) oligomer synthesis techniques, which are now commercially available. In general, the invention oligomers may be synthesized by a method comprising the steps of: synthesizing a nucleomonomer or oligomer synthon having a protecting group and a base and a coupling group capable of coupling to a nucleomonomer or oligomer; coupling the nucleomonomer or oligomer synthon to an acceptor nucleomonomer or an acceptor oligomer; removing the protecting group; and repeating the cycle as needed until the desired oligomer is synthesized.

The oligomers of the present invention may be of any length including those of greater than 40, 50, 100, 200 or 500 nucleomonomers. In general, preferred oligomers contain 2–30 nucleomonomers. Lengths of greater than or equal to about 8 to 20 nucleomonomers may be useful for therapeutic or diagnostic applications provided they have a suitable base sequence. Short oligomers containing 2, 3, 4 or 5 nucleomonomers are specifically included in the present invention and may be used as synthons.

Oligaomers having a randomized sequence and containing about 6, 7 or 8 nucleomonomers may be used as primers that are used in cloning or amplification protocols that use random sequence primers, provided that the oligomer contains about 1 or 2 residues at the 3' end that can serve as a primer for polymerases or reverse transcriptases or that otherwise do not interfere with polymerase activity.

In addition to the linkages described for the first time herein, the oligomers of the invention may comprise conventional phosphodiester linkages or can contain other substitute linkages such as phosphoramidate linkages in addition to the invention substitute linkages. These substitute linkages include, but are not limited to, embodiments wherein a moiety of the formula —O—P(O)(S)—O— ("phosphorothioate"), —O—P(O)(NR$_2^{11}$)—X$^2$, —O—P(O)(R$^{11}$)—O—, —O—P(S)(R$^{11}$)—O— ("thionoalkylphosphonate"), —P(O) (OR$^9$)—X$^2$, —O—C (O)—X$^2$, or —O—C(O) (NR$_2^{11}$)—X$^2$—, wherein R$^{11}$ is H (or a salt) or alkyl (1–12C including methyl and ethyl) and R$^9$ is alkyl (1=9C) and the linkage is joined to adjacent nucleomonomers through an —O— or —S— bonded to a carbon of the nucleomonomer and X$^2$ is O or S. Phosphorothioate and phosphodiester linkages are well known. Particularly preferred substitute linkages for use in the oligomers of the present invention include phosphodiester, phosphorothioate, methylphosphonate and thionomethylphosphonate substitute linkages. Phosphorothioate and methylphosphonate substitute linkages confer added stability to the oligomer need be identical, particularly preferred oligomers of the invention contain one or more phosphorothioate or methylphosphonate substitute linkages.

Oligomers of the invention and the segments thereof may be synthesized using methods that are known to the personof ordinary skill in the art. The synthetic methods known in the area and described herein can be used to synthesize oligomers containing substitute linkages of the invention, as well as other linkages or substitute linkages known in the art, using appropriately protected nucleomonomers. Methods for the synthesis of oligomers having phosphorous containing linkages are found, for example, in Froehler, B., et al., *Nucleic Acids Res.*, 1986, 14, 5399–5467; *Nucleic Acids Res.*, 1988, 16, 4831–4839; *Nucleosides & Nucleotides*, 1987, 6, 287–291; Froehler, B., *Tetrahedron Letts.*, 1986, 27, 5575–5578; Caruthers, M. H. in *Oligodeoxynucleotides Antisense Inhibitions of Gene Expression*, 1989, J. S. Cohen, editor, CRC Press, Boca Raton, p7–24; Reese, C. B. et al, *Tetrahedron Letts.*, 1985, 26, 2245–2248. Synthesis of the methylphosphonate linked oligomers via methyl phosphonamidite chemistry has also been described (Agrawal, S. et al., *Tetrahedron Letts.*, 1987, 28, 3539–3542; Klem, R. E., et al, International Publication Number WO 92/07864).

Oligomers containing linkages of the present invention are also conveniently synthesized by preparation of dimer or trimer compounds by solution phase chemistry followed by conversion of the synthon to a derivative that is incorporated into oligomers by either solid or solution phase chemistry. Typical synthons are 5' DMT or MMT blocked 3' phosphonate or phosphoramidate derivatives which are prepared by standard methods (see: Gait, M. J. ed., Oligonucleotide Synthesis; A Practical Approach 1984, IPL Press, Oxford).

Synthons that are included in the scope of the present invention include dimers, trimers, tetramers, hexamers and longer oligomer made by solid or solution phase synthesis. Trimers and longer synthons may contain more than one type of linkage. The synthons may include any base as described above or 2', 3', 4' and 5' groups such as OH, DMTO, MMTO, O-allyl, phosphate, a phosphonate or an amidite as described above.

Figure 26:
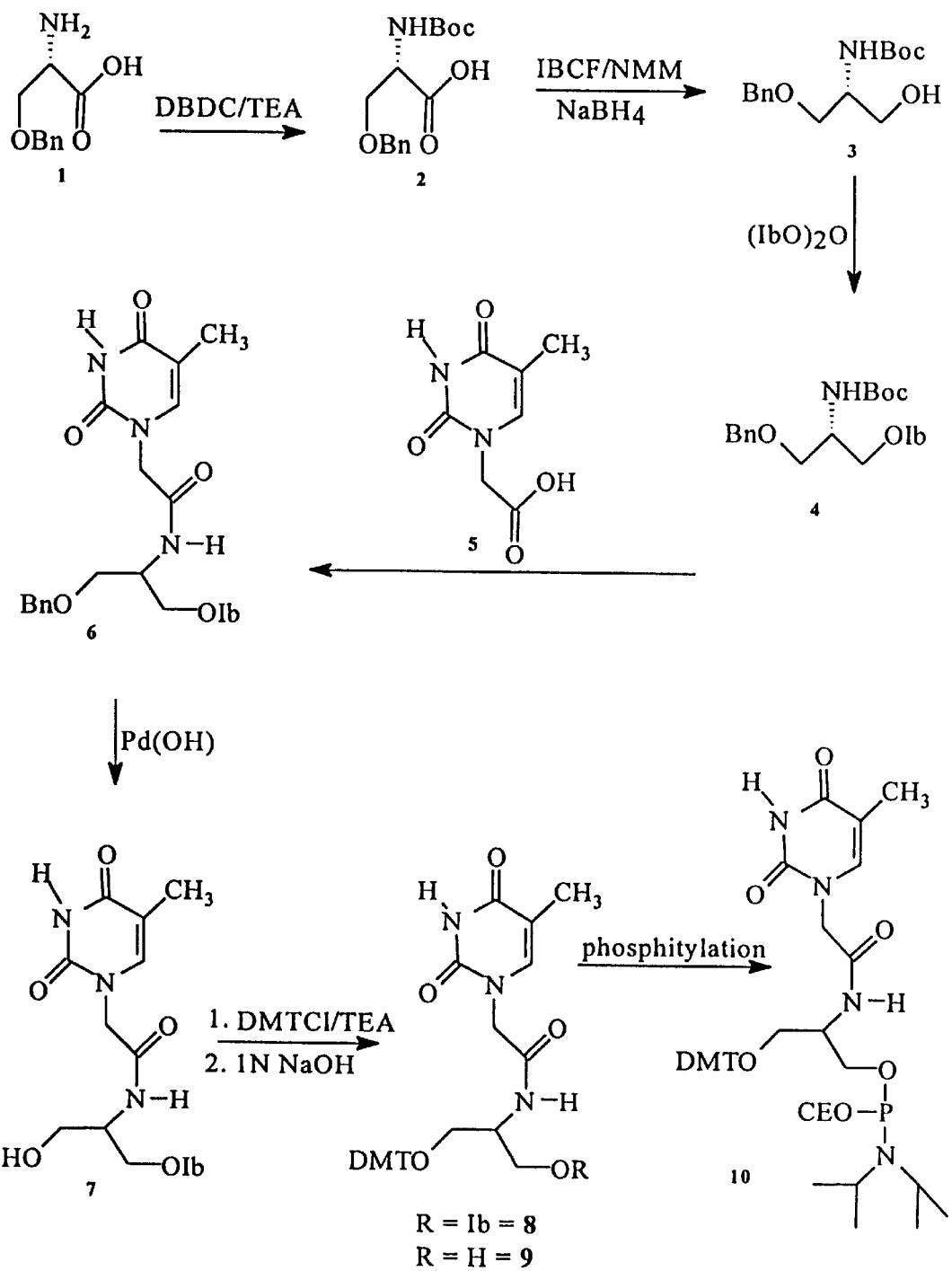
FIG. 26 shows the synthesis of 1-O-(4,4'-Dimethoxytrityl)-2-[amino(thyminylacetyl)]-L-propan-3-O-(N,N-diisopropyl)-β-cyanoethylphosphoramidite.

Ribose-amide oligonucleotides could be synthesized by using standard solid phase peptide synthesis (Fmoc chemistry) conditions (see FIG. 26).

Blocking Groups For the Synthesis of the Compound of the Invention

1. Coupling groups.

Suitable coupling groups are, for example, H-phosphonate, a methylphosphonomidite, or a phosphoramidite. Phosphoramidites that can be used include β-cyanoethylphosphoramidites (preferred). Methylphosphonamidites, alkylphosphonamidites (including ethylphosphonamidites and propylphosphonamidites) can also be used. Exemplary phosphoramidites are shown in FIGS. 1 to 21.

Suitable "coupling groups" at the 2', 3', 4' or 5' position for oligomer synthesis via phosphoramidite triester chemistry, referred to herein as "amidite" chemistry, include N,N-diisopropylamino-β-cyanoethoxyphosphine, N-N, diisopropylamino-methoxyphosphine, N,N-diethylamino—cyanoethoxyphosphine, and (N-morpholino)-methoxyphosphine (Moore, M. F. et al, *J Org Chem.*, 1985, 50, 2019–2025; Uznanski, A. W., et al, *Tetrahedron Letts.*, 1987, 28, 3401–3404; Bjergarde, K., et al, *Nucl Acids Res.*, 1991, 19, 5843–5850; Dahl, O. Sulfur Reports, 1991, 11, 167–192). Related coupling groups such as N,N-diisopropylamino-methyl-phosphine or N,N-diethylamino-methyl-phosphine can also be used to prepare methylphosphonates. Methylphosphonate oligomers can be conveniently synthesized using coupling groups such as N,N-diisopropylamino-methylphosphoramidite. Synthesis of nucleomonomer amidites of the invention can be accomplished by conventional methods (for example, Gryaznov, S. M., et al, *Nucl Acids Res.*, 1992, 20, 1879–1882; Vinayak, R., et al, *Nucl Acids Res.*, 1992, 20, 1265–1269; Sinha, N. D., et al, *Nucl Acids Res.*, 1984, 12, 4539–4557; and other references cited herein).

2. Protecting Groups.

Protecting groups such as diisobutylformamidine, benzoyl, isobutyryl, EMOC, dialkylformamidine, dialkylacetamidine or other groups known in the art can be used to protect the exocyclic nitrogen of the cytosine, adenine or guanine heterocycles. Alternatively, cytidine can be directly incorporated into oligomers without a protecting group at the exocyclic nitrogen using described methods (Gryaznov, S. M. et al, *J Amer Chem Soc.*, 1991, 113, 5876–5877; Gryaznov, S. M. et al, *Nucl Acids Res.*, 1992, 20, 1879–1882; Kung, P. -P. et al, *Tetrahedron Letts.*, 1992, 33, 5869–5872).

Suitable protecting groups are DMT (dimethoxy trityl), Bz (benzoyl), Bu (isobutyryl), phenoxyacetyl, MMT (monomethoxytrityl) or FMOC at the 5' terminus and/or hydrogen phosphonate, methyl phosphoramidite, methyl phosphonamidite, β-cyanoethylphosphoramidite, TBS (t-butyldimethylsilyl) or TBDPS (t-butyldiphenylsilyl) at the 3'-terminus.

Preferred protecting groups are Bz (benzoyl), DMT (dimethoxytrityl), MMT (monomethoxytrityl) or FMOC at the 5' terminus or position and/or TBS, hydrogen phosphonate, methylphosphoramidite, methyl-phosphonamidite, β-cyanoethylphosphoramidite at the 3'-terminus. However, it is intended that the position of the blocking groups can be reversed as needed (e.g., a phosphoramidite at the 5' position and DMT at the 3'-position). In general, the nucleomonomers and oligomers of the invention can be derivatized to such "blocking groups" as indicated in the relevant formulas by methods known in the art.

Conjugates

The subject invention also provides for "conjugates" of the oligomers of the invention. "Conjugates" of conventional oligomers are known to the person of ordinary skill in the art. For example, the oligomers of the invention may be covalently linked to various moieties such as, for example, intercalators, and compounds which interact specifically with the minor groove of the DNA double helix. Other moieties for conjugation to the subject oligomers include, labels, (e.g., radioactive, fluorescent, enzyme) or moieties which facilitate cell association using cleavable linkers and the like. Suitable radiolabels include $^{32}P$, $^{35}S$, $^{3}H$, $^{131}I$ and $^{14}C$; and suitable fluorescent labels include fluorescence, resorufin, rhodamine, BODIPY (Molecular Probes) and Texas red; suitable enzymes include alkaline phosphatase and horseradish peroxidase. Other compounds which can be used as covalently linked moieties include biotin, antibodies or antibody fragments, asialoglycoprotein, transferrin and the HIV Tat protein can also conveniently be linked to the oligomers of the invention.

These additional moieties can be derivatized through any convenient moiety. For example, intercalators, such as acridine or psoralen can be linked to the oligomers of the invention through any available —OH or —SH, e.g., at the terminal 5'-position of the oligomer, the 2'-positions of RNA, or an OH, $NH_2$, COOH or SH incorporated into the 5-position of pyrimidines. A derivatized form which contains, for example, —$CH_2CH_2CH_2$, OH or —$CH_2CH_2CH_2SH$ in the 5-position of pyrimidines is convenient. Conjugates including polylysine or lysine can be synthesized as described and can further enhance the binding affinity of an oligomer to its target nucleic acid sequence (Lemaitre, M. et al., Proc Natl Acad Sci. USA, 1987, 84, 648–652; Lemaitre, M. et al., *Nucleosides and Nucleotides*, 1987, 6, 311–315).

A wide variety of substituents can be attached, including those bound through linkages or substitute linkages. The —OH moieties in the oligomers can be replaced by phosphate groups, protected by standard protecting groups, or coupling groups to prepare additional linkages to other nucleomonomers, or can be bound to the conjugated substituent. The 5'-terminal OH can be phosphorylated; the 2'—OH or OH substituents at the 3'-terminus can also be phosphorylated. The hydroxyls can also be derivatized to standard protecting groups.

Oligomers of the invention can be covalently derivatized to moieties that facilitate cell association using cleavable linkers. Suitable conjugates also include solid supports for oligomer synthesis and to facilitate detection of nucleic acid sequences. Solid supports include, but are not limited to, silica gel, controlled pore glass, polystyrene, and magnetic glass beads.

Sugar Modifications

Derivatives can be made by substitution on the sugars. Among the preferred derivatives of the oligomers of the invention are the 2'-O-allyl or 3'-allyl group appears to enhance permeation ability and stability to nuclease degradation, but does not appear to diminish the affinity of the oligomer for single chain or duplex targets. In particular, in ribose-amide backbone oligonucleotides, different functionalities could be introduced at the 1', 2', 3', 4' and 5' positions of the ribose moiety to improve the pharmacokinetic properties of the corresponding oligonucleotides.

Substitute Linkages

The oligomers of the invention may also contain one or more "substitute linkages", in addition to the 2'-5', 3'-5' and 4'-5' linkages disclosed herein, which are generally understood in the art. These "substitute linkages" include phosphorothioate, methylphosphonate, thionomethylphosphonate, phosphorodithioate, alkylphosphonates, morpholino sulfamide, boranophosphate (—O—P(OCH$_3$) (BH$_3$)—O—), siloxane (—O—Si(X$^4$)(X$^4$)—O—; X$^4$ is 1–6C alkyl or phenyl) and phosphoramidate (methoxyethylamine (—O—P (OCH$_2$CH$_2$OCH$_3$) (O)—O—) and the like), and are synthesized as described in the generally available literature including the following references (Sood, A., et al *J. Am. Chem. Soc.*, 1990, 112, 9000–9001; WO 91/08213; WO 90/15065; WO 91/15500; Stirchak, E. P. et al *Nucleic Acid Res.*, 1989, 17, 6129–6141; U.S. Pat. No. 5,034,506; U.S. Pat. No. 5,142,047; Hewitt, J. M. et al, *Nucleosides & Nucleotides*, 1992, 11, 1661–1666; Summerton, J. et al International Publication No. 216 860). Substitute linkages that can be used in the oligomers disclosed herein also include the sulfonamide (—O—SO$_2$—NH—), sulfide (—CH$_2$—S—CH$_2$—), sulfonate (—O—SO$_2$—CH—). carbamate (O—C(O)—NH—, —NH—C(O)—O—), dimethylhydrazino (—CH$_2$—NCH$_3$—), sulfamate (—O—S(O) (O)—N—; —N—S(O)(O)—N—), 3'-amine (—NH—CH$_2$—, N-methylhydroxylamine (—CH$_2$—NCH$_3$—O—) and 2', 5' linkages (such as 2', 5' carbamate (2'—N(H)—C(O)—O—5'), 5', 2' carbamate (2'—O—C(O)—N(H)—5'), 5',2' methylcarbamate (2'—O—C(O)—N(CH$_3$)—5') and 5',2' thioformacetal (2'—O—CH$_2$—S—5'). Additional substitute linkages that are suitable include amide linkages described by Buchardt, O. et al, (International Publication No. WO 92/20702), and those described by Cook, P. D. et al, (International Publication No. WO 92/20822), De Mesmaeker, A. et al., (International Publication No. WO 92/20823) and as described in PCT/US92/04294.

Except where specifically indicated, the substitute linkages, such as a formacetal linkage, —O—CH$_2$—O—, are linked to either the 4', 3', 2' carbon of a nucleomonomer on the left side and to the 5' carbon of a nucleomonomer on the right side. The designations of a 4', 3', 2' or 5' carbon can be modified accordingly when a structure other than ribose, deoxyribose or arabinose is linked to an adjacent nucleomonomer. Such structures include xylose, a hexose, morpholino ring, carbocyclic ring (e.g. cyclopentane) and the like.

The use of carbamate, carbonate, sulfide, sulfoxide, sulfone, N-methylhydroxylamine and dimethylhydrazino linkages in synthons or oligomers has been described (Vaseur, J-J. et al, *J Amer Chem Soc.*, 1992, 114, 4006–4007; WO 89/12060; Musicki, B. et al, *J Org Chem.*, 1990, 55, 4231–4233; Reynolds, R. C. etal., *J Org Chem.*, 1992, 57, 2983–2985; Mertes, M. P., et al, *J Med. Chem.*, 1969, 12, 154–157; Mungall, W. S., et al, *J. Org. Chem.*, 1977, 42, 703–706; Stirchak, E. P., et al, *J. Org. Chem.*, 1987, 52, 4202–4206; Wang, H., et al, *Tetrahedron Letts.*, 1991, 32, 7385–7388; International Application No. PCT US91/03680). Substitute linkage(s) can be utilized in the oligomers for a number of purposes such as to further facilitate binding with complementary target nucleic acid sequences and/or to increase the stability of the oligomers toward nucleases.

Bases

Suitable bases for use as nucleoside bases in the compounds of the invnetion include not only the naturally occurring purine and pyrimidine bases, but also analogs of these heterocyclic bases and tautomers thereof. Such analogs include alkylated purines or pyrimidines, acylated purines or pyrimidines, or other heterocycles. Such "analogous purines" and "analogous pyrimidines" or purine or pyrimidine analogs are those generally known in the art, some of which are used as chemotherapeutic agents. An exemplary, but not exhaustive, list includes N$^4$N$^4$-ethanocytosine, 7-deazaxanthosine, 7-deazaguanosine, 8-oxo-N$^6$-methyladenine, 4-acetylcytosine, 5-(carboxyhydroxylmethyl) uracil, 5-fluorouracil, 5-bromouracil, 5-carboxymethylaminomethyl-2-thiouracil, 5-carboxymethylaminomethyl uracil, inosine, N$^6$-isopentenyladenine, 1-methyladenine, 2-methylguanine, 5-methylcytosine, N$^6$-methyladenine, 7-methylguanine, 5-methylaminomethyl uracil, 5-methoxy aminomethyl-2-thiouracil, 2-thiouracil, 4-thiouracil, 5-(1-propynyl)-4-thiouracil, 5-(1-propynyl)-2-thiouracil, 5-(1-propynyl)-2-thiocytosine, 2-thiocytosine, and 2,6-diaminopurine. In addition to these base analogs, pyrimidine analogs including 6-azacytosine, 6-azathymidine and 5-trifluoromethyluracil described in Cook, D. P., et al, International Publication No. WO 92/02258 can be conveniently incorporated into the invention oligomers.

Incorporation of 4-thiouridine and 2-thiothymidine into oligomers has been described (Nikiforov, T. T. et al, *Tetrahedron Letts.*, 1992, 33, 2379–2382; Clivio, P., et al *Tetrahedron Letts.*, 1992 33:65–68; Nikiforov, T. T., et al, *Tetrahedron Letts.*, 1991 32:2505–2508; Xu, Y. -Z., et al *Tetrahedron Letts.*, 1991 32:2817–2820; Clivio, P., et al *Tetrahedron Letts.*, 1992 33:69–72; Connolly, B. A., et al., *Nucl. Acids Res.*, 1989 17:4957–4974). Preferred bases include adenine, guanine, thymine, uracil, cytosine, 5-methylcytosine, 5-(1-propynyl) uracil, cytosine, 5-methylcytosine, 5-(1-propynyl) uracil, 5-(1-propynyl) cytosine, 8-oxo-N$^6$-methyladenine, 7-deaza-7-methylguanine, 7-deaza-7-methyladenine and 7-deazaxanthosine.

Covalent Bondinc Moiety

Included in some of the oligomers of the invention is a moiety which is capable of effecting at least one covalent bond between the oligomer and the duplex. Multiple covalent bonds can also be formed by providing a multiplicity of such crosslinking moieties. The covalent bond is preferably to a base residue in the target strand, but can also be made with other portions of the target, including the saccharide or phosphodiester. The reaction nature of the moiety which effects crosslinking determines the nature of the target in the duplex. Preferred crosslinking moieties include acylating and alkylating agents, and, in particular, those positioned relative to the sequence specificity-conferring portion so as to permit reaction with the target location in the strand.

It is clear that the heterocycle need not be a purine or pyrimidine; indeed the pseudo-base to which the reactive function is attached need not be a heterocycle at all. Any means of attaching the reactive group is satisfactory so long as the positioning is correct.

Polarity of Oligomers

In their most general form, the symbol 3'–5' indicates a stretch of oligomer in which the linkages are consistently formed between the 5'-hydroxyl of the amino acid residue of the nucleomonomer to the left with the 3'- (or 2'- for oligomers having 2'-5' linkages, or 4' for oligomers having 4'-5' linkages) hydroxyl of the amino acid residue of the nucleomonomer to the right (i.e., a region of uniform polarity), thus leaving the 5'-hydroxynucleomonomer amst nucleomonomer amino acid residue free for additional conjugation. Analogously, 5'–3' indicates a stretch of oligomer in the opposite orientation wherein the linkages are formed between the 3'-hydroxyl of the amino acid residue of the left nucleomonomer and the 5'-hydroxyl of the amino acid residue of the nucleomonomer on the right, thus leaving the 3'-hydroxyl of the rightmost nucleomonomer residue free for additional conjugation. The same thing is true for 5'–4' stretch of oligomers.

Pharmaceutically Acceptable Salts

The invention also provides for various salts of all compounds disclosed herein, including pharmaceutically acceptable salts for administration to an animal or human. Pharmaceutically acceptable salts and such salt forming materials are well known in the art. Pharmaceutically acceptable salts are preferably metal or ammonium salts of the oligomers of the invention and include alkali or alkaline earth metal salts, e.g., the sodium. potassium, magnesium or calcium salt; or advantageously easily crystallizing ammonium salts derived from ammonia or organic amines, such as mono-, di- or tri-lower (alkyl, cycloalkyl or hydroxyalkyl)-amides, lower alkylenediamines or lower (hydroxyalkyl or arylalkyl)alkylammonium bases, e.g. methylamine, diethylamine, triethylamine, dicyclohexylamine, triethanolamine, ethylenediamine, tris-(hydroxymethyl)-aminomethane or benzyltrimethylammonium hydroxide. The oligomers of the invention may form acid addition salts, preferably of therapeutically acceptable inorganic or organic acids, such as strong mineral acids, for example hydrophilic, e.g., hydrochloric or hydrobromic acid; sulfuric, phosphoric; aliphatic or aromatic carboxylic or sulfonic acids, e.g., formic, acetic, propionic, succinic, glycollic, lactic, malic, tartaric, gluconic, citric, ascorbic, maleic, fumaric, hydroxymaleic, pyruvic, phenylacetic, benzoic, 4-aminobenzoic, anthranilic, 4-hydroxynbenzoic, salicylic, 4-aminosalicylic, methanesulfonic, ethanesulfonic, hydroxyethanesulfonic, benzenesulfonic, sulfanilic or cyclohexylsulfamic acid and the like.

Utility and Administration

As the oligomers of the invention are capable of significant single-stranded or double-stranded target nucleic acid binding activity to form duplexes, triplexes or other forms of stable association, with naturally occurring polynucleotides and structural analogs thereof, the oligomers of the invention may be used in most procedures that employ conventional oligomers. Thus, the oligomers of the invention may be used as, for example, polynucleotide hybridization probes, primers for the polymerase chain reaction and similar cyclic amplification reactions, sequencing primers, and the like. The oligomers of the invention may also be used in the diagnosis and therapy of diseases. Therapeutic applications of the oligomers of the invention include the specific inhibition of the expression of genes (or inhibit translation of RNA sequences encoded by those genes) that are associated with either the establishment or the maintenance of a pathological condition through the use of antisense oligomers. The oligomers of the invention may be used to mediate antisense inhibition of numerous genetic targets. Exemplary genes or RNAs encoded by those genes that can be targeted through antisense employing the oligomers include those that encode enzymes, hormones, serum proteins, transmembrane proteins, adhesion molecules (LFA-1, GPII$_b$/III$_a$, ELAM-1, VACM-1, ICAM-1, E-selection, and the like), receptor molecules including cytokine receptors, cytokines (IL-1, IL-2, IL-3, IL-4, IL-6 and the like), oncogenes, growth factors, and interleukins. Target genes or RNAs can be associated with any pathological condition such as those associated with inflammatory conditions, cardiovascular disorders, immune reactions, cancer, viral infections, bacterial infections, yeast infections, parasite infections and the like.

Oligomers of the present invention are suitable for use in both in vivo and ex vivo therapeutic applications. Indications for ex vivo uses include treatment of cells such as bone marrow or peripheral blood in conditions such as leukemia (chronic myelogenous leukemia, acute lymphocytic leukemia) or viral infection. Target genes or RNAs encoded by those genes that can serve as targets for cancer treatments include oncogens, such as ras, k-ras, bcl-2, c-myb, bcr, c-myc c-abl or overexpressed sequences such as mdm2, oncostatin M, IL-6 (Kaposi's sarcoma), HER-2 and translocations such as bcr-abl. Viral gene sequences or RNAs encoded by those genes such as polymerase or reverse transcriptase genes of herpesviruses such as CMV, HSV-1, HSV-2, retroviruses such as HTLV-1, HIV-1, HIV-2, or other DNA or RNA viruses such as HBV, HPV, VZV, influenza virus, adenoviruses, flaviviruses, rhinovirus and the like are also suitable targets. Application of specifically binding oligomers can be used in conjunction with other therapeutic treatments. Other therapeutic uses for oligomers of the invention include (1) modulation of inflammatory responses by modulating expression of genes such as IL-1 receptor, IL-1, ICAM-1 or E-Selection that play a role in mediating inflammation and (2) modulation of cellular proliferation in conditions such as arterial occlusion (restenosis) after angioplasty by modulating the expression of (a) growth or mitogenic factors such as nonmuscle myosin, myc, fox, PCNA, PDGF or FGF or their receptors, or (b) cell proliferation factors such as c-myb. Other suitable proliferation factors or signal transduction factors such as TGFx, IL-6, gINF, protein kinase C, tyrosine kinases (such as p210, p190), may be targeted for treatment of psoriasis or other conditions. In addition, EGF receptor, TGFa or MHC alleles may be targeted in autoimmune diseases.

Delivery of oligomers of the invention into cells can be enhanced by any suitable method including calcium phosphate, DMSO, glycerol or dextran transfection, electroporation or by the use of cationic anionic and/or neutral lipid compositions or liposomes by methods described (International Publications Nos. WO 90/14074, WO 91/16024, WO 91/17424, U.S. Pat. No. 4,897,355). The oligomers can be introduced into cells by complexion with cationic lipids such as DOTMA (which may or may not form liposomes) which complex is then contacted with the cells. Suitable cationic lipids include but are not limited to N-(2, 3-di(9-(Z)-octadecenyloxyl))-prop-1-yl-N,N,N-trimethylammonium (DOTMA) and its salts, 1-O-oleyl-2-O-oleyl-3-dimethylaminopropyl-β-hydroxyethylammonium and its salts and 2,2-bis (oleyloxy)-3-(trimethylammonio) propane and its salts.

Enhanced delivery of the invention oligomers can also be mediated by the use of (i) viruses such as Sendai virus (Bartzatt, R., *Biotechnol Appl Biochem.*, 1989, 11, 133–135) or adenovirus (Wagner, E. et al, *Proc Natl Acad Sci. USA*, 1992, 89, 6099–6013); (ii) polyamine or polycation conjugates using compounds such as polylysine, protamine or Na, N$_{12}$-bis (ethyl)spermine (Wagner, E. et al, *Proc Natl Acad Sci. USA*, 1991, 88, 4255–4259; Zenke, M. et al, *Proc. Natl. Acad. Sci. USA*, 1990, 87, 3655–3659; Chank, B. K. et al,

*Biochem Biophys Res Commun.*, 1988, 157, 264–270; U.S. Pat. No. 5,138,045); (iii) lipopolyamine complexes using compounds such as lipospermine (Behr, J. -P. et al, *Proc Natl Acad Sci. USA*, 1989, 86, 6982–6986; Loeffler, J. P. et al, *J. Neurochem.*, 1990, 54, 1812–1815); (iv) anionic, neutral or pH sensitive lipids using compounds including anionic phospholipids such as phosphatidyl glycerol, cardiolipin, phosphatidic acid or phosphatidylethanolamine (Lee, K. -D. et al, *Biochem Biophys ACTA*, 1992, 1103, 185–197; Cheddar, G. et al, *Arch Biochem Biophys*, 1992, 294, 188–192; Yoshimura, T., et al, *Biochem Int.*, 1990, 20, 697–706); (v) conjugates with compounds such as transferrin or biotin or (vi) conjugates with proteins (including albumin or antibodies), glycoproteins or polymers (including polyethylene glycol) that enhance pharmacokinetic properties of oligomers in a subject. As used herein, transfection refers to any method that is suitable for delivery of oligomers into cells. Any reagent such as a lipid or any agent such as a virus that can be used in transfection protocols is collectively referred to herein as a "permeation enhancing agent". Delivery of the oligomers into cells can be via cotransfection with other nucleic acids such as (i) expressable DNA fragments encoding a protein(s) or a protein fragment or (ii) translatable RNAs that encode a protein(s) or a protein fragment.

The oligomers of the invention can thus be incorporated into any suitable formulation that enhances delivery of the oligomers into cells. Suitable pharmaceutical formulations also include those commonly used in applications where compounds are delivered into cells or tissues by topical administration. Compounds such as polyethylene glycol, propylene glycol, azone, nonoxonyl-9, oleic acid, DMSO, polyamines or lipopolyamines can be used in topical preparations that contain the oligomers.

The invention oligomers can be conveniently used as reagents for research or production purposes where inhibition of gene expression is desired. There are currently very few reagents available that efficiently and specifically inhibit the expression of a target gene by any mechanism. Oligomers that have been previously reported to inhibit target gene expression frequently have nonspecific effects and; or do not reduce target gene expression to very low levels (less than about 40% of uninhibited levels).

Thus, the oligomers as described herein constitute a reagent that may be used in methods of inhibiting expression of a selected protein or proteins in a subject or in cells wherein the proteins are encoded by DNA sequences and the proteins are translated from RNA sequences, comprising the steps of: introducing an oligomer of the invention into the cells; and permitting the oligomer to form a triplex with the DNA or RNA or a duplex with the DNA or RNA whereby expression of the protein or proteins is inhibited. The methods and compound of the present invention are suitable for modulating gene expression in both procaryotic and eucaryotic cells such as bacterial, fungal parasite, yeast and mammalian cells.

RNase H "competent" or RNase H "incompetent" oligomers can be easily designed using the substitute linkages of the invention. RNase H competent oligomers can comprise one or more RNase H competent domains comprised of linked RNase H competent nucleomonomers. Oligomers having modifications such as 2'-substitutions (2'-O-allyl and the like) or certain uncharged linkages (methylphosphonate, phosphoramidate and the like) are usually incompetent as a substrate that is recognized by and/or acted on by RNase H. RNase H competence can facilitate antisense oligomer function by degrading the target RNA in an RNA-oligomer duplex (Dagle, J. M. et al, *Nucl Acids Res.*, 1990, 18, 4751–4757; Walder, J. A. et al, International Publication Number WO 89/05358). The enzyme cleaves RNA in RNA-DNA duplexes.

In order to retain RNase H competence, an oligomer requires a RNase H competent domain of three or more competent contiguous nucleomonomers located within it (Quartin, R. S., et al, *Nucl Acids Res.*, 1989, 17, 7253–7262). Design of oligomers resistant to nuclease digestion will have terminal linkage, sugar and/or base modifications to effect nuclease resistance. Thus, the oligomers can be designed to have modified nucleomonomer residues at either or both the 5'- and/or 3'- ends, while having an internal RNase H competent domain. Exemplary oligomers that retain RNase H competence would generally have uniform polarity and would comprise about 2 to about 12 nucleomonomers at the 5'- end and at the 3'- end which stabilize the oligomer to nuclease degradation and about three to about 26 nucleomonomers that function as a RNase H competent domain between the RNase H incompetent 3' and 5'- ends. Variations on such an oligomer would include (1) a shorter RNase H competent domain comprising 1 or 2 RNase H competent linkages or substitute linkages, (2) a longer RNase H incompetent domain comprising up to 15, 20 or more substitute linkages or nucleomonomers, (3) a longer RNase H competent domain comprising up to 30, 40 or more linkages, (4) oligomers with only a single RNase H incompetent domain at the 3' end or at the 5' end.

Oligomers containing as few as about 8 nucleomonomers may be used to effect inhibition of target protein(s) expression by formation of duplex or triplex structures with target nucleic acid sequences. However, linear oligomers used to inhibit target protein expression via duplex or triplex formation will preferably have from about 10 to about 20 nucleomonomer residues.

Oligomers containing substitute linkages of the invention can be conveniently circularized as described (International Publication No. WO 92/19732; Kool, E. T. *J Am Chem Soc.*, 1991, 113, 6265–6266; Prakash, G. et al, *J Am Chem Soc.*, 1992, 114, 3523–3527). Such oligomers are suitable for binding to single-stranded or double stranded nucleic acid targets. Circular oligomers can be of various sizes. Such oligomers in a size range of about 22–50 nucleomonomers can be conveniently prepared. The circular oligomers can have from about three to about six nucleomonomer residues in the loop region that separate binding domains of the oligomer as described (Prakash, G. ibid). Oligomers can be enzymatically circularized through a terminal phosphate by ligase or by chemical means via linkage through the 5'- and 3'- terminal sugars and/or bases.

The oligomers can be utilized to modulate target gene expression by inhibiting the interaction of nucleic acid binding proteins responsible for modulating transcription (Maher, L. J., et al, *Science*, 1989, 245, 725–730) or translation. The oligomers are thus suitable as sequencespecific agents that compete with nucleic acid binding proteins (including ribosomes, RNA polymerases, DNA polymerases, translational initiation factors, transcription factors that either increase or decrease transcription, protein-hormone transcription factors and the like). Appropriately designed oligomers can thus be used to increase target protein synthesis through mechanisms such as binding to or near a regulatory site that transcription factors use to repress expression or by inhibiting the expression of a selected repressor protein itself.

The invention oligomers, comprising additional modifications that enhance binding affinity can be designed to contain secondary or tertiary structures, such as pseudoknots or pseudo-half-knots (Ecker, D. J. et al, *Science*, 1992, 257, 958–961). Such structures can have a more stable secondary or tertiary structure than corresponding unmodified oligomers. The enhanced stability of such structures would rely on the increased binding affinity between regions of self complementary in a single oligomer or regions of complementary between two or more oligomers that form a given structure. Such structures can be used to mimic structures such as the HIV TAR structure in order to interfere with binding by the HIV Tat protein (a protein that binds to TAR). A similar approach can be utilized with other transcription or translation factors that recognize higher nucleic acid structures such as stems, loops, hairpins, knots and the like. Alternatively, the invention oligomers can be used to (1) disrupt or (2) bind to such structures as a method to (1) interfere with or (2) enhance the binding of proteins to nucleic acid structures.

In addition to their use in antisense or triple helix therapies, the oligomers of the invention can also be applied as therapeutic or diagnostic agents that function by direct displacement of one strand in a duplex nucleic acid. Displacement of a strand in a natural duplex such as chromosomal DNA or duplex viral DNA, RNA or hybrid DNA/RNA is possible for oligomers with a high binding affinity for their complementary sequence is not great enough to efficiently displace a DNA or RNA strand in a duplex. Therapeutic efficacy of oligomers that function by D-looping would result from high affinity binding to a complementary sequence that results in modulation of the normal biological function associated with the nucleic acid target. Types of target nucleic acids include but are not limited to (i) gene sequences including exons, introns, exon/intron junctions, promoter/enhancer regions and 5' or 3' untranslated regions, (ii) regions of nucleic acids that utilize secondary structure in order too function (e.g. the HIV TAR stem-loop element or tRNAs), (iii) nucleic acids that serve structural or other functions such as telomeres, centromeres or replication origins (virus, bacteria and the like) and (iv) any other duplex region. It is clear that oligomers can be synthesized with discrete functional domains wherein one region of an oligomer binds to a target by D-looping while an adjacent region binds a target molecule by say, forming a triple helix or binding as an aptamer to a protein. Alternatively, a D-looping looping oligomer can bind to each strand in a duplex by switching the strand to which the oligomer binds (i.e. by having one region of the oligomer that binds to one strand and another region that binds to the complementary strand). The controlling elements that dictate the mode of binding (i.e. triple helix or D0loop) are the sequence of the oligomer and the inherent affinity built into the oligomer. Base recognition rules in Watson-Crick duplex binding differ from those in Hoogsteen controlled triplex binding. Because of this, the oligomer base sequence can be used to dictate the type of binding rules an oligomer will utilize. D-loop structures are formed in nature by enzyme-mediated processes (Harris, L. D. et al., et al., *J Biol Chem.*, 1987, 262, 9285–9292) or are associated with regions where DNA replication occurs (Jacobs, H. T. et al., *Nucl Acids Res*, 1989, 17, 8949–8966). D-loops that arise from the binding of oligomers can result from a one or two step process. Direct displacement of a target strand will give rise to a D-loop by a single binding event. However, D-looping can also occur by forming a triple helix which facilitates a strand displacement envent leading to the D-loop.

Ribozymes containing substitute linkages of the invention can be designed in order to design species with altered characteristics. Ribozymes that cleave single stranded RNA or DNA (Robertson, D. L., et al., *Nature*, 1990, 344, 467–468) have been described. Therapeutic applications for ribozymes have been postulated (Sarver, N. et al., *Science*, 1990, 247, 1222–1225; International Publication Number WO 91/04319). Secondary or tertiary structure necessary for ribozyme function can be affected by design of appropriate oligomer sequences. For example, ribozymes having nuclease stable targeting domains containing substitute linkages of the invention can have higher affinity, while maintaining base pairing specificity, for target sequences. Because of the higher affinity and/or nuclease stability of the invention substitute linkages shorter recognition domains in a ribozyme (an advantage in manufacturing) can be designed which can lead to more favorable substrate turnover (an advantage in ribozyme function).

In therapeutic applications, the oligomers of the invention may be utilized in a manner appropriate for treatment of a variety of conditions by inhibiting expression of appropriate target genes. For such therapy, the oligomers can be formulated for a variety of modes of administration, including systemic, topical or localized administration. Techniques and formulations generally can be found in *Reminaton's Pharmaceutical Sciences*, Merck Publishing Co., Easton, Pa., latest edition. The oligomer active ingredient is generally combined with a carrier such as a diluent or excipient which can include fillers, extenders, binders, wetting agents, disintegrants, surface-active agents, or lubricants, depending on the nature of the mode of administration and dosage forms. Typical dosage forms include tablets, powders, liquid preparations including suspensions, emulsions and solutions, granules, capsules and suppositories, as well as liquid preparations for injections, including liposome preparations.

For systemic administration, injection is preferred, including intramuscular, intravenous, intraperitoneal, and subcutaneous. For injection, the oligomers of the invention are formulated in liquid solutions, preferably in physiologically compatible buffers such as Hank's solution or Ringer's solution. In addition, the oligomers can be formulated in solid form and redissolved or suspended immediately prior to use. Lyophilized forms are also included. Dosages that can be used for systemic administration preferably range from about 0.01 mg/Kg to 50 mg/Kg administered once or twice per day. However, different dosing schedules can be utilized depending on (i) the potency of an individual oligomer at inhibiting the activity of its target DNA or RNA, (ii) the severity or extent of a pathological disease state associated with a given target gene, or (iii) the pharmacokinetic behavior of a given oligomer.

Systemic administration can also be by transmucosal or transdermal means, or the compounds can be administered orally. For transmucosal or transdermal administration, penetrates appropriate to the barrier to be permeated are used in the formulation. Such penetrates are generally known in the art, and include, for example, bile salts and fusidic acid derivatives for transmucosal administration. In addition, detergents can be used to facilitate permeation. Transmucosal administration can be through use of nasal sprays, for example, or suppositories. For oral administration, the oligomers are formulated into conventional oral administration forms such as capsules, tablets, and tonics.

For topical administration, the oligomers of the invention are formulated into ointments, salves, gels, or creams, as is generally known in the art. Formulation of the invention oligomers for ocular indications such as viral infections would be based on standard compositions known in the art.

In addition to use in therapy, the oligomers of the invention can be used as diagnostic reagents to detect the presence or absence of the target nucleic acid sequences to which they specifically bind. The enhanced binding affinity of the invention oligomers is an advantage for their use as primers and probes. Diagnostic tests can be conducted by hybridization through either double or triple helix formation which is then detected by conventional means. For example, the oligomers can be labeled using radioactive, fluorescent, or chromogenic labels and the presence of label bound to solid support detected. Alternatively, the presence of a double or triple helix can be detected by antibodies which specifically recognize these forms. Means for conducting assays using such oligomers as probes are generally known.

The use of oligomers of the invention substitute linkages as diagnostic agents by triple helix formation is advantageous since triple helices form under mild conditions and the assays can thus be carried out without subjecting test specimens too harsh conditions. Diagnostic assays based on detection of RNA for identification of bacteria, fungi or protozoa sequences often required isolation of RNA from samples or organisms grown in the laboratory, which is laborious and time consuming, as RNA is extremely sensitive to ubiquitous nucleases.

The oligomer probes can also incorporate additional modifications such as modified sugars and/or substitute linkages that render the oligomer especially nuclease stable, and would thus be useful for assays conducted in the he presence of cell or tissue extracts which normally contain nuclease activity. Oligomers containing terminal modifications often retain their capacity to bind to complimentary sequences without loss of specificity (Uhlmann et al., *Chemical Reviews*, 1990, 90, 543–584). As set forth above, the invention probes can also contain linkers that permit specific binding to alternate DNA strands by incorporating a linker that permits such binding (Froehler, B. C. et al., *Biochemistry*, 1992, 31, 1603–1609); Horne et al., *J Am Chem Soc.*, 1990, 112, 2435–2437).

Incorporation of base analogs of the present invention 15 into probes that also contain covalent crosslinking agents has the potential to increase sensitivity and reduce background in diagnostic or detection assays. In addition, the use of crosslinking agents will permit novel assay modifications such as (1) the use of the crosslink to increase probe discrimination, (2) incorporation of a denaturing wash step to reduce background and (3) carrying out hybridization and crosslinking at or near the melting temperature of the hybrid to reduce secondary structure in the target and to increase probe specificity. Modifications of hybridization conditions have been previously described (Gamper et al., *Nucleic Acids Res.*, 1986, 14, 9943).

Oligomers of the invention are suitable for use in diagnostic assays that employ methods wherein either the oligomer or nucleic acid to be detected are covalently attached to a solid support as described (U.S. Pat. No. 4,775,619). The oligomers are also suitable for use in diagnostic assays that rely on polymerase chain reaction techniques to amplify target sequences according to described methods (European Patent Publication No. 0 393 744). oligomers of the invention containing a 3' terminus that can serve as a primer are compatible with polymerases used in polymerase chain reaction methods such as the Taq or Vent™ (New England Biolabs) polymerase. Oligomers of the invention can thus be utilized as primers in PCR protocols.

The oligomers of the invention are useful as primers that are discrete sequences or as primers with a random sequence. Random sequence primers can be generally about 6, 7, or 8 nucleomonomers in length. Such primers can be used in various nucleic acid amplification protocols (PCR, ligase chain reaction, etc.) or in cloning protocols. The substitute linkages of the invention generally do not interfere with the capacity of the oligomer to function as a primer. Oligomers of the invention having 2'-modifications at sites other than the 3' terminal residue, other modifications that render the oligomer RNase H incompetent or otherwise nuclease stable can be advantageously used as probes or primers for RNA or DNA sequences in cellular extracts or other solutions that contain nucleases. Thus, the oligomers can be used in protocols for amplifying nucleic acid in a sample by mixing the oligomer with a sample containing target nucleic acid, followed by hybridization of the oligomer with the target nucleic acid and amplifying the target nucleic acid by PCR, LCR or other suitable methods.

The oligomers derivatized to chelating agents such as EDTA, DTPA or analogs of 1,2-diaminocyclohexane acetic acid can be utilized in various invitro diagnostic assays as described (U.S. Pat. Nos. 4,772,548, 4,707,440 and 4,707, 352). Alternatively, oligomers of the invention can be derivatized with crosslinking agents such as 5-(3-iodoacetamidoprop-1-yl) 2'-deoxyuridine or 5-(3-(4-bromobutyramido) prop-1-yl)-2'-deoxyuridine and used in arious assay methods or kits as described (International Publication No. WO 90/14353).

In addition to the foregoing uses, the ability of the oligomers to inhibit gene expression can be verified in invitro systems by measuring the levels of expression in subject cells or in recombinant systems, by an suitable method (Graessmann, M. et al, *Nucleic Acids Res.*, 1991, 19, 53–59).

The invention having been described above, the following examples are offered to better explain the invention. The examples are offered to illustrate the invention and should not be interpreted as limiting the invention.

EXAMPLES

Overview of the Synthesis of the Nucleomonomer Synthon and Oligomers

The oligomers of the invention can be synthesized using reactions known in the art of oligonucleotide derivative synthesis. See e.g. Flandor, J. and Yam, S. Y., *Tetrahedron Letts.*, 1990, 31, 597–600; Mattson, R. J. et al., *J Org Chem.*, 1990, 55, 2552–2554; Chung, C. K. et al., *J Org Chem.*, 1989, 54, 2767–2769.

As can be seen from the variety of substitute linkages specifically listed in Table 1, the substitute linkages of the invention can vary so as to contain one or more nitrogen, sulfur, and/or oxygen atoms in their structure. The positions of these atoms in the substitute linkage can vary from the "5'" end, to the "middle" to the "2'" or "3'" and "4'" end. In this section, a series of representative synthesis reaction figures are set forth which provide routes to various ocations and combinations of nitrogen and oxygen atoms within he substitute linkages.

The synthesis illustrated in FIGS. 1–25 be modified as is known to those practicing in the area of oligonucleotide chemistry. For example, although protection of the bases is not always indicated in the synthesis figures, such may be desirable and can be accomplished using reagents and techniques known in the art. See, e.g. Protective Groups in Organic Synthesis (Theodora W. Greene, John Wiley and Sons, 1981). Similarly, although the use of protective groups is shown in some cases, it is not always necessary to block the reactants in order to synthesize the exemplified invention oligomers.

Example 1

The first five steps shown in FIG. 1 relate to the preparation of isobutryl protected serinol amino acid alcohol. The sixth and subsequent steps in FIG. 1 are directed to the synthesis of the serinol substituted thymine phophoramidite building block.

In step 1 of FIG. 1, the amino group of the serine amino acid is protected by reacting 1 with di-tert-butyl dicarbonate to yield compound 2. Other equivalent protecting groups may be used. In the next step, the β-hydroxyl group of Compound 2 is blocked with dihydropyran to give fully protected amino acid 3. The amnio acid 3 is then reacted with diborane-dimethyl sulfide complex to provide alcohol 4, which on exposure to isobutryl chloride gave 5. This reduction reaction can also be carried out using isobutyl choloroformate and sodium borohydride (see: K. Ramasamy, R. K. Olsen and T. Emery, Synthesis, 1982, 42). Reaction of 5 with rifluoroacetic acid for 30 minutes followed by washing with aHCO$_3$ afforded 6.

Thymine acetic acid 7 was prepared as described in the literature (see: L. Kosynkina, W. Wang and T. C. Liang, *Tetrahedron Letts*, 1994, 35, 5173). Coupling of 7 with 6 under mixed anhydride condition provided 8. Dimethoxytritylation of 8 with DMTCl gave compound 9, which on hydrolysis with base afforded 10. Phophysitylation of 10 under standard condition provided the serinol coupled thymine building block 11. This synthon can then be added into a growing oligomer using conventional chemistry. Any DNA synthesis chemistry such as phosphoramidate or phosphonate chemistry can be used to link monomers or dimers in a manner analogous to that set forth above.

Example 2

Figure 2:
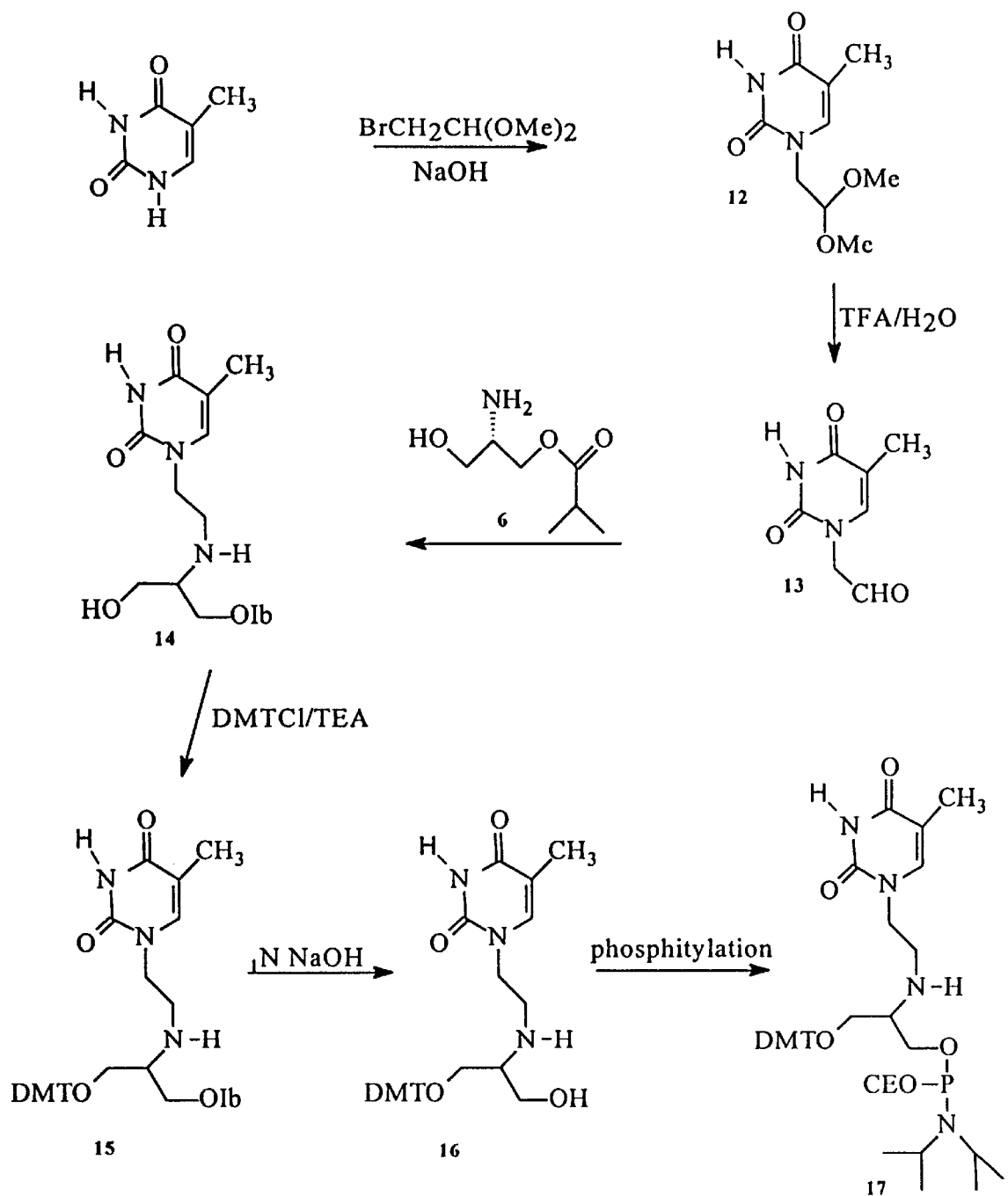

In reaction FIG. 2, thymine acetaldehyde 13 was produced by the treatment of thymine with bromoacetaldehyde dimethylactal followed by hydrolysis of 12 with aqueous TFA. Aldehyde 13 and amine the 6 are then coupled and the corresponding intermediate was transformed to the phosphoroamidite building block 17 in a manner analogous to the steps used in FIG. 1.

Example 3

Figure 3:
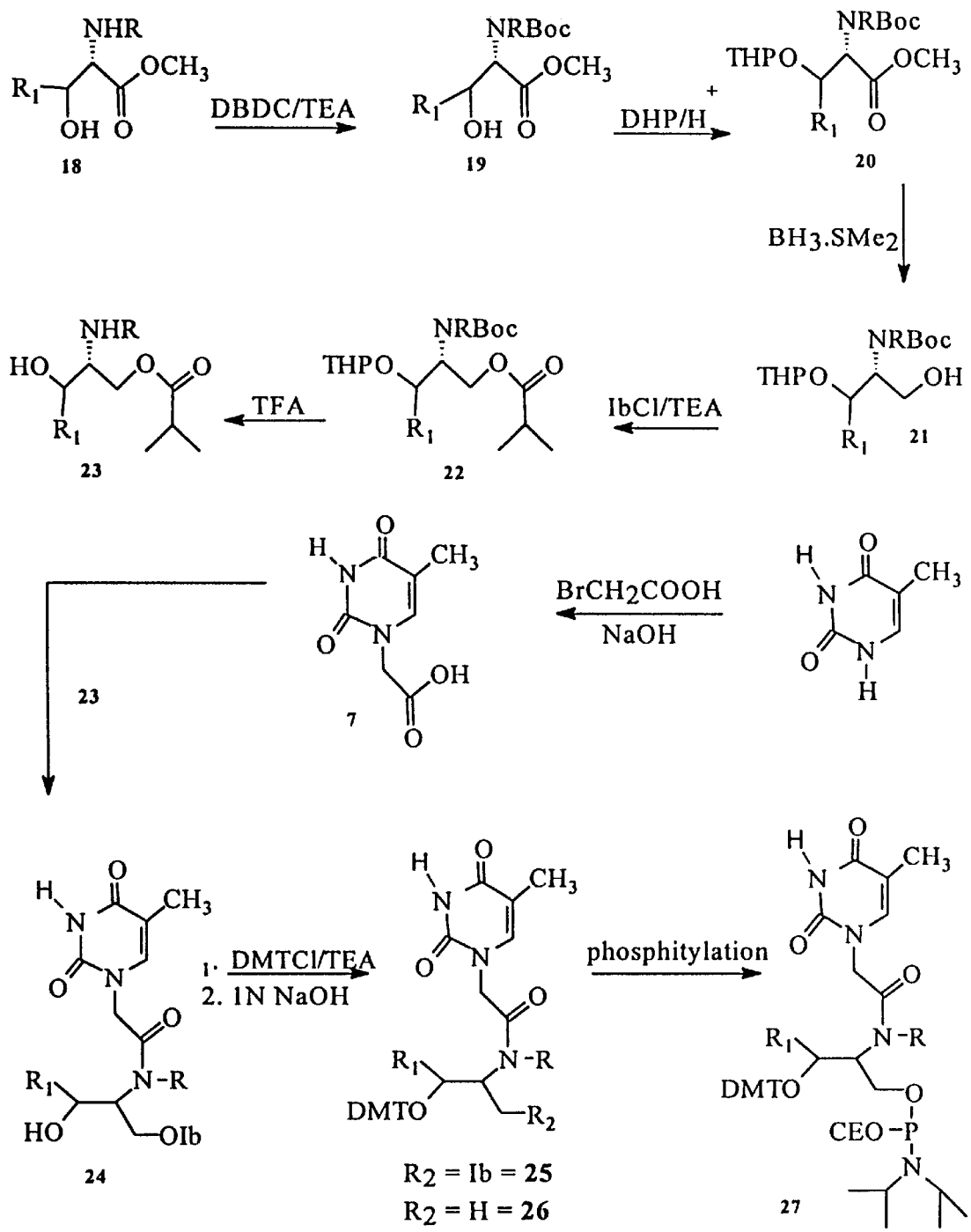

In reaction FIG. 3, the starting material is a β-substituted amino acid 18. The substituted amino acid could be transformed into the phosphoroamidite building block 27 by following the procedure of the steps used in FIGS. 1 and 2.

Example 4

Figure 4:
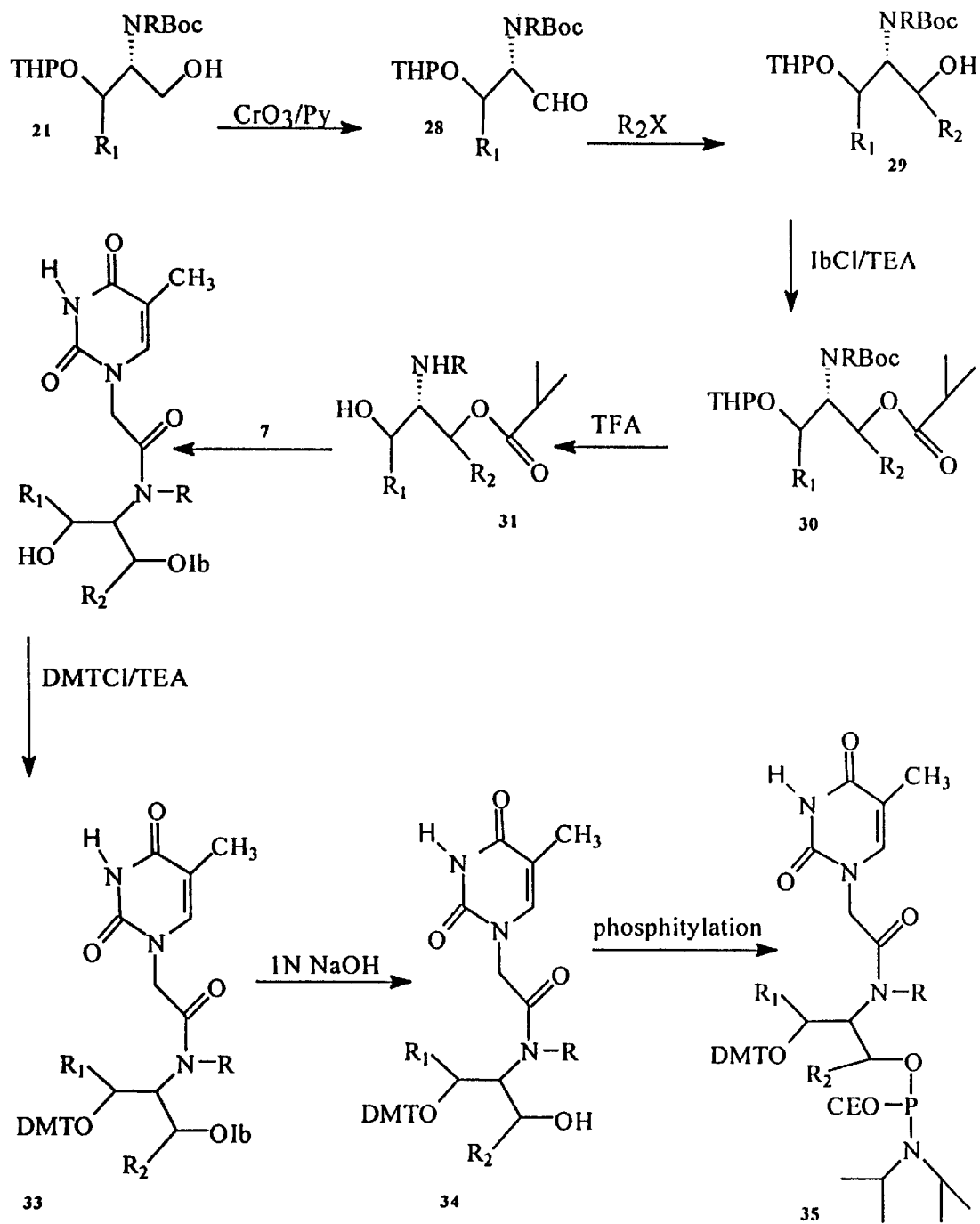

In FIG. 4, the starting amino alcohol 21 is oxidized with CrO$_3$/pyridine mixture to give an aldehyde 28. The aldehyde which on reaction with alkyl halide in the presence of a base should yield compound 29. The amino alcohol 29 could then be transformed to the building block 35 in a manner analogous to the steps used in FIG. 1 and 2.

Example 5

Figure 5A:
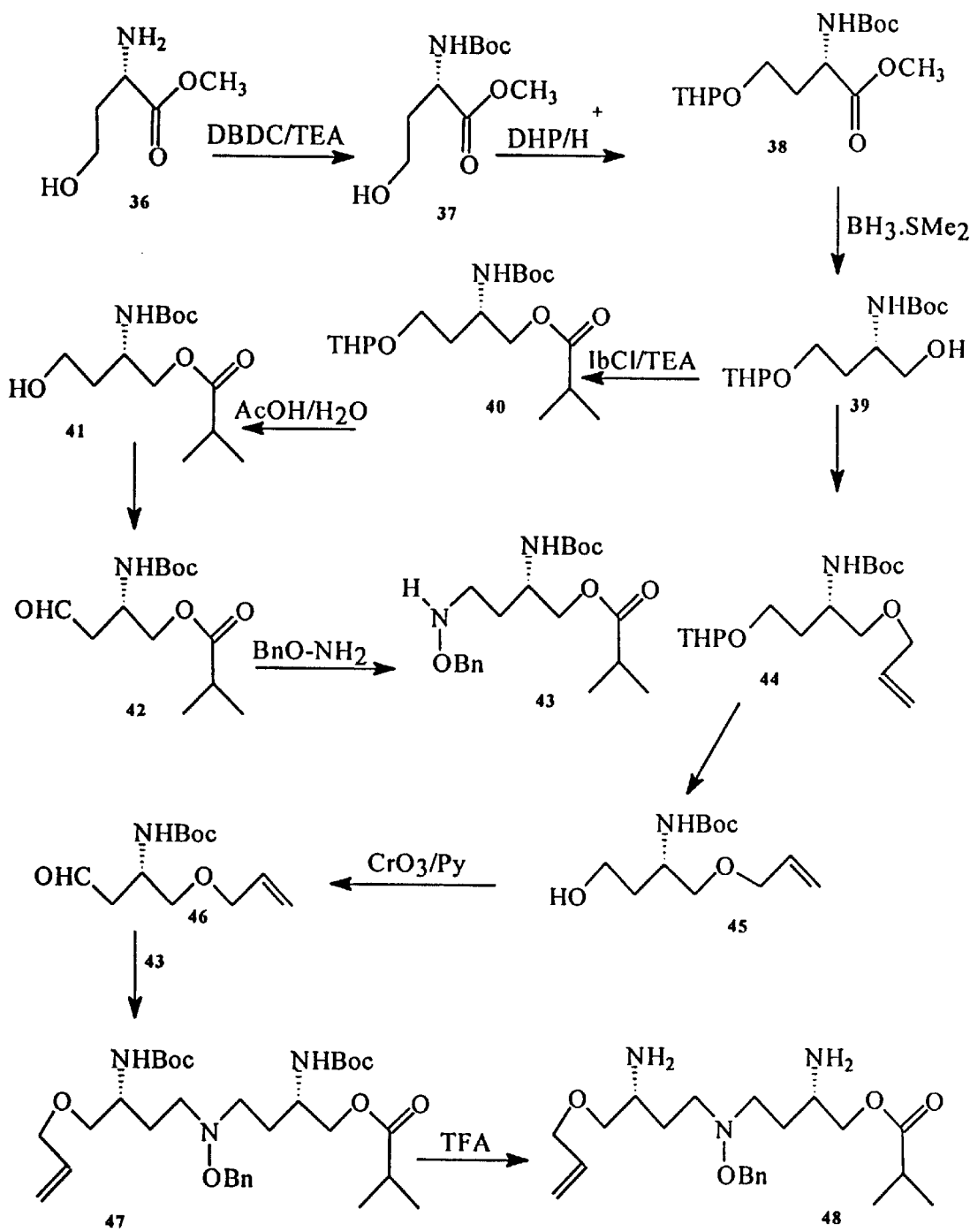
Figure 5B:
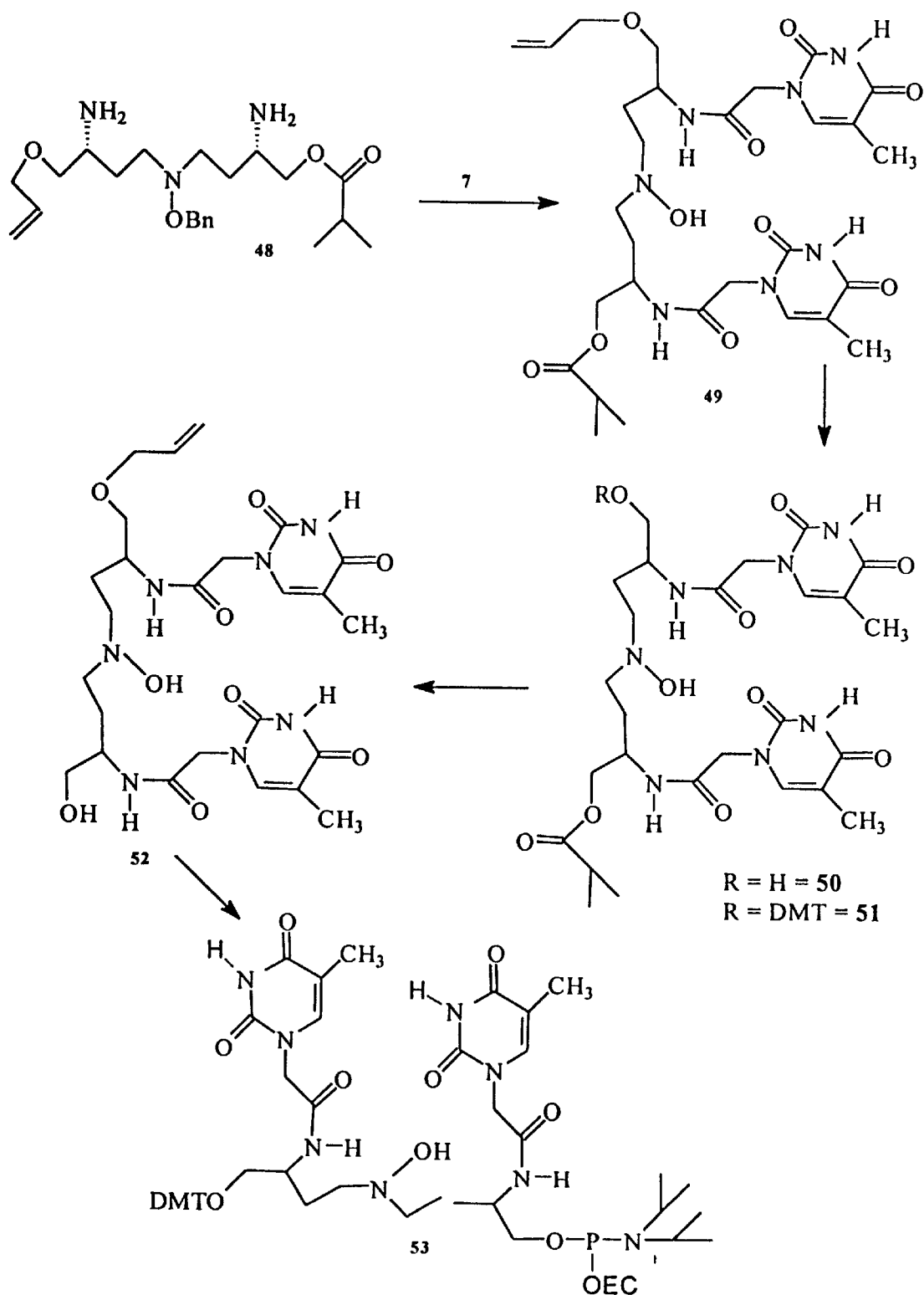

Turning to FIG. 5, the first four steps are essentially the same steps as used in FIG. 1, in this aspartic acid is used instead of serine. Aspartic acid methylester 36 gave fully protected alcohol 40, which on selective deprotection with acetic acid provided 41. Oxidation of 41 with CrO$_3$/pyridine gave the corresponding aldehyde 42. Reductive is amination of the aldehyde 42 with o-benzylhydroxyl amine in the presence of sodium triacetoxyborohydride should give 43 (see: T. Kolasa and M. J. Miller, *J. Org. Chem.*, 1990, 55, 1711). The alcohol 39 is then converted to an aldehyde 46, essentially using the same reaction conditions as said above but with an allylic protecting group for the hydroxyl function of 39. Coupling of the aldehyde 46 and the hydroxylamine 43 in presence of sodium triacetoxyborohydride followed by deprotection of the amino protecting groups should afford the bisamine 48. The bisamine 48 could then be converted to a dimer 53 by following the steps used in FIG. 1.

Example 6

Figure 6:
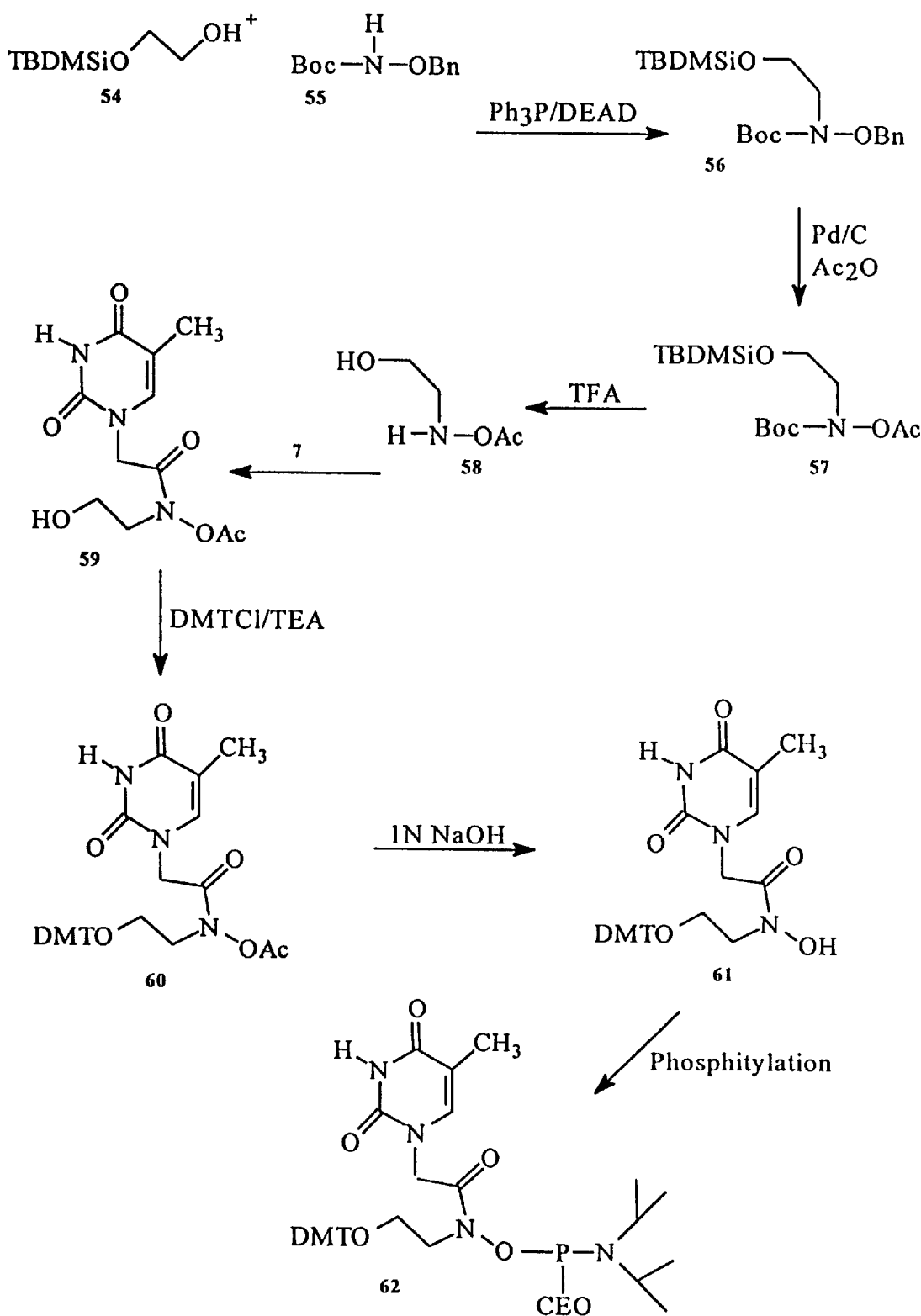

In FIG. 6, coupling of alcohol 54 with O-benzylhydroxylamine 55 under Mitsunobu reaction condition (see: O. Mitsunobu, Synthesis, 1981, 1) provides compound 56. The intermediate 56 on hydrogenation followed by acetylation should give 57. Exposure of 57 to TFA deblocks the "TBDMSi" protecting group and gives 58. Coupling of 58 with 7 followed by dimethoxytritylation could provide 60. The final building block 62 should be accomplished from 60 by base hydrolysis followed by phosphitylation.

Example 7

Figure 7:
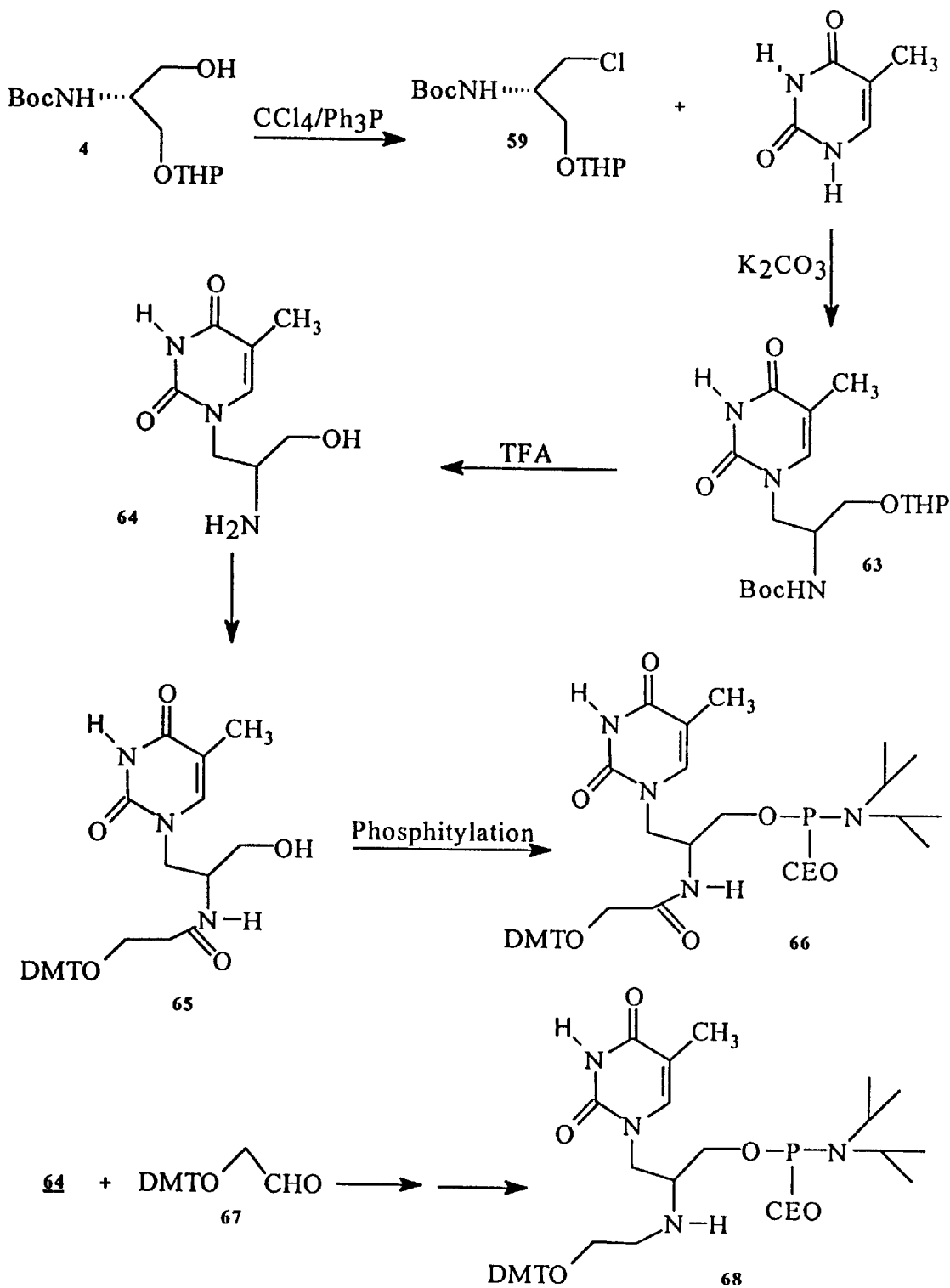

In FIG. 7, the serinol 4 is converted to a halide 59 and alkylated with thymine to provide 63. The protecting groups in 63 are removed, coupled with DMT-protected hydroxyacetic acid and phosphitylated to yield 66.

Example 8

Figure 8A:
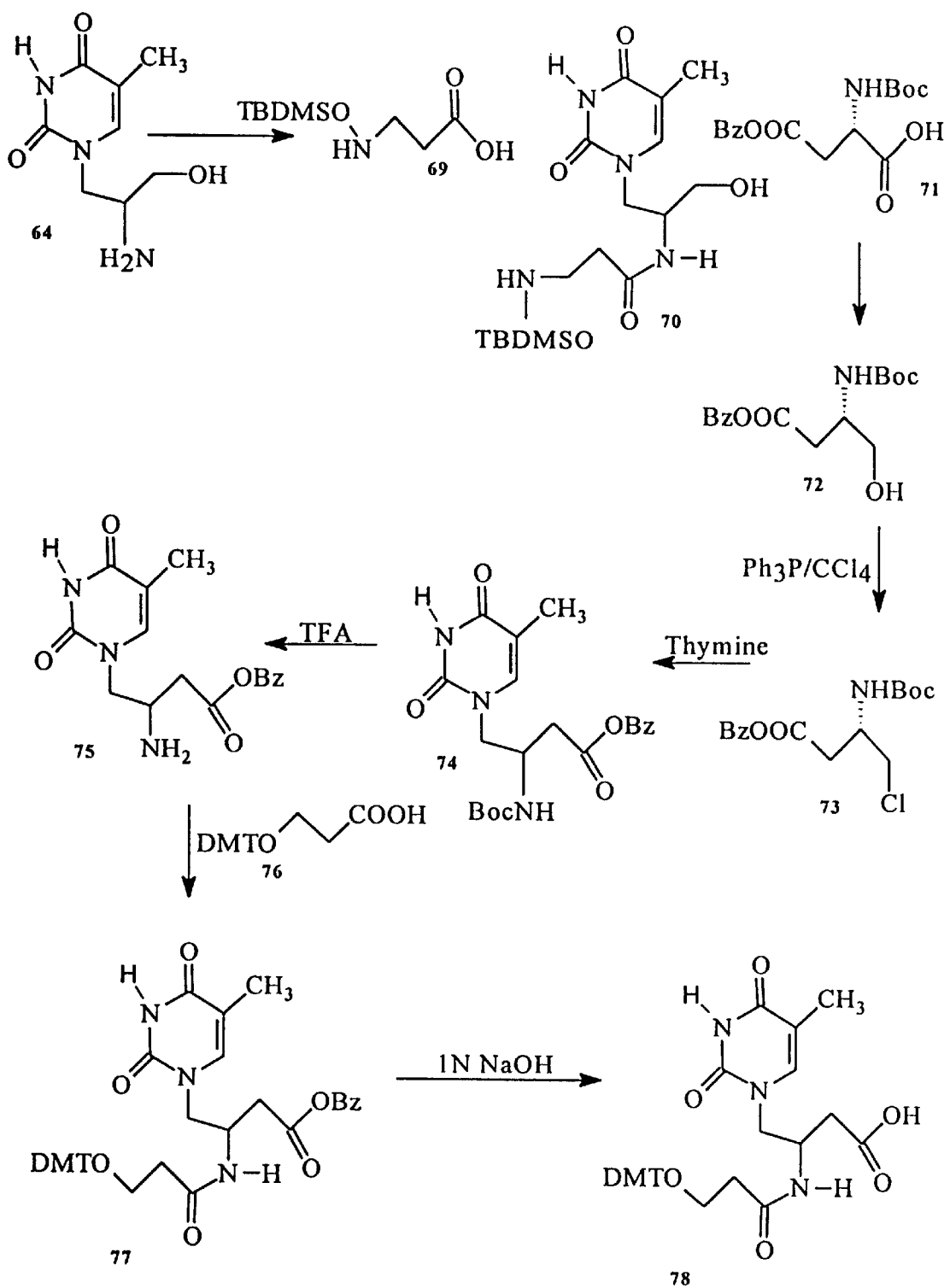
Figure 8B:
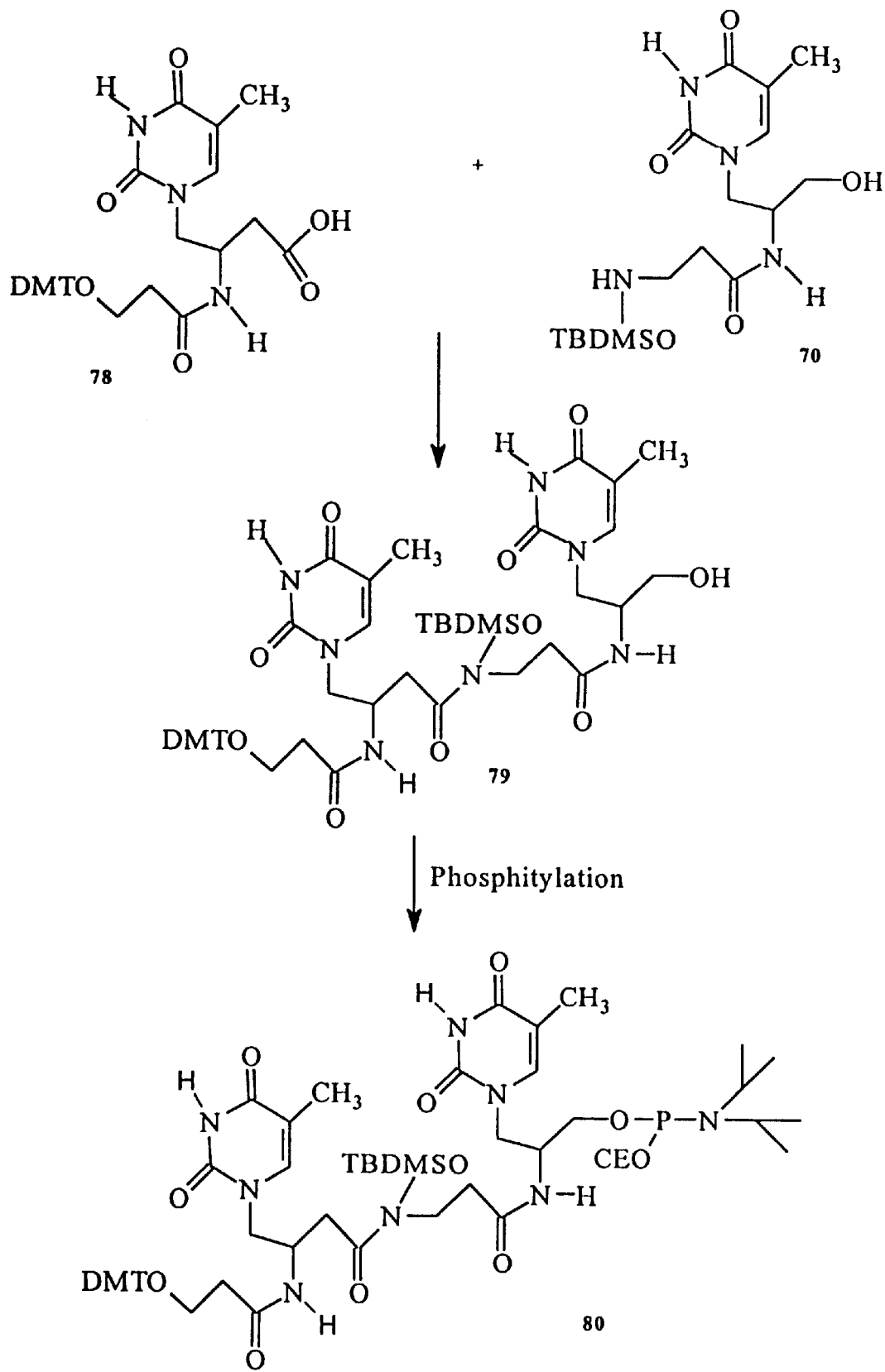

In FIG. 8, the alcohol 64 is coupled with N-hydroxylaminopropanoic acid 69 to give 70. Alkylation of thymine with a halide 73 gives 74 which on deprotection, coupling with 76 followed by hydrolysis could afford 78. Condensation of 78 with 70 followed by phosphitylation should give the hydroxamate dimer 80.

Example 9

Figure 9A:
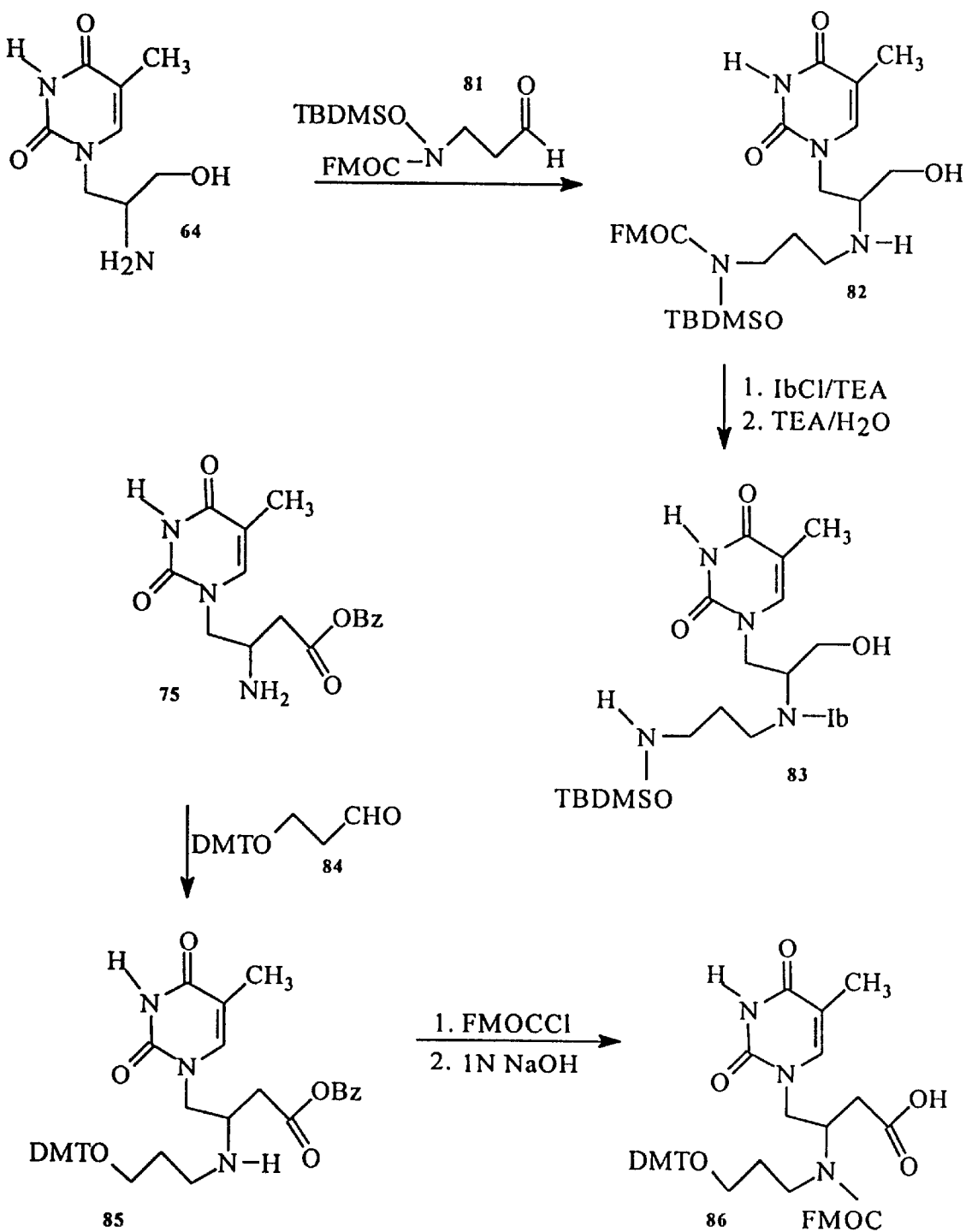
Figure 9B:
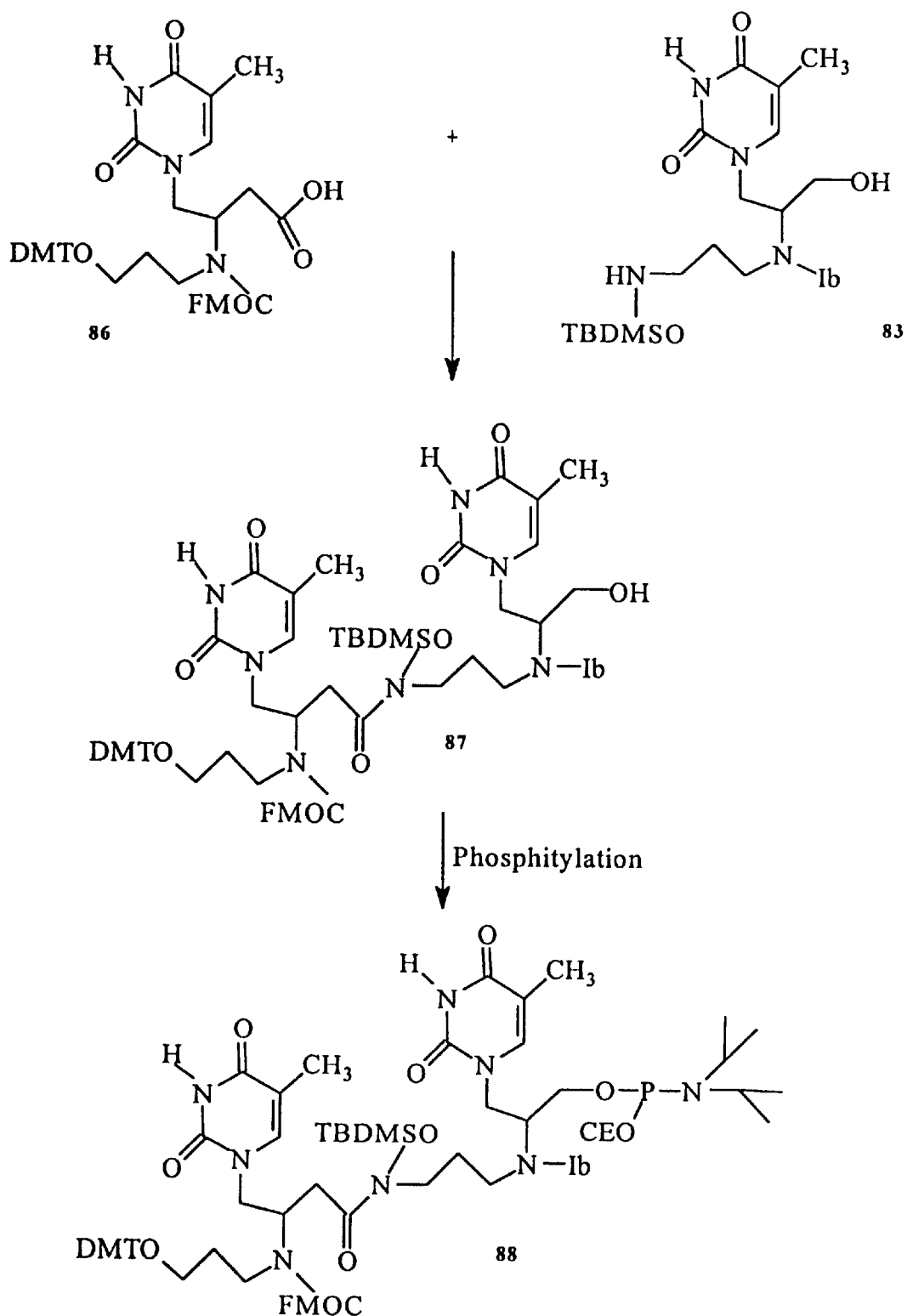

In FIG. 9, N-hydroxylamino propanoic aldehyde 81 is used to couple the alcohol 64. The dimer 88 is prepared from 83 and 86 by following the steps used in FIG. 8.

Example 10

Figure 10:
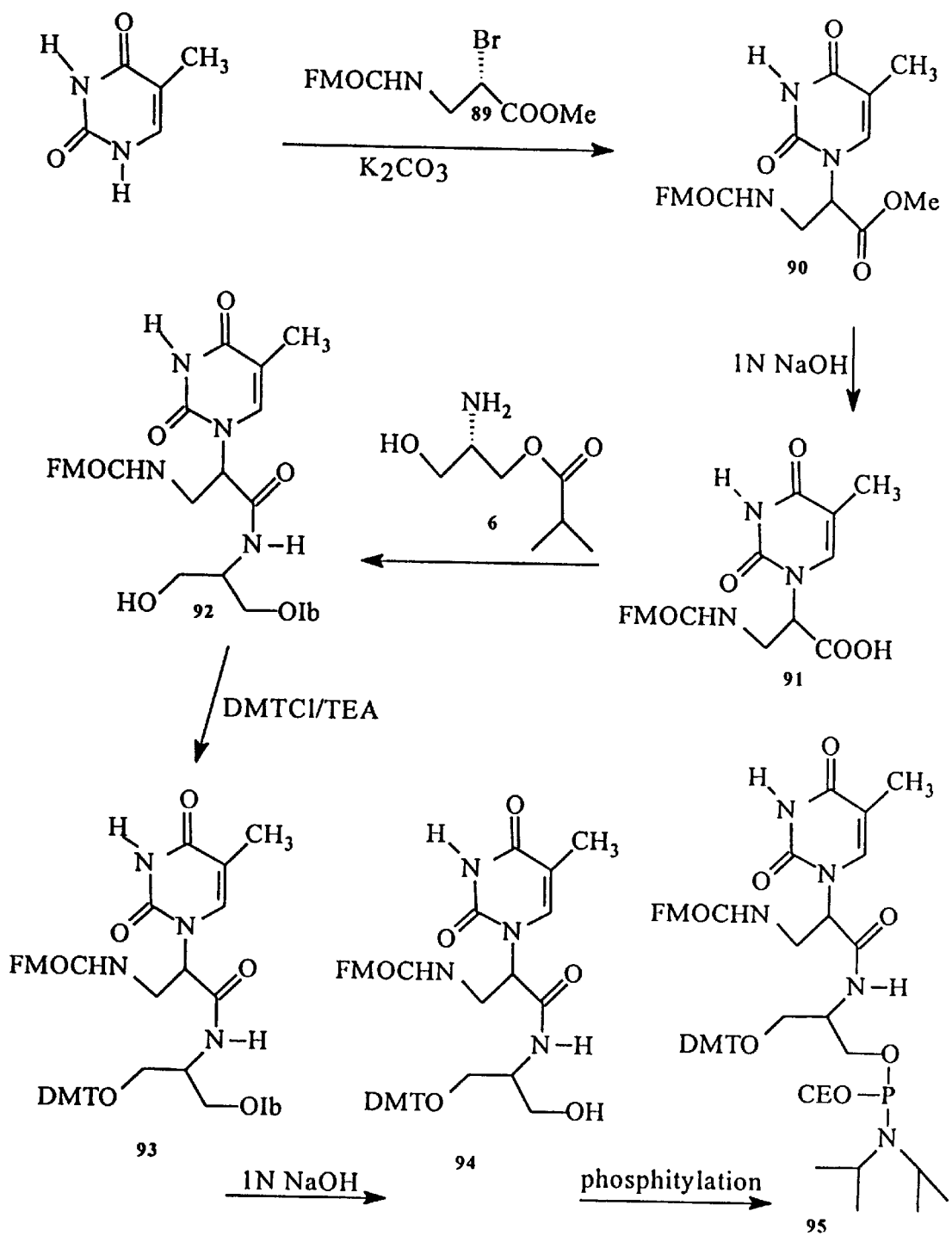

In FIG. 10, alkylation (see: T. Kolasa and M. J. Miller, *J. Org. Chem.*, 1990, 55, 4246) of α-bromo-β-aminopropanoic acid methylester 89 with thymine would produce 90. The intermediate 90 on hydrolysis with sodium hydroxide gives an acid 91 which is coupled with 6 to provide 92. The compound 92 is then converted into the phosphoroamidite building block 95 using the steps described in FIG. 1.

Example 11

Figure 11:
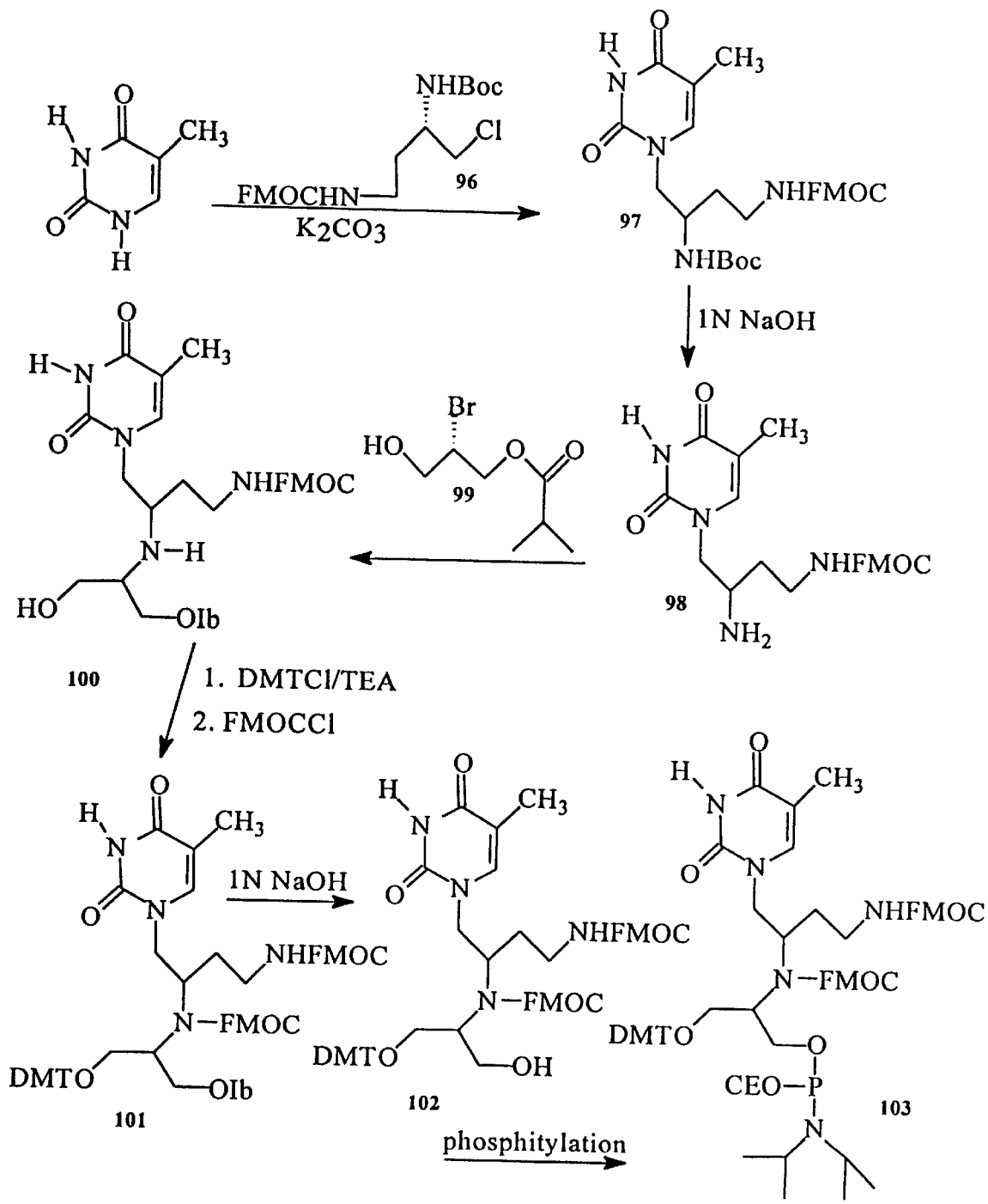

In FIG. 11, thymine is alkylated with an alkylamine halide 96 (see: R. K. Olsen, K. Ramasamy and T. Emery, *J. Org. Chem.*, 1984, 49, 3527 and Islam et al., *J. Med. Chem.*, 1994, 37, 293–304 for the preparation of aminoalkyl halide) to give 97. Exposure of the compound 97 to TFA followed by alkylkation would afford 100. The building block 103 is obtained from 100 by dimethoxytritylation, hydrolysis, followed by phosphityation.

Example 12

Figure 12:
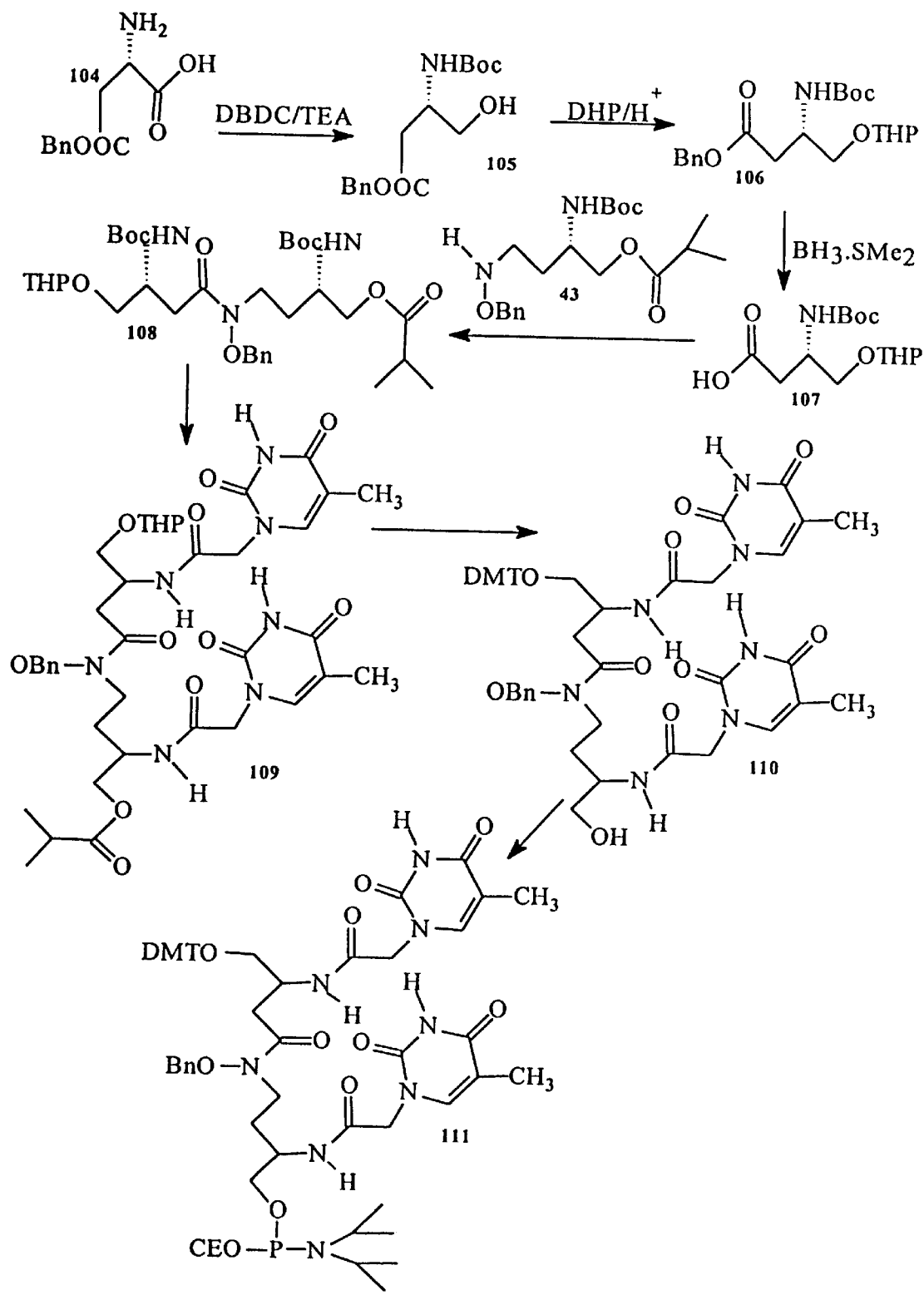

FIG. 12 is an alternative route to a hydroxamate backbone dimer 111 from N-hydroxylamine 43 and an aldehyde 107 which in turn prepared from aspartic acid.

Example 13

Figure 13:
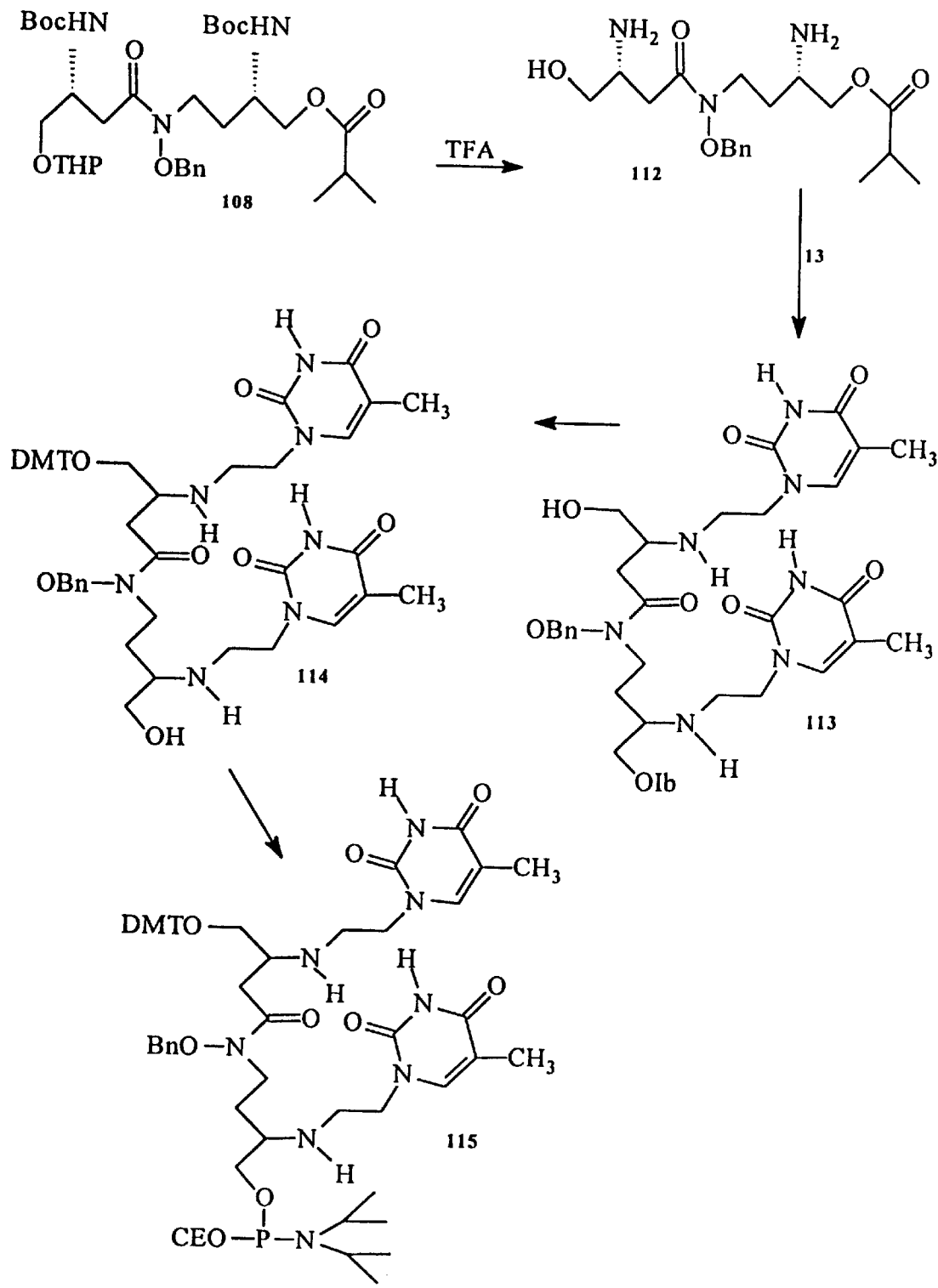

In FIG. 13, the dimer 115 is prepared from the intermediate 108 and 13 by following the same steps of reactions described in FIG. 2.

43

Example 14

Figure 14:
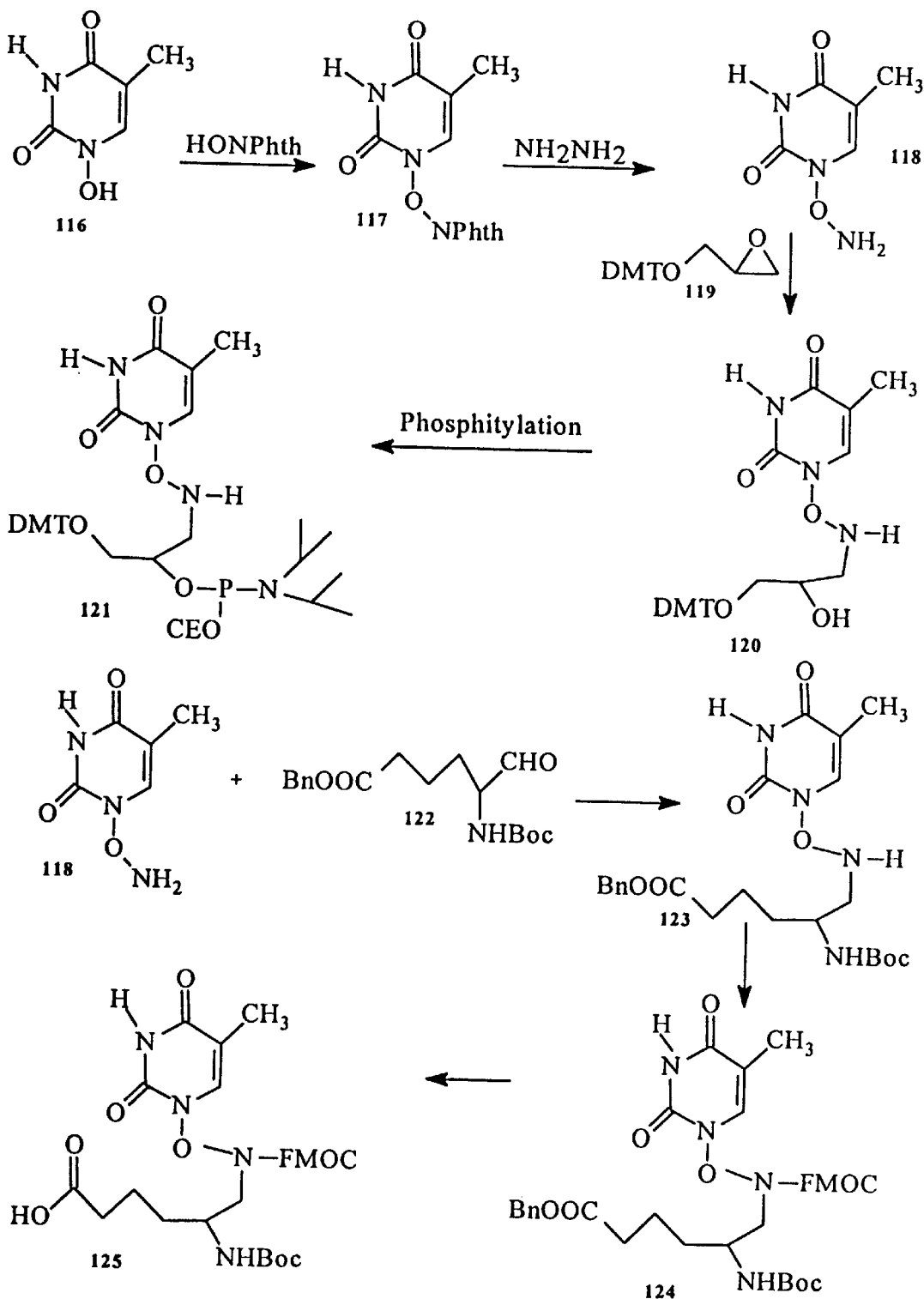

In FIG. 14, N-hydroxylthymine is prepared (see: Kim, C. U., et al., *Tetrahedron Letts.*, 1992, 33, 25–28) and coupled with N-hydroxyphthalimide to provide 117 which on exposure to hydrazine in ethanol should give 118. Treatment of 118 with DMT-protected glycerol epoxide 119 provides 120. The intermediate 120 is then transformed to the phosphoroamidite 121 using standard procedure. In second synthesis, compound 118 is coupled with amino acid aldehyde 122 under reductive amination conditions to provide 123. Protection of the secondary amino functionality with FMOCCl followed by hydrolysis should afford 125.

Example 15

Figure 15:
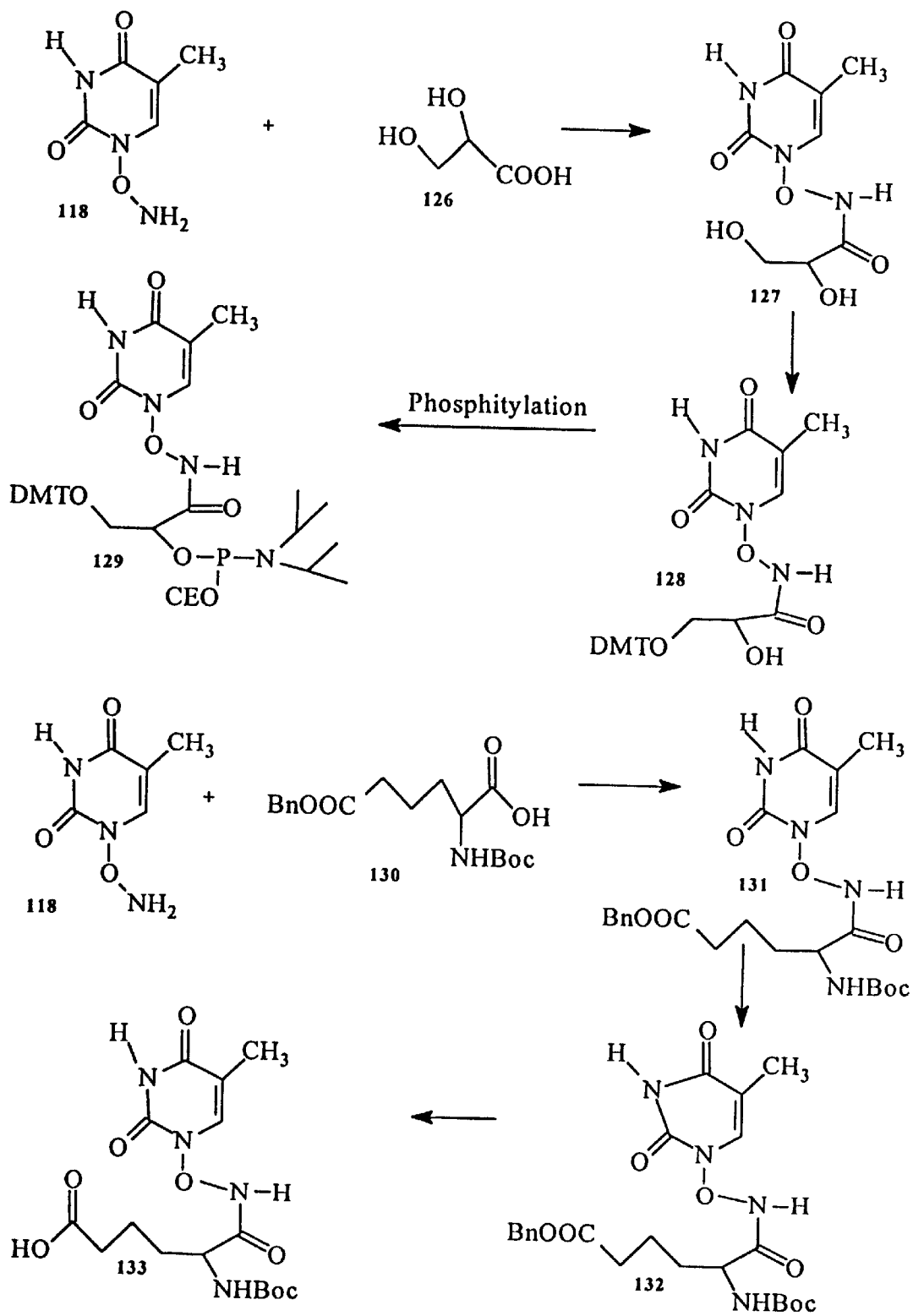

In FIG. 15, 1,2-dihydroxypropanoic acid 126 is coupled with N-hydroxylamine thymine 118 to give 127, which is then 5transformed into phophoramidite synthon 129 under standard conditions. The compound 118 is also coupled with adipic acid and transformed into nucleic acid building block 133.

Example 16

Figure 16:
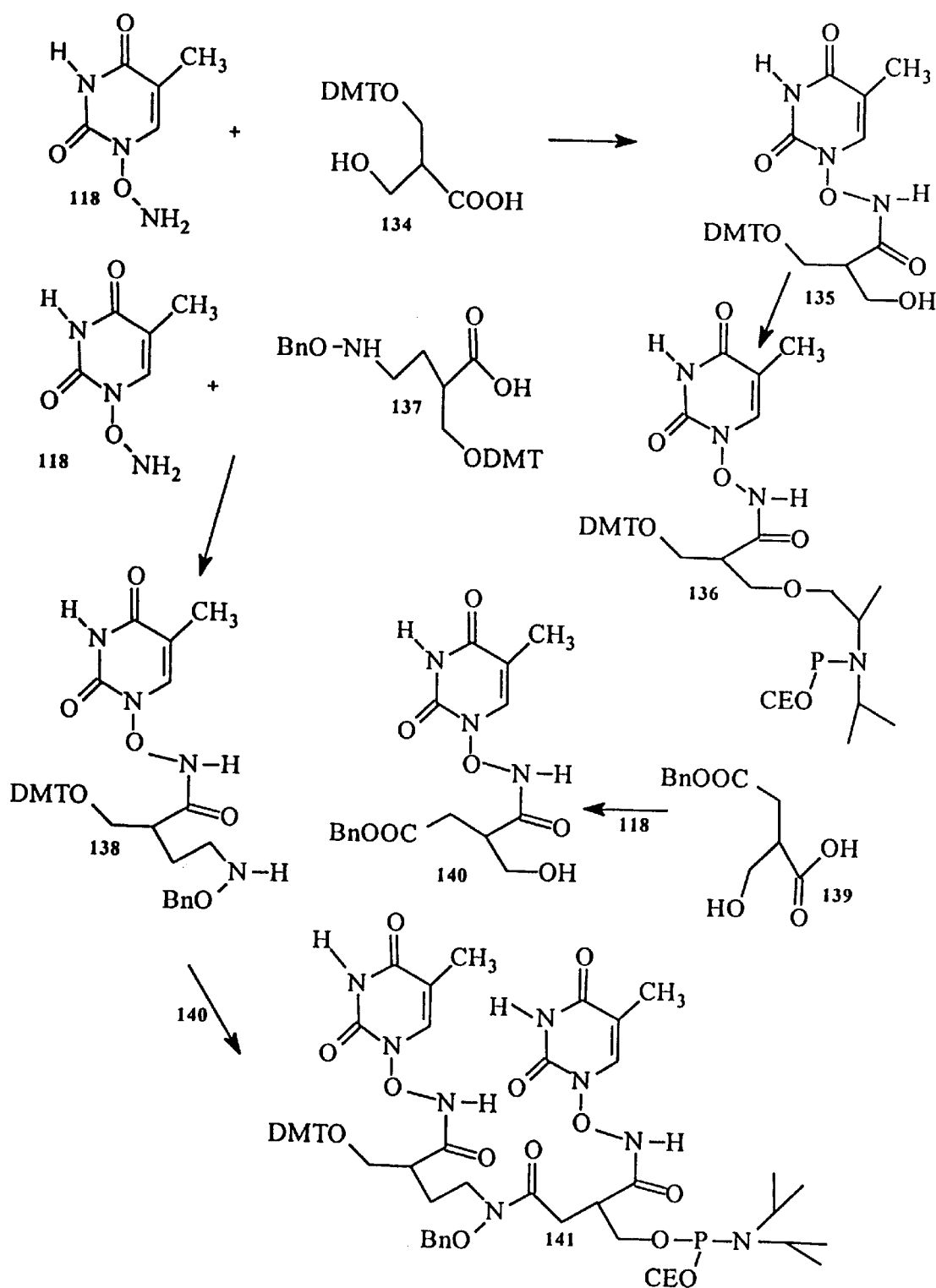

In FIG. 16, first the building block 136 is synthesized from 118 and 134 in a similar manner described in FIG. 1. Coupling of 139 with 118 provided 140. Treatment of 137 with 118 should provide 138 which on condensation with 140 gives the dimer 141.

Example 17

Figure 17:
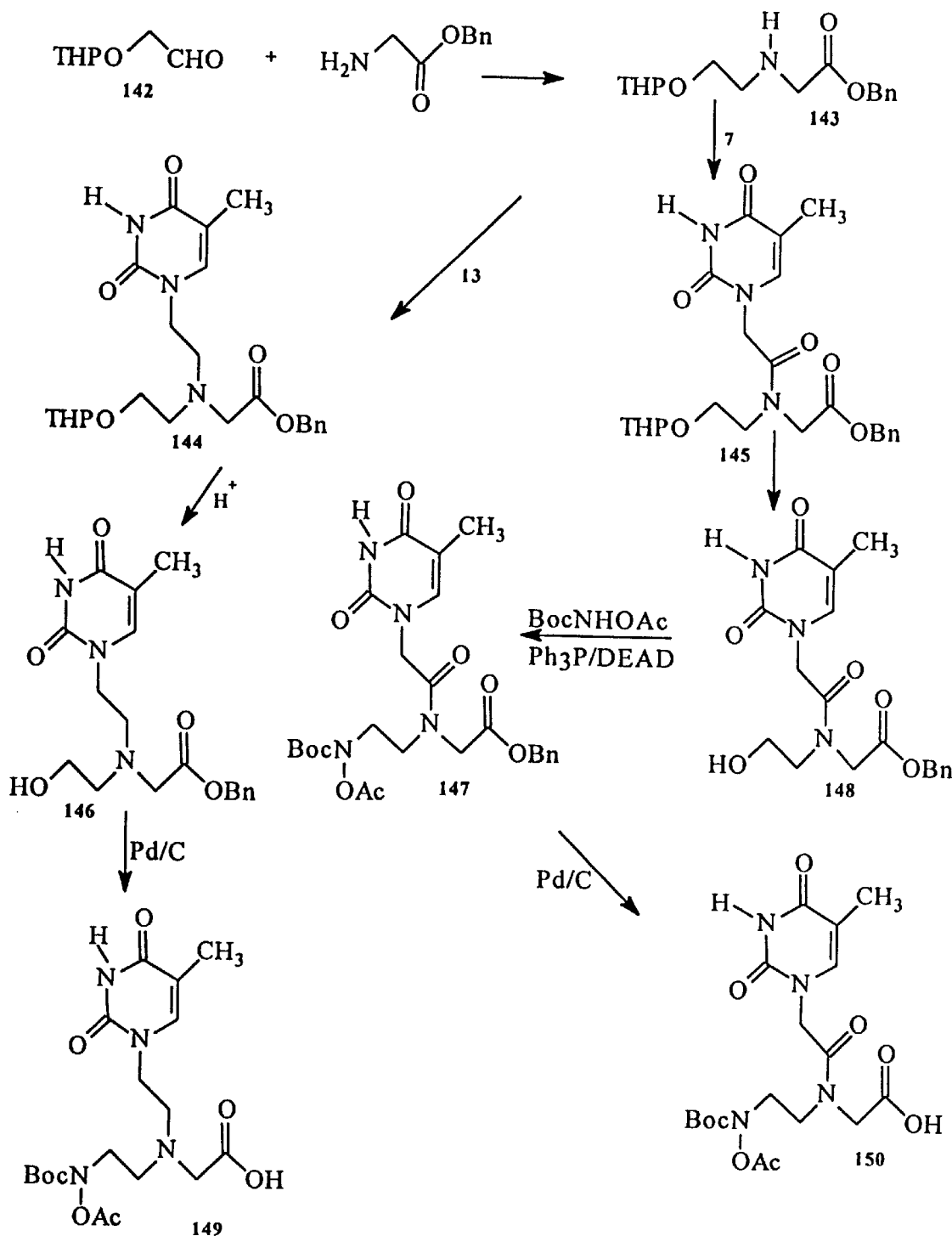

In FIG. 17, an aldehyde 142 and an glycine benzylester is coupled to give 143. Treatment of 143 with 7 should provide 145 which on exposure to acetic acid gives 148. Mitsunobu alkylation of 148 with Boc-NH-O-acetylhydroxylamine should give 147 which on hydrogenation the building block 150 could be obtained. Similarly coupling of 143 with 13 and following the same reactions as above should yield the synthon 149.

Example 18

Figure 18:
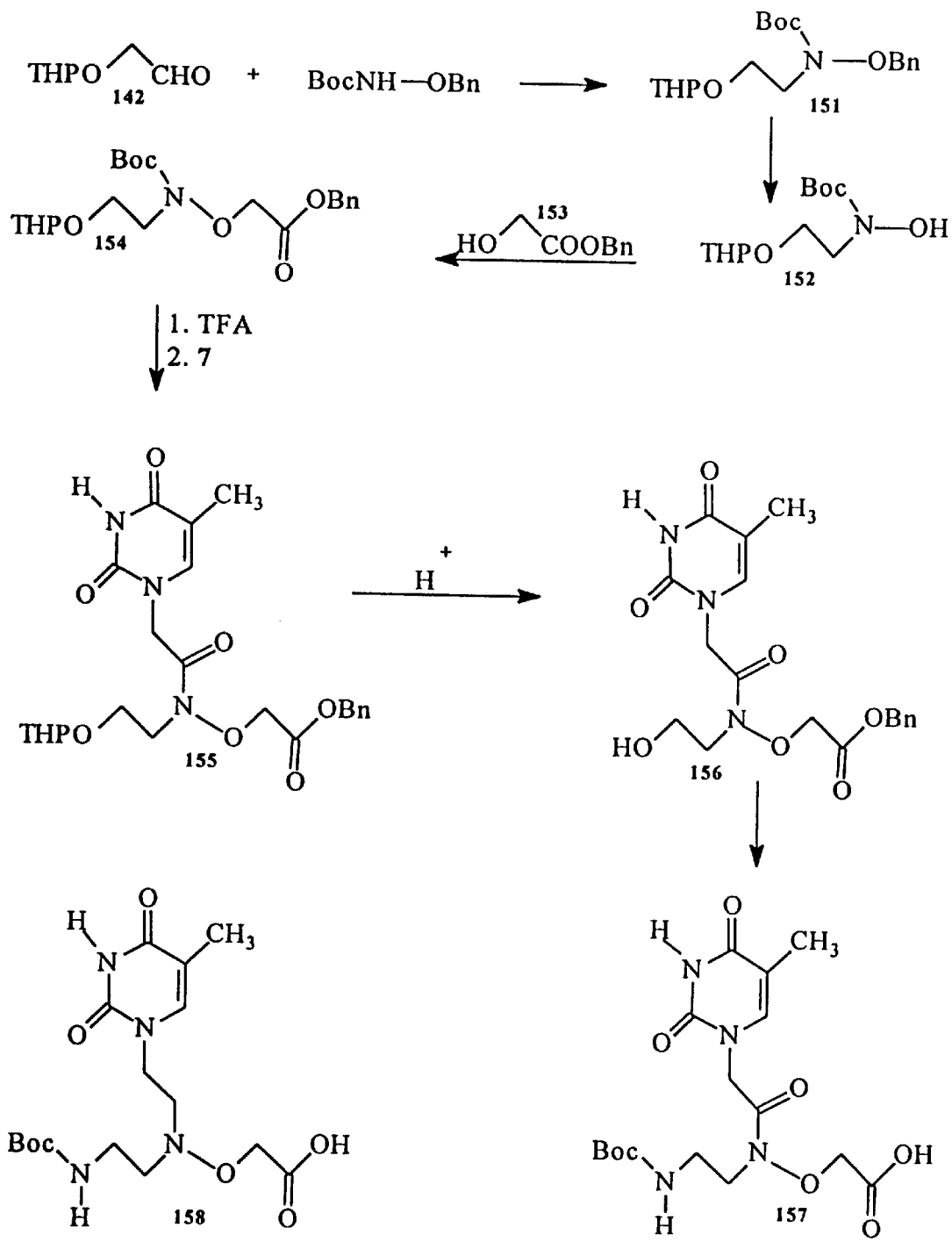

In FIG. 18, reductive amination of the aldehyde 142 and Boc-NH-O-benzylhydroylamine gave 151. Hydrogenation of 151 followed by alylation of 152 with glycolic acid 153 (B. C. Borer and D. C. Balogh, *Tetrahedron Letts.*, 1991, 32, 1039) should yield 154. Treatment of 154 with TFA willl remove the Boc protecting group, which on coupling would result in 155. The hydroxyl protecting group of 155 could selectively be removed with acetic acid to give 156. The compound 156 will then be transformed to the building block 157 using standard reaction conditions. Similarly the building block 158 will be produced by coupling of 154 with 13 and following the steps used for the preparation of 157.

Example 19

Figure 19:
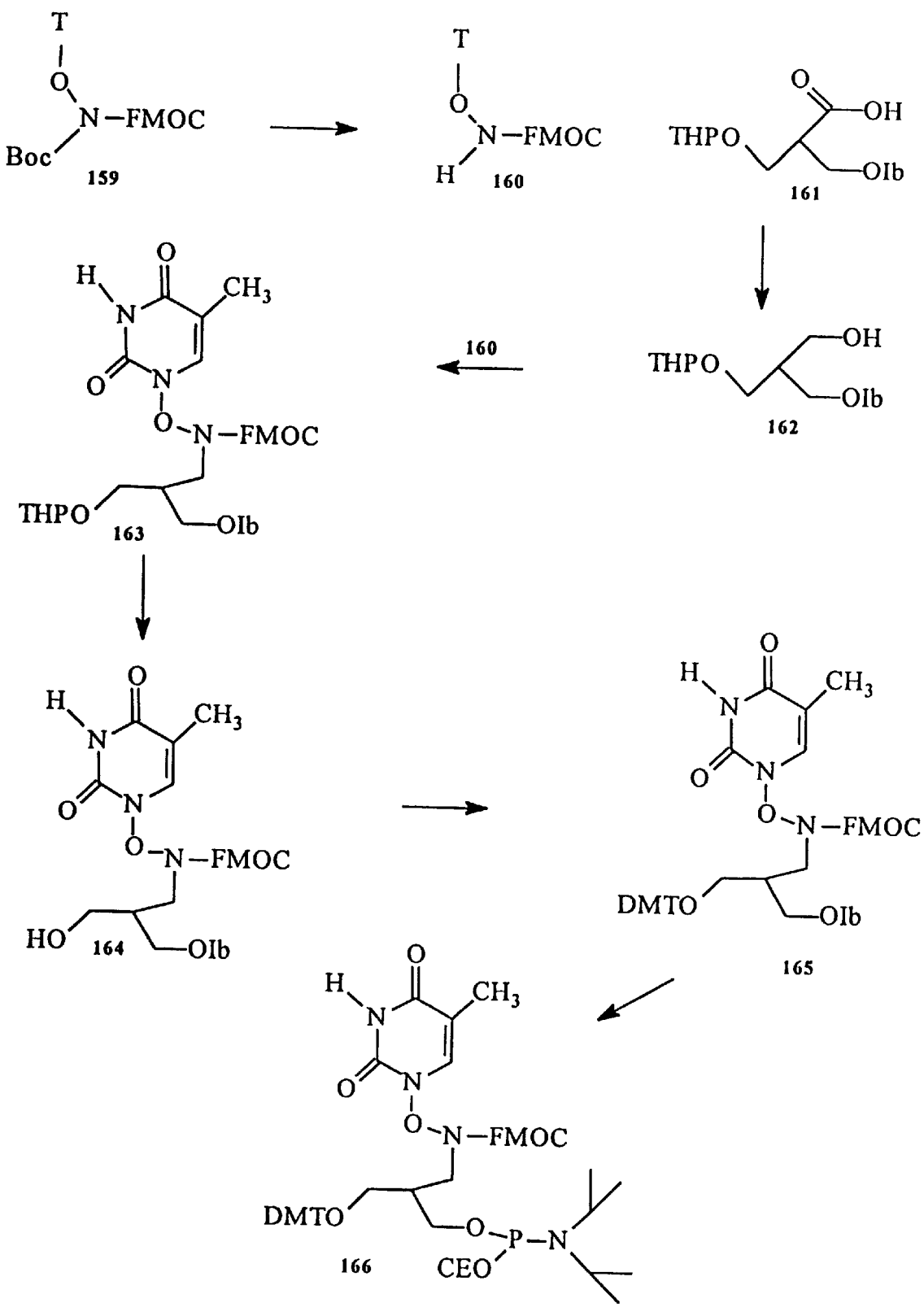

In FIG. 19, alkylation of thymine-N-hydroxylamine 160 with alcohol 162 will yield 163. The compound 163 could be transformed to the phosphoroamidite building block 166 by following the steps used in FIG. 1.

Example 20

Figure 20:
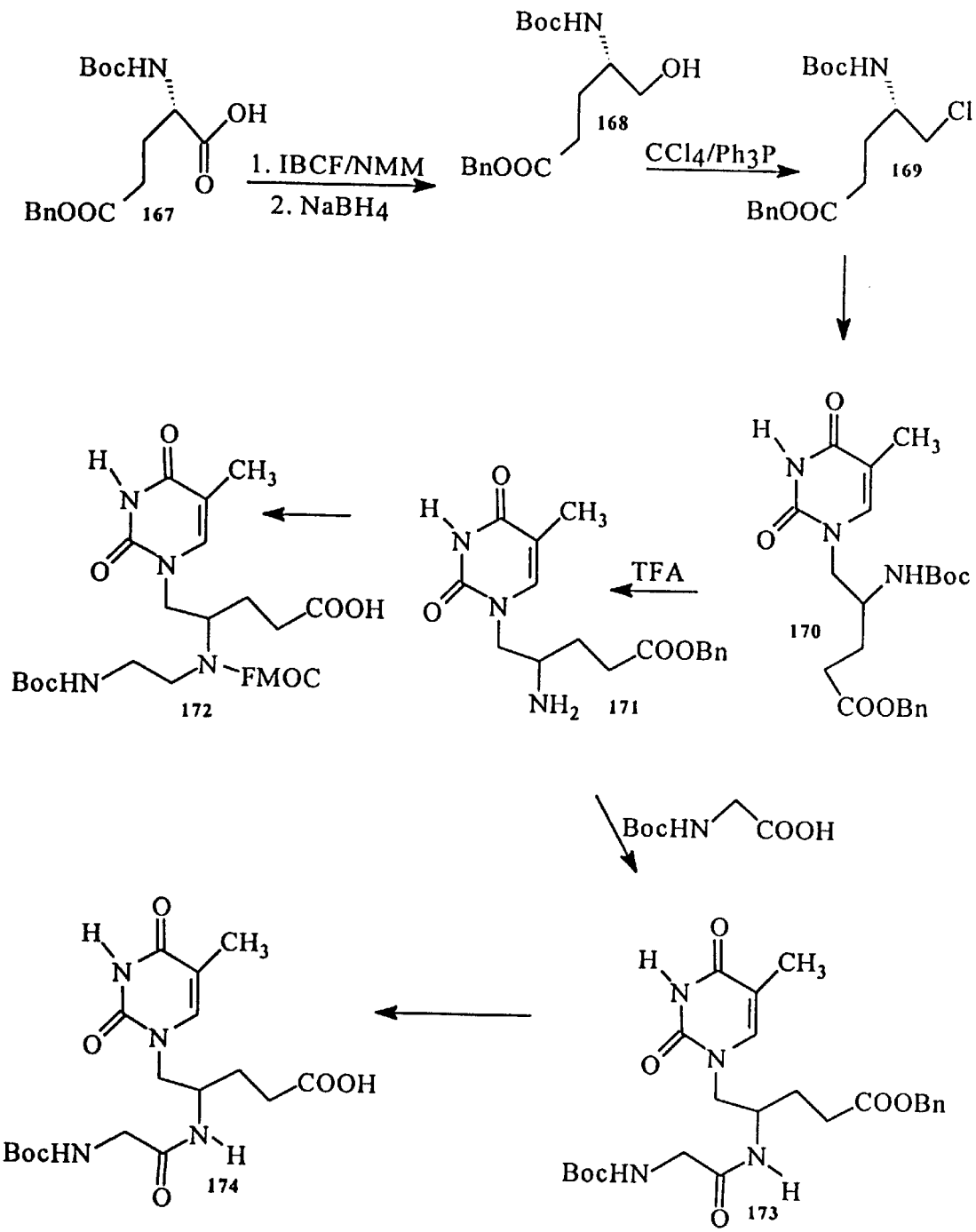

In FIG. 20, first the intermediate 169 is synthesized from glutamic acid using standard reaction conditions. Alkylation of thymine with 169 would give 170 which on treatment with TFA should produce 171. The intermediate 171 could be coupled with Boc-glycine to provide 173 which on hydrolysis would afford the monomer synthon 174. Similarly 172 could be prepared by coupling of 118 and Boc-aminoacetic aldehyde followed by hydrolysis of the benzylester.

Example 21

Figure 21:
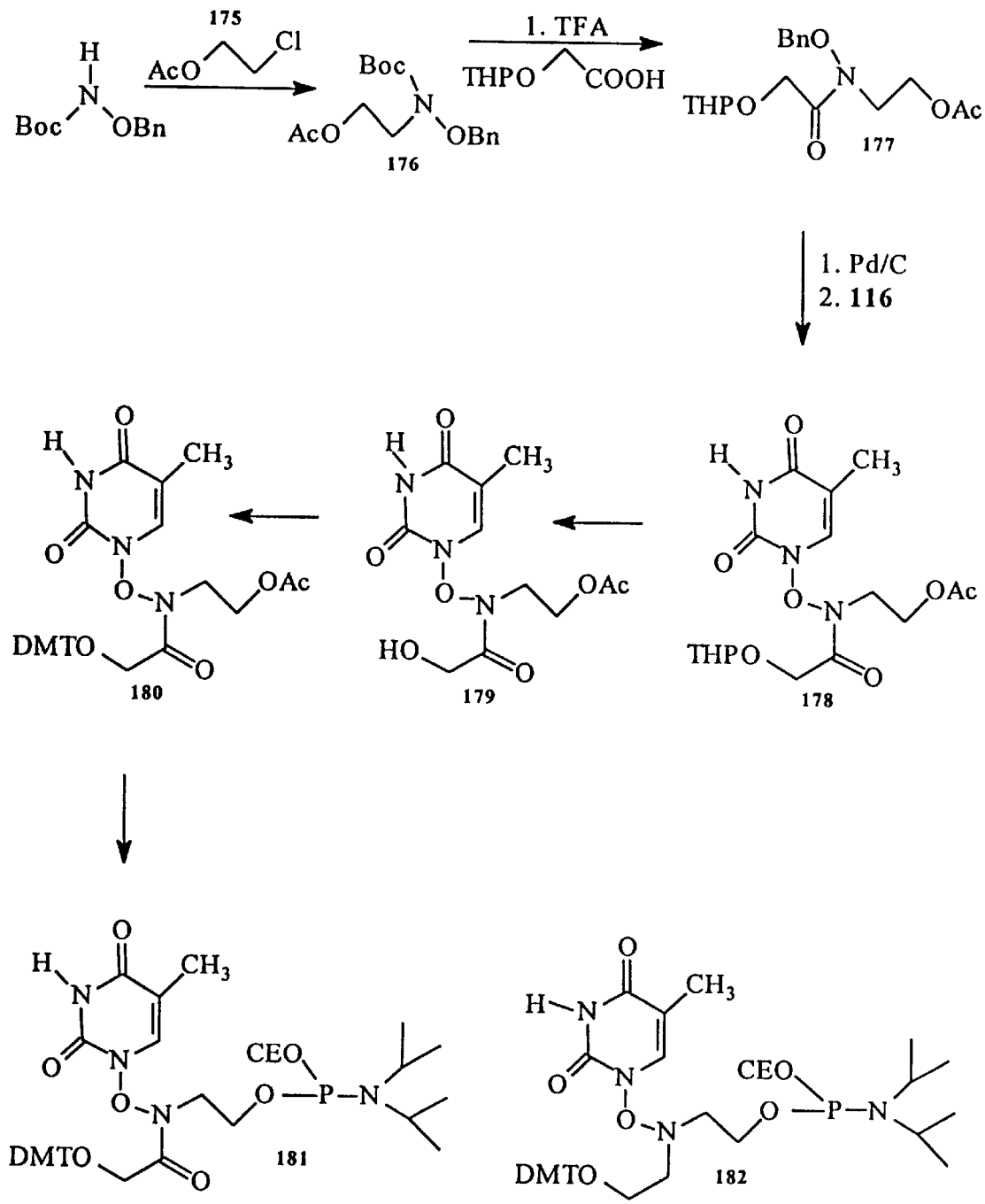

In FIG. 21, the intermediate 177 is prepared from Boc-NH-O-benzylhydroxylamine and 175 using standard reaction conditions. Hydrogenation of 177 followed by coupling with N-hydroxythymine 116 would produce 178. Removal of the THP protecting group followed by dimethoxytritylation and phosphitylation should give the building block synthon 181. Similarly 182 could be prepared by following all the above reactions and using THP-Hydroxyacetic aldehyde instead of THP-Hydroxyacetic acid.

Example 22

Figure 22:
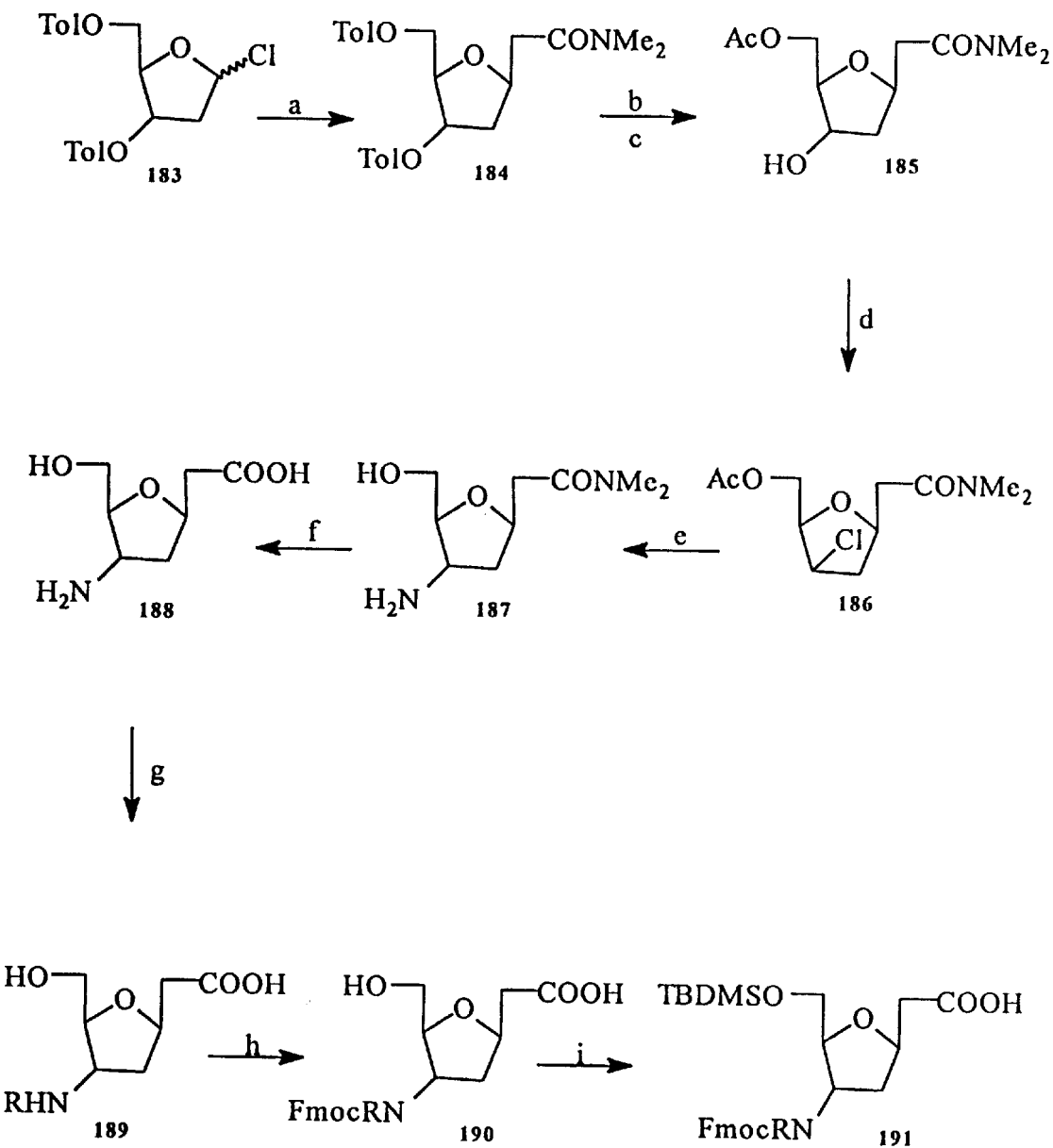

In FIG. 22, the building block 191 could be prepared using the known starting material 183 and following the reaction conditions depicted at the bottom of FIG. 22.

Example 23

Figure 23:
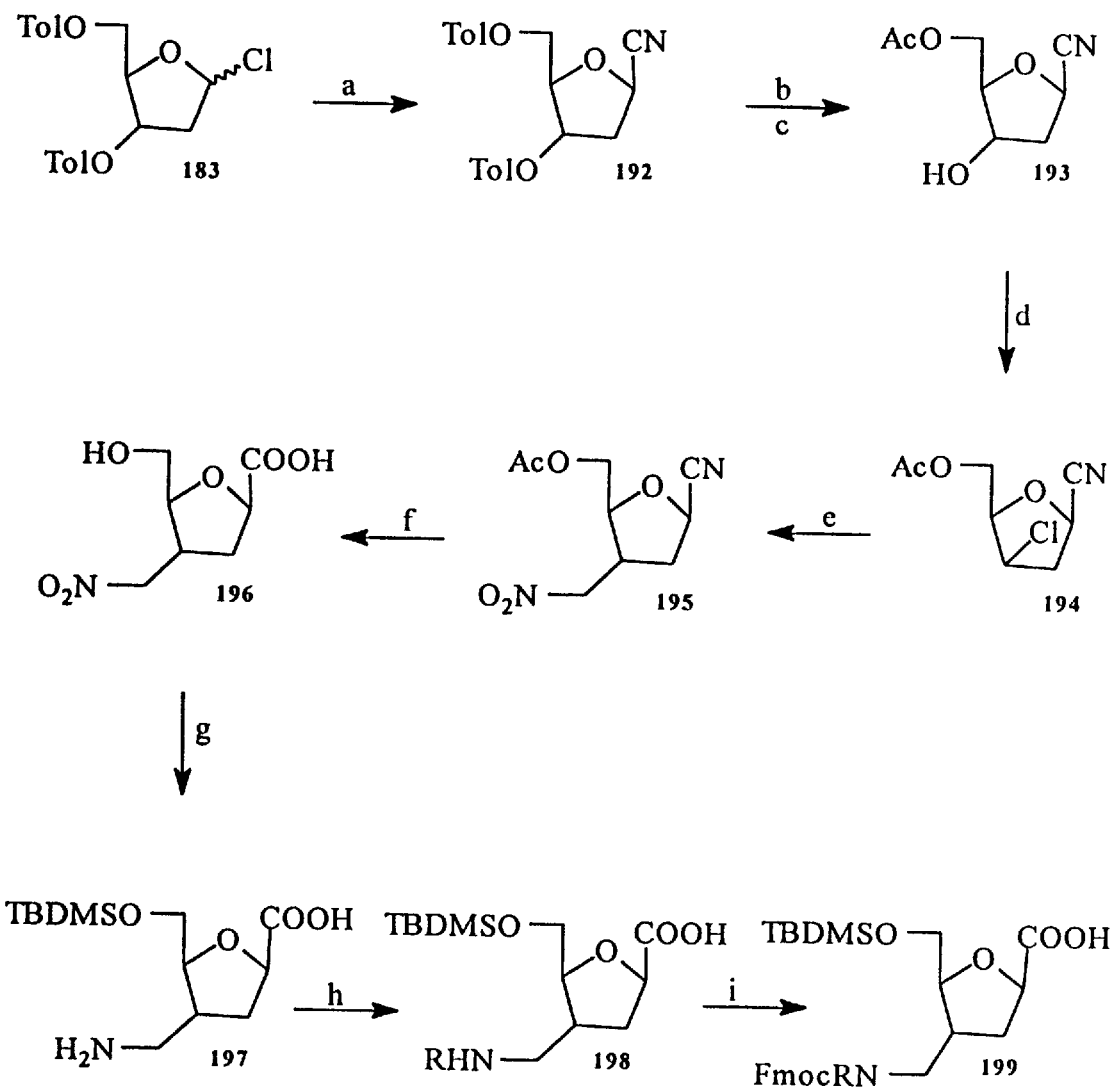

In FIG. 23, synthesis of the building block 199 could be accomplished utilizing the starting material 183 and following the reaction conditions depicted at the bottom of FIG. 23.

Example 24

Figure 24:
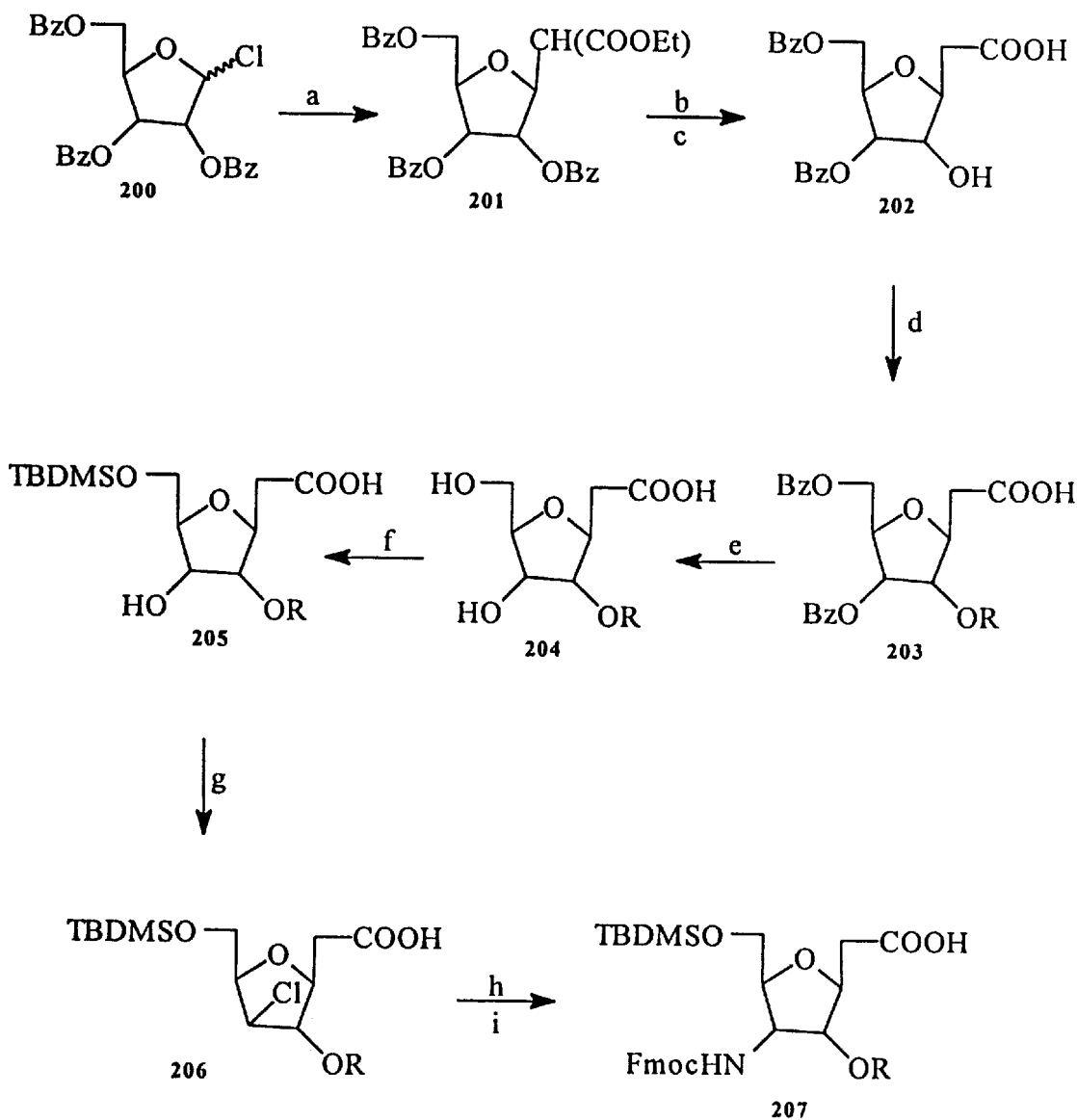
Figure 25:
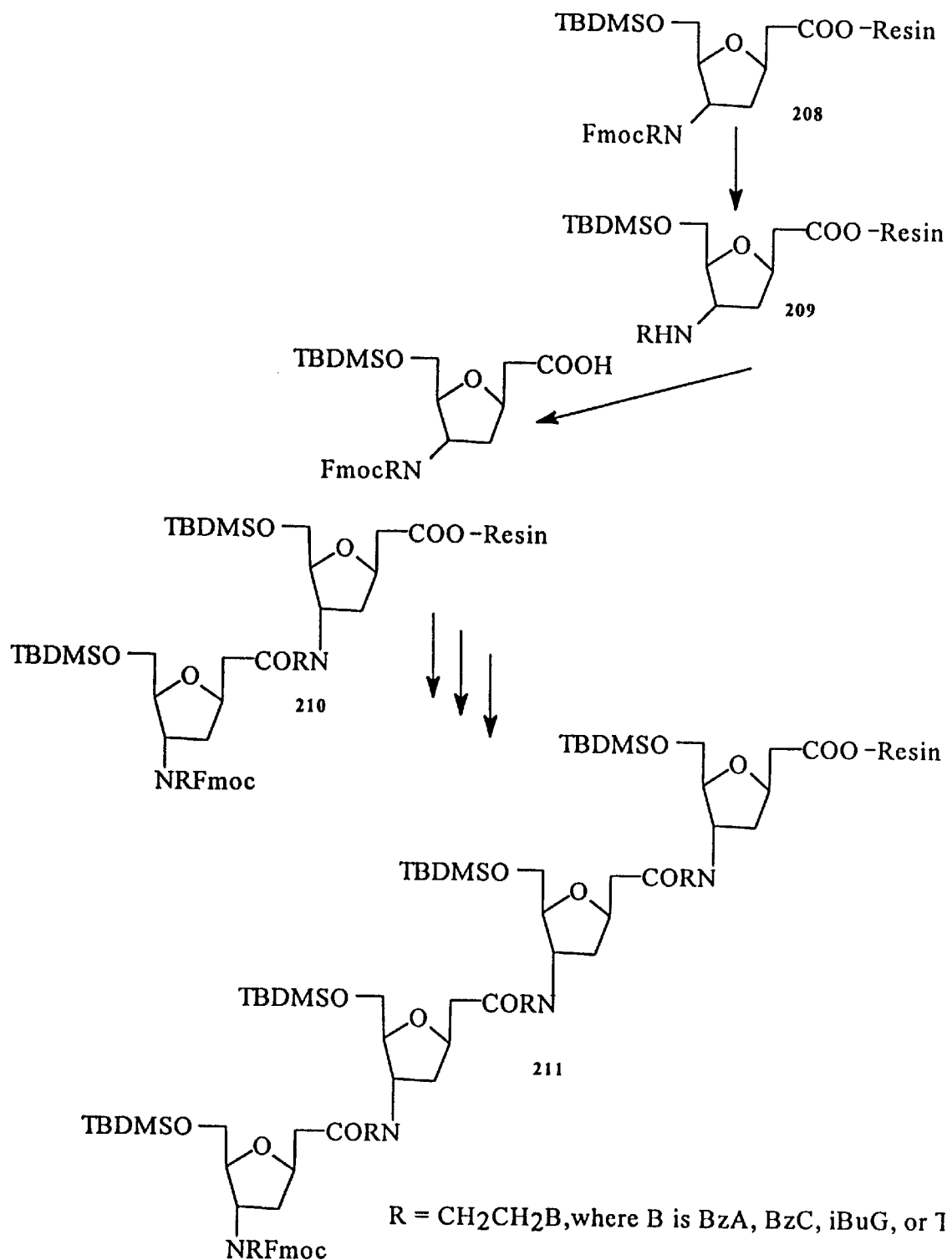

In FIG. 24, the starting material 200 is tranformed to the building block 207 by following the reaction conditions shown at the bottom of FIG. 24.

Example 25

The compounds used and generated in this example are shown in FIG. 1.

Serine (1)

Thymine (37.8 g, 300 mmol) was dissolved in a solution of potassium hydroxide (64.5 g, 1150 mmol) in 200 ml of water. While this solution was warmed in a 40° C. water bath, a solution of bromoacetic acid (62.5 g, 450 mmol) in 100 ml of water was added over 1 h period. The reaction was stirred of another 1 h at this temperature. It was allowed to cool to room temperature and the pH was adjusted to 5.5 with conc. HCl. The solution was then cooled in a refrigerator for 2 h. Any precipitate (unreacted thymine) formed was removed by filtration. The solution was then adjusted to pH 2 with conc. HCl and put in a freezer for 2 h. The white precipitate was collected by filtration and dried in a vacuum oven at 40° C. for 6 h. The yield was 44 g (88%).

N-Boc-L-Serine methyl ester (2)

L-Serine methyl ester (15.6 g, 100 mmol) was suspended in THF/DMF(100 ml each) mixture at room temperature. To this stirred mixture was added triethylamine (11.13 g, 110 mmol) followed by di-tert-butyl dicarbonate (24.0 g, 110 mmol) and the stirring continued at room temperature for 30 minutes. Water (20 ml) was added and the solution was stirred at room temperature for 8 h. The solution was evaporated to dryness. The residue was suspended in ethyl acetate (250 ml) and treated with potassium hydrogen sulfate (0.25N solution, 100 ml). The product was extracted immediately with ethyl acetate solution. The organic extract was washed with water (100 ml), brine (100 ml) and dried over anhydrous sodium sulfate. Evaporation of the organic solvent provided an oily residue of 26 g (90%).

N-Boc-L-Serine(OTHP) methyl ester (3)

The compound 2 (15 g, 68.49 mmol) was dissolved dry $CH_2Cl_2$ (100 ml) and treated with 3,4-dihydro-2H-pyran (8.4 g, 100 mmol) and catalytic amount of p-toluene sulfonic acid (100 mg) at room temperature. The reaction mixture was allowed to stir at room temperature for 12 h and evaporated to dryness. The residue was dissolved in ethyl acetate (200 ml), washed with 5% $NaHCO_3$ solution (100 ml), water (50 ml) and brine (50 ml). The organic extract was dried over anhydrous $Na_2SO_4$ and evaporated to dryness. The residue was pure enough for the next step and used as such. Yield 15 g (72%).

N-Boc-L-Serinol(OTEP) (4)

Serine(OTHP) methyl ester (10 g, 33 mmol) was dissolved in dry THF (100 ml) and cooled to 0° C. in an ice bath under argon atmosphere. To this cold stirred solution was added borane-methyl sulfide complex (2M solution in THF, 100 ml 200 mmol) during 1 h period at 0° C. temperature. After the addition of borane, the reaction mixture was warmed to room temperature and heated at 40° C. for 6 h. The reaction mixture was cooled to 0° C., neutralized with water and acetic acid to pH 6–7 and extracted with ether (3×100 ml). The ether extract was washed with water (2×100 ml) and brine (100 ml), dried over anhydrous $Na_2SO_4$ and evaporated to dryness to give a crude product as an oil. The oil on purification by flash column of silica gel using hexane→acetone as the eluent gave 8 g (88%) of pure product.

N-Boc-L-Serine(OTHP) OIb (5)

To a stirred solution of the compound 4 (8 g, 29.09 mmol) in dry $CH_2Cl_2$ (100 ml) at 0° C. was added TEA (3.54 g, 35 mmol) followed by isobutyryl chloride (3.71 g, 35 mmol) during 30 mins period. Then, the reaction mixture was stirred at room temperature for 4 h and evaporated to dryness. The residue was dissolved in EtOAc (200 ml), washed with 5% $NaHCO_3$ solution (50 ml), water (50 ml) and brine (50 ml). The organic extract was dried over anhydrous $Na_2SO_4$ and evaporated to dryness to give a crude product as an oil. The oil on purification by flash column of silica gel using hexane→acetone as the eluent gave 7.9 g (79%) of pure product.

L-Serinol(OIb) (6)

Compound 5 (10 g, 28.98 mmol) was dissolved in $CH_2Cl_2$ (100 ml) allowed to stir at room temperature with TFA (50 ml) for 1 h and evaporated to dryness. The residue was dissolved in methanol (50 ml) and evaporated again. The residue was dissolved in $CH_2Cl_2$ (200 ml), washed with sat. $NaHCO_3$ solution (2×100 ml), water (100 ml) and brine (50 ml). The organic extract was dried over anhydrous $Na_2SO_4$ and evaporated to dryness to give 4.5 g (96%) of the product as an oil.

N-(Thyminylacetyl)-L-Serinol(OIb) (8)

Thymine acetic acid 7 (7.3 g, 40 mmol) and N-methylmorpholine (4.4 ml, 40 mmol) were dissolved in 100 ml of DMF. The solution was allowed to cool to −20° C. under argon atmosphere. To this cold stirred solution, isobutyl chloroformate (5.2 ml, 40 mmol) was added in one portion. After 15 minutes, a solution of 6 (6.44 g, 40 mmol) in 30 ml of DMF (chilled to the same temperature) was added. The reaction mixture was stirred at −20° C. for 30 minutes, warmed to room temperature and the stirring continued for 1 h. The reaction mixture was evaporated to dryness and the residue dissolved in $CH_2Cl_2$ (200 ml). The organic solution was washed with 5% $NaHCO_3$ solution (100 ml), water (100 ml) and brine (50 ml). The organic extract was dried over anhydrous $Na_2SO_4$ and evaporated to dryness to give a crude product as foam. The crude product was purified by flash column of silica gel using $CH_2Cl_2$→acetone as the eluent to give 12 g (92%) of pure product.

4,4'-Dimethoxytrityl-N-(Thyminylacetyl)-L-Serinol(OIb) (9)

The compound 8 (10 g, 30.58 mmol) was coevaporated with dry pyridine (3×50 ml) and dissolved in dry pyridine (100 ml). To this solution was added TEA (3.54 g, 35 mmol) followed by DMTCl (11.83 g, 35 mmol) at room temperature under argon atmosphere. The reaction mixture was stirred for 12 h, quenched with methanol (20 ml) and stirred for 30 minutes. The solution was evaporated to dryness and dissolved in $CH_2Cl_2$ (200 ml). The organic extract was washed with 5% $NaHCO_3$ solution (100 ml), water (100 ml) and brine (50 ml). The $CH_2Cl_2$ layer was dried over anhydrous $Na_2SO_4$ and evaporated to dryness to give a crude product as foam. The crude product was purified by flash column of silica gel using $CH_2Cl_2$→acetone as the eluent to give 17 g (88%) of pure product.

1-O-(4,4'-Dimethoxytrityl)-2-[amino(thyminylacetyl)]-L-propan-1,3-diol (10)

The compound 9 (10 g, 15.89 mmol) was dissolved in methanol (20 ml). To this solution was added 1N NaOH solution (20 ml, 20 mmol) at 0° C. temperature. The reaction mixture was stirred for 1 h, quenched with acetic acid to pH 7. The solution was extracted with EtOAc (2×100 ml). The organic extract was washed with 5% $NaHCO_3$ solution (100 ml), water (100 ml) and brine (50 ml). The EtOAc layer was dried over anhydrous $Na_2SO_4$ and evaporated to dryness to give a crude product as foam. The crude product was purified by flash column of silica gel using $CH_2Cl_2$→acetone as the eluent to give 8.2 g 92%) of pure product.

1'-O-(4,4'-Dimethoxytrityl)-2-[amino(thyminylacetyl)-L-propan-3'-O-(N,N-diisopropyl)-β-cyanoethylphophoramidite (11)

The compound 10 (8.00 g, 14.31 mmol) was coevaporated with dry pyridine (3×50 ml) and dried over solid NaOH overnight under vacuum. The dried material was dissolved in dry $CH_2Cl_2$ (100 ml) and cooled to 0° C. under argon atmosphere. To this cold solution was added N,N-diisopropylethylamine (5.23 g, 25 mmol) followed by 2-cyanoethyl-N,N-diisopropylchlorophosphoramidite (4.72 g, 20.00 mmol) under argon atmosphere. The reaction mixture was stirred at 0° C. for 1 h and at room temperature for 1 h. The reaction mixture was diluted with $CH_2Cl_2$ (100 ml). The $CH_2Cl_2$ solution was washed with 5% $NaHCO_3$ solution (100 ml), water (100 ml) and brine (50 ml). The $CH_2Cl_2$ layer was dried over anhydrous $Na_2SO_4$ and evaporated to dryness to give a crude product as foam. The crude product was purified by flash column of silica gel using $CH_2Cl_2$→acetone containing 0.1% TEA as the eluent to give 10 g (x%) of pure product. The form was dried over solid NaOH in vacuum overnight. The form was dissolved in $CH_2Cl_2$ (15 ml) and dropped into stirred solution of dry hexanes (2000 ml) under argon during 1 h period. After the addition of $CH_2Cl_2$ solution, the precipitate that formed was stirred for additional 1 h and filtered, washed with dry hexanes (200 ml) and dried over solid NaOH overnight. Yield: 9.5 g (87%).

Example 26

(See FIG. 26)

N-(tert-Butyloxycarbonyl)-O-Benzyl-L-Serine (2)

O-Benzyl-L-Serine 1 (10 g, 51.28 mmol) was suspended in $THF/H_2O$ (8:2, 100 ml) mixture at room temperature. To this stirred mixture was added triethylamine (6.06 g, 60 mmol) followed by di-tert-butyl dicarbonate (13.08 g, 60 mmol), and the stirring continued at room temperature overnight. The homogenous solution was evaporated to dryness and the residue dissolved in ethyl acetate (300 ml). The organic extract was washed with 0.5N solution of potassium hydrogen sulfate (100 ml), water (100 ml) and brine (50 ml). The ethyl acetate extract was dried over anhydrous sodium sulfate and evaporated to dryness to give 14 g (93%) of an oily residue.

N-(tert-Butyloxycarbonyl)-O-Benzyl-L-Serinol (3)

N-(tert-butyloxycarbonyl)-O- benzyl-L-serine 2 (6.0 g, 20.34 mmol) was dissolved in dry THF and cooled to −20° C. under argon atmosphere. To this cold stirred solution was added TEA (2.32 g, 23 mmol) and isobutyl chloroformate (3.13 g, 23 mmol). The stirring was continued for 30 min at −20° C. under argon atmosphere. The reaction mixture was filtered immediately under a blanket of argon, the precipitate was washed with dry THF (50 ml). The combined filtrate was added slowly into a cold (0° C.) solution of $NaBH_4$ (7.4 g, 200 mmol) in THF/water (80:20, 200 ml) during 10 min period. After the addition, the reaction mixture was stirred for 2 h at 0° C. and the pH adjusted to 7 with acetic acid. The solution was evaporated to dryness, partitioned between ethyl acetate/water (300:150 ml) and extracted in ethyl acetate. The organic extract was washed with brine (100 ml), dried over anhydrous sodium sulfate and evaporated to dryness. The crude product was purified by flash column chromatography over silica gel using $CH_2Cl_2 \rightarrow EtOAc$ as the eluent. The pure product was pooled together and evaporated to dryness to give 4.7 g (82%) of the pure product as an oil. $^1HNMR$ ($CDCl_3$): $\delta 1.41$ (s, 9H, Boc), 3.60–3.70 (m, 4H), 3.82 (d, 2H), 4.53 (s, 2H, $OCH_2Ph$), 5.20 (bs, 1H, NH) and 7.30–7.40 (m, 5H, Ph).

N-(tert-Butyloxycarbonyl)-O-Benzyl-L-Serinol-O-Ib (4)

To a dried solution of N-(tert-butyloxycarbonyl)-O-benzyl-L-serinol 3 (4.3 g, 14.3 mmol) in dry pyridine (50 ml) was added TEA (2.02 g, 20 mmol) at room temperature. To this stirred solution was added isobutyric anhydride (3.16 g, 20 mmol) and the stirring continued overnight under argon atmosphere. The reaction mixture was evaporated to dryness, partitioned between EtOAc (100 ml) and $NaHCO_3$ (5% solution, 100 ml), and extracted in EtOAc. The organic extract was washed with water (100 ml), brine (50 ml), and dried over anhydrous $Na_2SO_4$. The dried solution was evaporated to dryness to give a crude residue. The residue was purified by flash chromatography over silica gel using hexane→EtOAc as the eluent. The pure fractions were pooled together and evaporated to give an oily product 4.5 g (84%). $^1HNMR$ ($CDCl_3$): $\delta 1.04$ (d, 6H, $IbCH_3$), 1.39 (s, 9H, Boc), 2.46 (m, 1H, IbCH), 3.40 (m, 2H), 3.92 (m, 2H), 4.12 (m, 1H), 4.46 (s, 2H, $OCH_2Ph$), 6.84 (d, 1H, NH) and 7.24–7.40 (m, 5H, Ph).

N-(Thyminylacetyl)-O-Benzyl-L-Serinol-O-Ib (6)

N-(tert-Butyloxycarbonyl)-O-benzyl-L-serinol-O-Ib 4 (4.3 g, 12.25 mmol) was allowed to stir at room temperature in trifluoro acetic acid (20 ml) and $CH_2Cl_2$ (20 ml) for 30 min. The reaction mixture was evaporated to dryness, dissolved in dry $CH_3OH$ (10 ml) and evaporated again to dryness. The residue was dried over solid KOH under vacuum for 12 h. The dried residue was used as such for further reaction without characterization.

Thymine acetic acid 5 (2.76 g, 15 mmol) was dissolved in dry DMF (75 ml) and cooled to −20° C. under argon. To this cold stirred solution was added N-methylmorpholine (1.72 g, 17 mmol) followed by isobutyl chloroformate (2.31 g, 17 mmol). After 15 min of stirring, a solution of the above TFA salt in dry DMF (50 ml) was neutralized with N-methylmorpholine (1.72 g, 17 mmol) and added into the cold stirred solution of thymine acetic acid at once. The reaction mixture was stirred at −20° C. for 1 h, warmed to room temperature and the stirring continued overnight. The solution was evaporated to dryness and the residue dissolved in $CH_2Cl_2$ (250 ml) and water (100 ml), and extracted in $CH_2Cl_2$. The organic extract was washed with 5% $NaHCO_3$ solution (100 ml), water (100 ml) and brine (50 ml). The $CH_2Cl_2$ extract was dried and evaporated to dryness to give crude product. The crude product was purified by flash chromatography over silica gel using $CH_2Cl_2 \rightarrow$ acetone as the eluent. The necessary fractions were collected and evaporated to give 4.8 g (94%) of the pure product. The pure product was crystallized from $CH_2Cl_2$/hexane. mp: 122–124° C. $^1HNMR$ ($CDCl_3$): $\delta 1.04$ (d, 6H, $IbCH_3$), 1.72 (s, 3H, $CH_3$), 2.44 (m, 1H, IbCH), 3.42 (m, 2H), 4.06 (m, 2H), 4.18 (m, 1H), 4.30 (s, 2H), 4.46 (s, 2H, $OCH_2Ph$), 7.24–7.40 (m, 6H, $C_6H$ and Ph), 8.22 (d, 1H, NH) and 11.22 (s, 1H, NH).

N-(Thyminylacetyl)-L-Serinol-O-Ib (7)

N-(Thyminylacetyl)-O-Benzyl-L-Serinol-O-Ib 6 (2.08 g, 5 mmol) was dissolved in ethanol (50 ml). To this solution $Pd(OH)_2$ (0.6 g) and cyclohexene (5 ml) were added at room temperature. The reaction mixture was heated at 70° C. for 12 h. The catalyst was filtered, washed with methanol (20 ml). The filtrate was evaporated to dryness to give a white solid. The white solid was dissolved in minimum amount of MeOH and cooled to room temperature. The product crystallized as fine powder. mp: 196–198° C. Yield: 1.48 g (91%). $^1HNMR$ ($Me_2SO-d_6$): $\delta 1.04$ (d, 6H, $IbCH_3$), 1.72 (s, 3H, $CH_3$), 2.42 (m, 1H, IbCH), 3.40 (m, 2H), 3.94 (m, 2H), 4.06 (m, 1H), 4.28 (s, 2H), 4.90 (t, 1H, OH), 7.20 (s, 1H, $C_6H$), 8.12 (d, 1H, NH) and 11.22 (s, 1H, NH).

4,4'-Dimethoxytrityl-N-(Thyminylacetyl)-L-Serinol-O-Ib (8):

N-(Thyminylacetyl)-L-Serinol-O-Ib 7 (1.48 g, 4.5 mmol) was dissolved in dry pyridine (50 ml) under argon. To this stirred solution was added TEA (0.51 g, 5 mmol) and N,N-dimethylamino pyridine (0.10 g). After 10 min, 4,4'-di-methoxytrityl chloride (1.69 g, 5 mmol) was added and the stirring continued at room temperature under argon for overnight. The reaction mixture was quenched with MeOH (10 ml), stirred for 10 min and evaporated to dryness. The residue was dissolved in EtOAc (200 ml), washed with 5% $NaHCO_3$ solution (100 ml), water (100 ml) and brine (50 ml). The organic extract was dried over anhydrous $Na_2SO_4$ and evaporated to dryness. The crude product was purified by flash column chromatography over silica gel using $CH_2Cl_2 \rightarrow EtOAc$ as the eluent. The pure fractions were pooled and evaporated to give 2.5 g (88%) of foam. $^1HNMR$ ($CDCl_3$): $\delta 1.04$ (d, 6H, $IbCH_3$), 1.72 (s, 3H, $CH_3$), 2.40 (m, 1H, IbCH), 3.38 (m, 2H), 3.72 (s, 6H, $2.OCH_3$), 4.12 (m, 2H), 4.20 (m, 1H), 4.32 (d, 2H), 6.84 (m, 4H, Ph), 7.20–7.40 (m, 12H, $C_6H$ and Ph), 8.30 (d, 1H, NH) and 11.28 (s, 1H, NH).

1-O-(4,4'-Dimethoxytrityl)-2-[amino(thyminylacetyl)]-L-propan-1,3-diol (9)

4,4'-Dimethoxytrityl-N-(Thyminylacetyl)-L-Serinol-O-Ib 8 (3.4 g, 5.41 mmol) was dissolved in MeOH (30 ml) and cooled to 0° C. in an ice bath. To this cold stirred solution was added 2N NaOH (10 ml, 20 mmol) and the stirring continued for 30 min at 0° C. The pH of the solution was adjusted to 7 with acetic acid and evaporated to dryness. The residue was partitioned between water (50 ml) and $CH_2Cl_2$ (150 ml) and extracted in $CH_2Cl_2$. The aqueous layer was extracted again with $CH_2Cl_2$ (50 ml). The combined organic extract was washed with brine (50 ml), dried and evaporated to dryness. The residue was purified by flash column chromatography over silica gel using $CH_2Cl_2 \rightarrow$ acetone as the eluent. Yield: 3.0 g (99%). $^1HNMR$ ($CDCl_3$): 1.72 (s, 3H, $CH_3$), 3.0 (m, 2H), 3.42 (m, 2H), 3.72 (s, 6H, 2.$OCH_3$), 3.94 (m, 1H), 4.32 (d, 2H), 4.68 (m, 1H, OH), 6.84 (m, 4H, Ph), 7.20–7.40 (m, 12H, $C_6H$ and Ph), 8.06 (d, 1H, NH) and 11.28 (bs, 1H, NH).

1-O-(4,4'-Dimethoxytrityl)-2-[amino(thyminylacetyl)]-L-propan-3-O-(N,N-diisopropyl)-β-cyanoethylphosphoramidite (10)

1-O-(4,4'-Dimethoxytrityl)-2-[amino(thyminylacetyl)]-L-propan-1,3-diol 9 (3.1 g, 5.55 mmol) was dried over solid NaOH under vacuum overnight and dissolved in dry $CH_2Cl_2$ (100 ml). The solution was cooled to 0° C. under argon atmosphere. To this cold stirred solution was added N,N-diisopropylethylamine (1.29 g, 10 mmol) followed by 2-cyanoethyl-N,N-diisopropyl-chlorophophoramidite (1.96 g, 8.3 mmol). The reaction mixture was stirred at 0° C. for 1 h and at room temperature for 2 h. The reaction was diluted with $CH_2CH_2$ (100 ml) and the organic layer was washed with 5% $NaHCO_3$ solution (100 ml), water (100 ml) and brine (50 ml). The $CH_2Cl_2$ extract was dried and evaporated to dryness to give an oily residue. The residue was purified by flash chromatography over silica gel using $CH_2Cl_2$→EtOAc containing 0.1% TEA as the eluent. The pure fractions were pooled together and evaporated to give a foam. The foam was dried over solid NaOH under vacuum overnight. The dried foam was dissolved in dry $CH_2Cl_2$ (20 ml) and dropped into a stirred solution of dry hexane (2000 ml) under argon during 1h period. After the addition, the precipitate formed was stirred for additional 1h and filtered, washed with dry hexane (100 ml) and the solid was dried over solid NaOH under vacuum for 4 h. Yield: 3.5 g (83%).

Example 27

Figure 27:
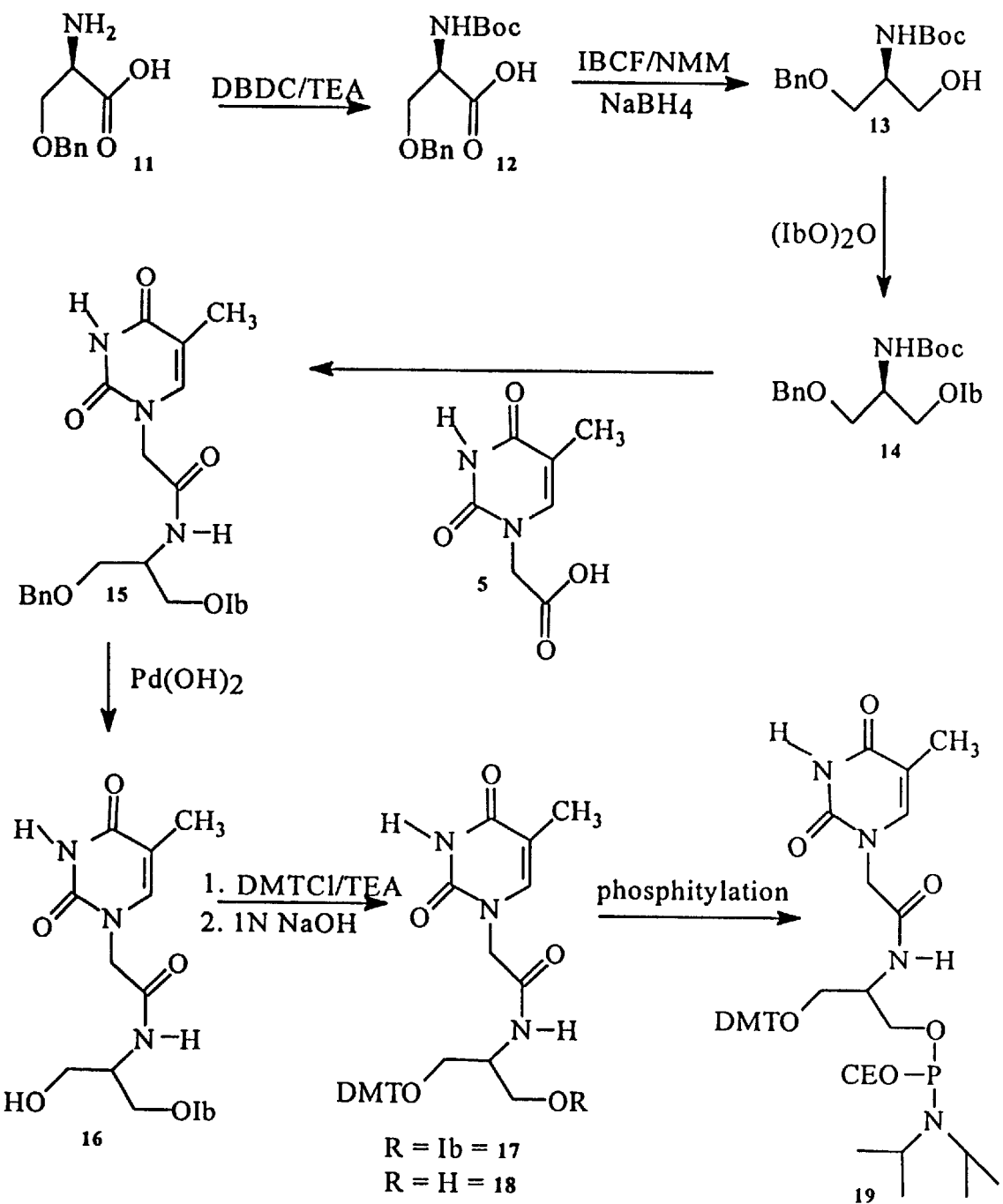
FIG. 27 shows the synthesis of 1-O-(4,4'-Dimethoxytrityl)-2-[amino(thyminylacetyl)]-D-propan-3-O-(N,N-diisopropyl)-β-cyanoethylphosphoramidite.
Figure 28:
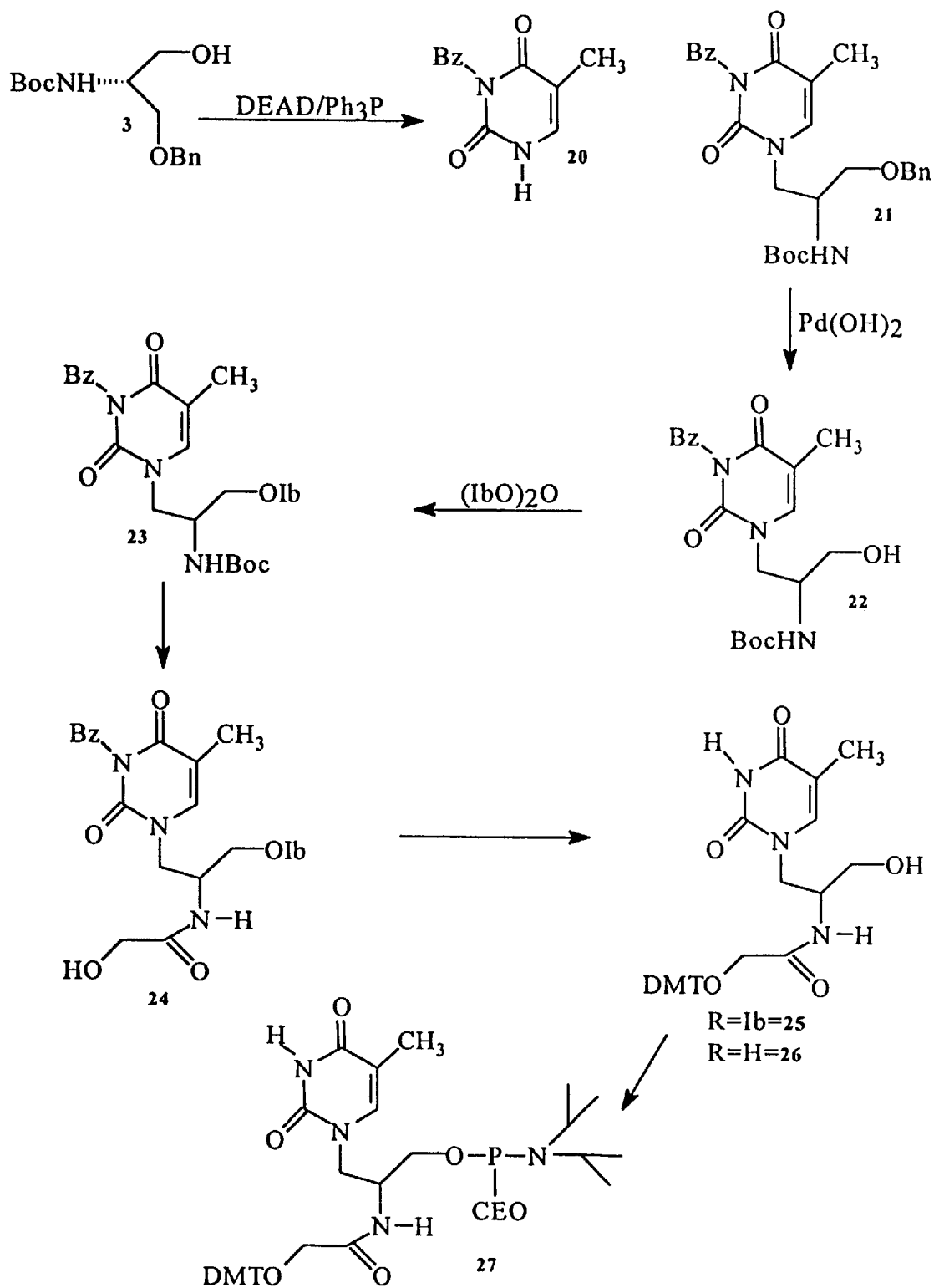
FIG. 28 shows the synthesis of 2-[(β-(4,4'-Dimethoxytrityl)-O-acetyl)amino]-3-thyminyl-L-propan-1-O-(N,N-diisopropyl)-β-cyanoethylphosphoramidite.
Figure 29:
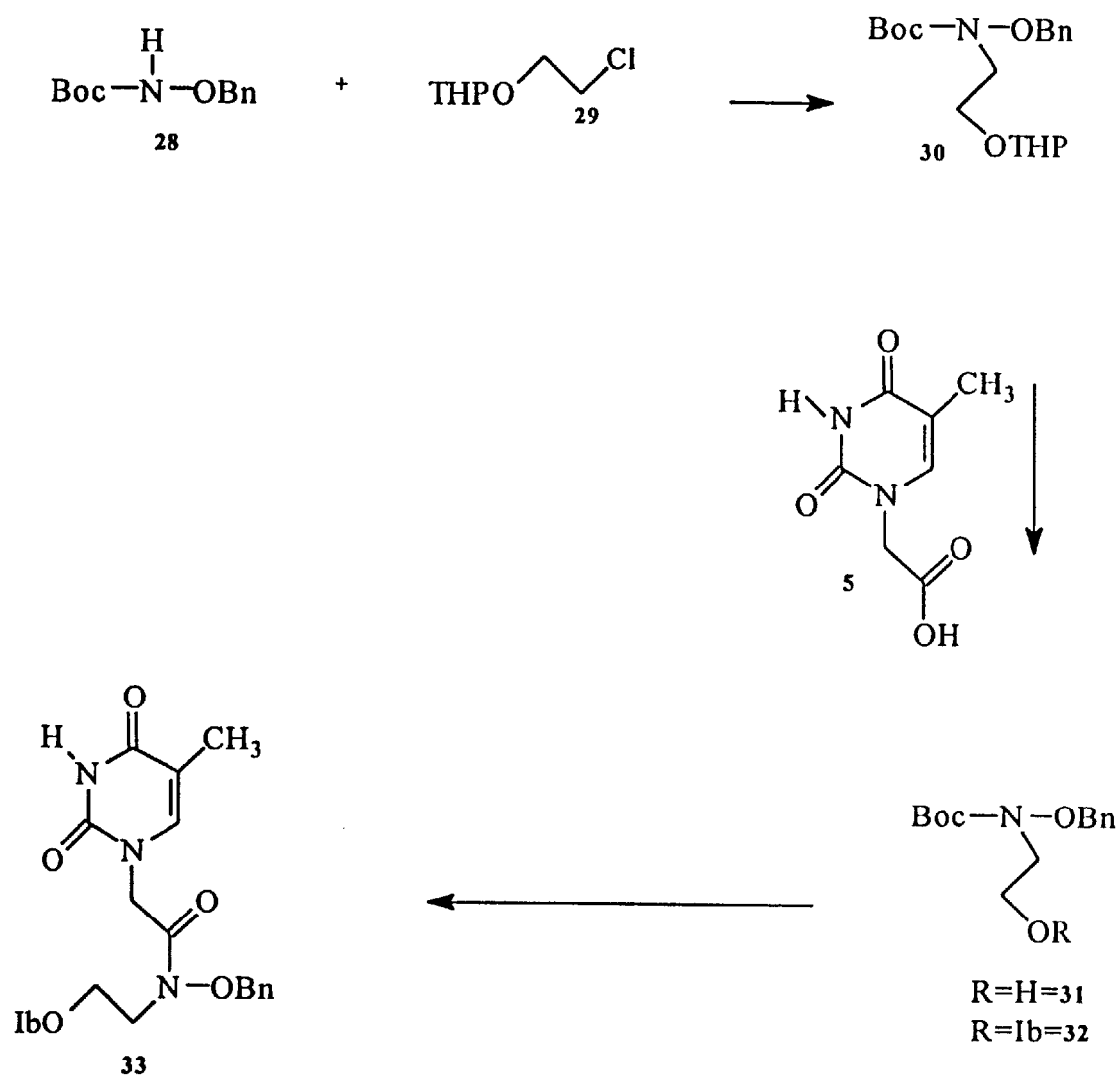
FIG. 29 shows the synthesis of N-(Thyminylacetyl)-N-[[(2-isobutyryl)oxy]ethyl]-O-benzylhydroxylamine.
Figure 30:
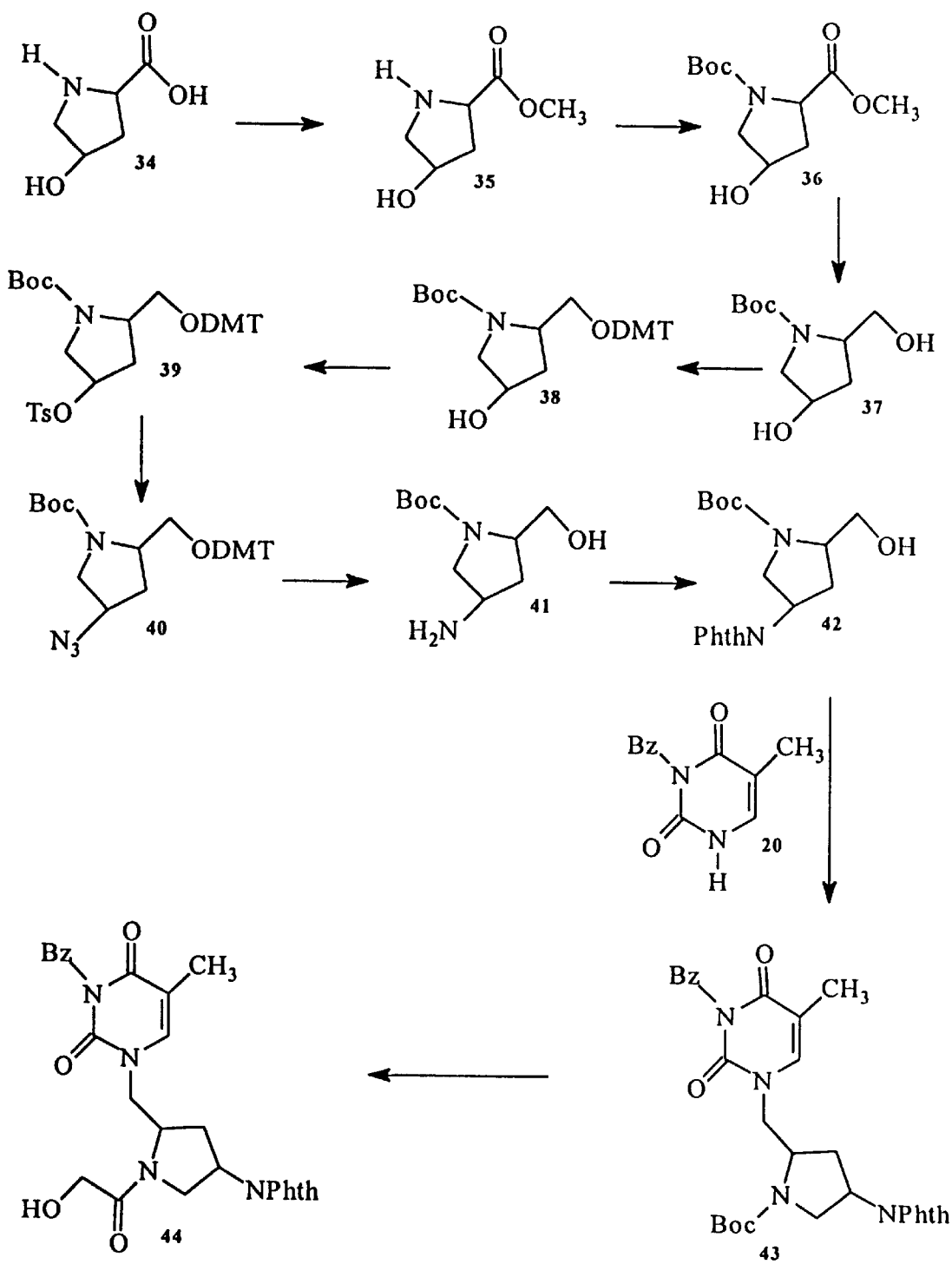
FIG. 30 shows the synthesis of (2R,4S)-1-(tert-Butyloxycarbonyl)-2-[N$_3$-benzoyl (thymin-1-yl)]methyl-4-phthalim ido-pyrrolidine.

(See FIG. 27)

N-(tert-Butyloxycarbonyl)-O-Benzyl-D-Serine (12)

O-Benzyl-D-Serine 11 (5 g, 25.64 mmol) was suspended in THF/$H_2O$ (8:2, 70 ml) mixture at room temperature. To this stirred mixture was added triethylamine (4.04 g, 40 mmol) followed by di-tert-butyl dicarbonate (6.54 g, 30 mmol), and the stirring continued at room temperature overnight. The homogenous solution was evaporated to dryness and the residue dissolved in ethyl acetate (150 ml). The organic extract was washed with 0.5N solution of potassium hydrogen sulfate (100 ml), water (100 ml) and brine (50 ml). The ethyl acetate extract was dried over anhydrous sodium sulfate and evaporated to dryness to give 7.56 g (100%) of an oily residue.

N-(tert-Butyloxycarbonyl)-O-Benzyl-D-Serinol (13)

N-(tert-Butyloxycarbonyl)-O-benzyl-D-serine 10 (7.56 g, 25.63 mmol) was dissolved in dry THF and cooled to –20° C. under argon atmosphere. To this cold stirred solution was added TEA (3.03 g, 30 mmol) and isobutyl chloroformate (4.08 g, 30 mmol). The stirring was continued for 30 min at –20° C. under argon atmosphere. The reaction mixture was filtered immediately under a blanket of argon, the precipitate was washed with dry THF (50 ml). The combined filtrate was added slowly into a cold (0° C.) solution of $NaBH_4$ (7.4 g, 200 mmol) in THF/water (80:20, 200 ml) during 10 min period. After the addition, the reaction mixture was stirred for 2 h at 0° C. and the pH adjusted to 7 with acetic acid. The solution was evaporated to dryness, partitioned between ethyl acetate/water (300:150 ml) and extracted in ethyl acetate. The organic extract was washed with brine (100 ml), dried over anhydrous sodium sulfate and evaporated to dryness. The crude product was purified by flash column chromatography over silica gel using $CH_2Cl_2$→EtOAc as the eluent. The pure product was pooled together and evaporated to dryness to give 6.68 g (92%) of the pure product as an oil. $^1$HNMR ($CDCl_3$): δ1.41 (s, 9H, Boc), 3.60–3.70 (m, 4H), 3.82 (d, 2H), 4.53 (s, 2H, $OCH_2Ph$), 5.20 (bs, 1H, NH) and 7.30–7.40 (m, 5H, Ph).

N-(tert-Butyloxycarbonyl)-O-Benzyl-D-Serinol-O-Ib (14)

To a dried solution of N-(tert-Butyloxycarbonyl)-O-benzyl-D-serinol 13 (6.6 g, 23.5 mmol) in dry pyridine (50 ml) was added TEA (3.03 g, 30 mmol) at room temperature. To this stirred solution was added isobutyric anhydride (4.74 g, 30 mmol) and the stirring continued overnight under argon atmosphere. The reaction mixture was evaporated to dryness, partitioned between EtOAc (200 ml) and $NaHCO_3$ (5% solution, 100 ml), and extracted in EtOAc. The organic extract was washed with water (100 ml), brine (50 ml), and dried over anhydrous $Na_2SO_4$. The dried solution was evaporated to dryness to give a crude residue. The residue was purified by flash chromatography over silica gel using hexane→EtOAc as the eluent. The pure fractions were pooled together and evaporated to give an oily product 8.0 g (97%). $^1$HNMR ($CDCl_3$): δ1.04 (d, 6H, $IbCH_3$), 1.39 (s, 9H, Boc), 2.46 (m, 1H, IbCH), 3.40 (m, 2H), 3.92 (m, 2H), 4.12 (m, 1H), 4.46 (s, 2H, $OCH_2Ph$), 6.84 (d, 1H, NH) and 7.24–7.40 (m, 5H, Ph).

N-(Thyminylacetyl)-O-Benzyl-D-Serinol-O-Ib (15)

N-(tert-Butyloxycarbonyl)- O-benzyl-D-serinol-O-Ib 14 (5.0 g, 14.25 mmol) was allowed to stir at room temperature in trifluoro acetic acid (20 ml) and $CH_2Cl_2$ (20 ml) for 30 min. The reaction mixture was evaporated to dryness, dissolved in dry $CH_3OH$ (10 ml) and evaporated again to dryness. The residue was dissolved in $CH_2Cl_2$ (150 ml), the pH was adjusted to 7 with 5% $NaHCO_3$ solution and extracted in $CH_2Cl_2$. The organic layer was washed with water (50 ml) and brine (50 ml). The $CH_2Cl_2$ extract was dried and evaporated to dryness. The residue that obtained was dried over solid KOH under vacuum for 12 h. The dried residue was used as such for further reaction without characterization.

Thymine acetic acid 5 (2.57 g, 14 mmol) was dissolved in dry DMF (50 ml) and cooled to –20° C. under argon. To this cold stirred solution was added N-methylmorpholine (1.52 g, 15 mmol) followed by isobutyl chloroformate (2.04 g, 15 mmol). After 15 min of stirring, a solution of the above amine in dry DMF (50 ml) was added into the cold stirred solution of thymine acetic acid at once. The reaction mixture was stirred at –20° C. for 1 h, warmed to room temperature and the stirring continued overnight. The solution was evaporated to dryness and the residue dissolved in $CH_2Cl_2$ (250 ml) and water (100 ml), and extracted in $CH_2Cl_2$. The organic extract was washed with 5% $NaHCO_3$ solution (100 ml), water (100 ml) and brine (50 ml). The $CH_2Cl_2$ extract was dried and evaporated to dryness to give crude product. The crude product was purified by flash chromatography over silica gel using $CH_2Cl_2$→acetone as the eluent. The necessary fractions were collected and evaporated to give 2.8 g (54%) of the pure product. $^1$HNMR ($CDCl_3$): δ1.04 (d, 6H, $IbCH_3$), 1.72 (s, 3H, $CH_3$), 2.44 (m, 1H, IbCH), 3.42 (m, 2H), 4.06 (m, 2H), 4.18 (m, 1H), 4.30 (s, 2H), 4.46 (s, 2H, $OCH_2Ph$), 7.24–7.40 (m, 6H, $C_6H$ and Ph), 8.22 (d, 1H, NH) and 11.22 (s, 1H, NH).

The titled compound was also prepared by using the method described for the preparation "L" isomer. Reagents Used: Thymine acetic acid (2.2 g, 12 mmol); Isobutyl chloroformate (1.77 g, 13 mmol); N-methylmorpholine (1.52 g, 15 mmol); TFA salt (3.65 g, 10 mmol); N-methylmorpholine (1.5 g, 15 mmol) and dry DMF (100 ml). Yield: 3.5 g (84%).

N-(Thyminylacetyl)-D-Serinol-O-Ib (16)

N-(Thyminylacetyl)-O-Benzyl-D-Serinol-O-Ib 15 (3.5 g, 8.39 mmol) was dissolved in ethanol (50 ml). To this solution Pd(OH)$_2$ (1.00 g) and cyclohexene (10 ml) were added at room temperature. The reaction mixture was heated at 70° C. for 12 h. The catalyst was filtered, washed with methanol (20 ml). The filtrate was evaporated to dryness to give an white solid. Yield: 2.7 g (98%). $^1$HNMR (Me$_2$SO-d$_6$): δ1.04 (d, 6H, IbCH$_3$), 1.72 (s, 3H, CH$_3$), 2.42 (m, 1H, IbCH), 3.40 (m, 2H), 3.94 (m, 2H), 4.06 (m, 1H), 4.28 (s, 2H), 4.90 (t, 1H, OH), 7.20 (s, 1H, C$_6$H), 8.12 (d, 1H, NH) and 11.22 (s, 1H, NH).

4,4'-Dimethoxytrityl-N-(Thyminylacetyl)-D-Serinol-O-Ib (17)

N-(Thyminylacetyl)-D-Serinol-O-Ib 16 (2.7 g, 8.26 mmol) was dissolved in dry pyridine (50 ml) under argon. To this stirred solution was added TEA (1.01 g, 10 mmol) followed by 4,4'-dimethoxytrityl chloride (3.38 g, 10 mmol) and the stirring continued at room temperature under argon for overnight. The reaction mixture was quenched with MeOH (10 ml), stirred for 10 min and evaporated to dryness. The residue was dissolved in EtOAc (250 ml), washed with 5% NaHCO$_3$ solution (100 ml), water (100 ml) and brine (50 ml). The organic extract was dried over anhydrous Na$_2$SO$_4$ and evaporated to dryness. The crude product was purified by flash column chromatography over silica gel using CH$_2$Cl$_2$→EtOAc as the eluent. The pure fractions were pooled and evaporated to give 5.0 g (96%) of foam. $^1$HNMR (CDCl$_3$): δ1.04 (d, 6H, IbCH$_3$), 1.72 (s, 3H, CH$_3$), 2.40 (m, 1H, IbCH), 3.38 (m, 2H), 3.72 (s, 6H, 2.OCH$_3$), 4.12 (m, 2H), 4.20 (m, 1H), 4.32 (d, 2H), 6.84 (m, 4H, Ph), 7.20–7.40 (m, 12H, C$_6$H and Ph), 8.30 (d, 1H, NH) and 11.28 (s, 1H, NH).

1-O-(4,4'-Dimethoxytrityl)-2-[amino(thyminylacetyl)]-D-propan-1,3-diol (18)

4,4'-Dimethoxytrityl-N-(Thyminylacetyl)-D-Serinol-O-Ib 17 (5.0 g, 7.95 mmol) was dissolved in MeOH (30 ml) and cooled to 0° C. in an ice bath. To this cold stirred solution was added 2N NaOH (10 ml, 20 mmol) and the stirring continued for 30 min at 0° C. The pH of the solution was adjusted to 7 with acetic acid and evaporated to dryness. The residue was partitioned between water (50 ml) and CH$_2$Cl$_2$ (250 ml) and extracted in CH$_2$Cl$_2$. The aqueous layer was extracted again with CH$_2$Cl$_2$ (50 ml). The combined organic extract was washed with brine (50 ml), dried and evaporated to dryness. The residue was purified by flash column chromatography over silica gel using CH$_2$Cl$_2$→acetone as the eluent. Yield: 4.0 g (90%). $^1$HNMR (CDCl$_3$): 1.72 (s, 3H, CH$_3$), 3.0 (m, 2H), 3.42 (m, 2H), 3.72 (s, 6H, 2.OCH$_3$), 3.94 (m, 1H), 4.32 (d, 2H), 4.68 (m, 1H, OH), 6.84 (m, 4H, Ph), 7.20–7.40 (m, 12H, C$_6$H and Ph), 8.06 (d, 1H, NH) and 11.28 (bs, 1H, NH)

1-O-(4,4'-Dimethoxytrityl)-2-[amino(thyminylacetyl)]-D-propan-3-O-(N,N-diisopropyl)-β-cyanoethylphosphoramidite (19)

1-O-(4,4'-Dimethoxytrityl)-2-[amino(thyminylacetyl)]-D-propan- 1,3-diol 18 (2.79 g, 5.0 mmol) was dried over solid NaOH under vacuum overnight and dissolved in dry CH$_2$Cl$_2$ (100 ml). The solution was cooled to 0° C. under argon atmosphere. To this cold stirred solution was added N,N-diisopropylethylamine (1.29 g, 10 mmol) followed by 2-cyanoethyl-N, N-diisopropylchlorophosphoramidite (1.96 g, 8.3 mmol). The reaction mixture was stirred at 0° C. for 1 h and at room temperature for 2 h. The reaction was diluted with CH$_2$Cl$_2$ (100 ml) and the organic layer was washed with 5% NaHCO$_3$ solution (100 ml), water (100 ml) and brine (50 ml). The CH$_2$Cl$_2$ extract was dried and evaporated to dryness to give an oily residue. The residue was purified by flash chromatography over silica gel using CH$_2$Cl$_2$→EtOAc containing 0.1% TEA as the eluent. The pure fractions were pooled together and evaporated to give a foam. The foam was dried over solid NaOH under vacuum overnight. The dried foam was dissolved in dry CH$_2$Cl$_2$ (20 ml) and dropped into a stirred solution of dry hexane (2000 ml) under argon during 1h period. After the addition, the precipitate formed was stirred for additional 1h and filtered, washed with dry hexane (100 ml) and the solid was dried over solid NaOH under vacuum for 4 h. Yield: 3.3 g (87%).

Example 28

(FIG. 28)

1-O-Benzyl-2-[(tert-butyloxycarbonyl)amino]-3-[N$_3$-benzoyl(thyminyl)-L-propanol (21)

To a stirred solution of N$_3$-benzoylthymine 20 (5.75 g, 25 mmol) in dry THF (200 ml) under argon was added triphenyl phosphine (10.48 g, 40 mmol) and N$_\alpha$-tert-butyloxycarbonyl-β-benzyloxy-L-serinol 3 (5.3 g, 18.86 mmol) at room temperature. After 15 min, diethylazodicarboxylate (6.96 g, 40 mmol) was added slowly during 30 min period. The reaction mixture was covered with aluminum foil and allowed to stir at room temperature under argon for 24 h. The solvent was evaporated to dryness and the residue dissolved in EtOAc (300 ml). The organic extract was washed with 5% NaHCO$_3$ solution (100 ml), water (100 ml) and brine (100 ml), and dried over anhydrous Na$_2$SO$_4$. The dried EtOAc extract was evaporated to dryness to give an orange oil. The crude product was purified by flash chromatography over silica gel using hexane→EtOAc as the eluent. The fraction having the required product was pooled and evaporated to give a pale pink oil. Yield: 8.0 g (86%). $^1$HNMR (CDCl$_3$): 1.41 (s, 9H, Boc), 1.72 (s, 3H, CH$_3$), 3.56 (m, 2H), 4.20 (m, 2H), 4.32 (m, 1H), 4.52 (d, 2H, OCH$_2$Ph), 5.20 (d, 1H, NH), 7.06 (s, 1H, C$_6$H) and 7.20–7.60 (m, 10H, Ph).

2-(tert-Butyloxycarbonyl) amino]-3-[N$_3$-benzoyl (thyminyl)-L-propan-1-ol (22)

1-O-Benzyl-2-[(tert-butyloxy-carbonyl)amino]-3-[N$_3$-benzoyl(thyminyl)-L-propanol 21 (4.93 g, 10 mmol) was dissolved in MeOH (100 ml) and treated with Pd/C (10%, 1 g). The reaction mixture was hydrogenated at 50 psi of hydrogen for 12 h. The catalyst was filtered, washed with MeOH (50 ml) and the filtrate was evaporated to dryness. The residue was crystallized from acetone/hexane to give 3.70 g (92%) of pure product. mp: 156–159° C. $^1$HNMR (CDCl$_3$): 1.42 (s, 9H, Boc), 1.94 (s, 3H, CH$_3$), 3.64 (m, 4H), 3.84 (m, 1H), 4.14 (m, 1H), 5.22 (d, 1H, NH), 7.18 (s, 1H, C$_6$H), 7.48 (t, 2H, Ph), 7.62 (t, 1H, Ph) and 7.98 (d, 2H, Ph).

1-O-Isobutyryl-2-[(tert-butyloxycarbonyl)amino]-3-[N$_3$-benzoyl (thyminyl)-L-propanol (23)

2-[(Tert-Butyloxycarbonyl)amino]-3-[N$_3$-benzoyl (thyminyl)-L-propan-1-ol 22 (1.60 g, 3.97 mmol) was dissolved in dry pyridine (30 ml) and allowed to stir at room temperature under argon. To this stirred solution was added TEA (0.51 g, 5 mmol) and isobutyric anhydride (0.79 g, 5 mmol). The reaction mixture was stirred at room temperature for 12 h and evaporated to dryness. The residue was dissolved in EtOAc (150 ml) and washed with 5% NaHCO$_3$ solution (100 ml), water (100 ml) and brine (50 ml). The organic extract was dried and evaporated to dryness. The residue was purified by flash column chromatography over silica gel using CH$_2$Cl$_2$→EtOAc as the eluent. The pure fractions were collected together and evaporated to give 1.6 g (85%) of foam. The pure product was crystallized from acetone/hexane. mp: 165–167° C. $^1$HNMR (CDCl$_3$): 1.16 (d, 6H, IbCH$_3$), 1.42 (s, 9H, Boc), 1.94 (s, 3H, CH$_3$), 2.52 (m, 1H), 3.64 (m, 4H), 3.84 (m, 1H), 4.14 (m, 1H), 5.22 (d, 1H, NH), 7.18 (s, 1H, C$_6$H), 7.48 (t, 2H, Ph), 7.62 (t, 1H, Ph) and 7.98 (d, 2H, Ph).

1-O-Isobutyryl-2-[(β-hydroxyacetyl)amino]-3-[N₃-benzoyl (thyminyl)-L-propanol (24)

1-O-Isobutyryl-2-[(tert-butyloxycarbonyl)amino]-3-[N₃-benzoyl (thyminyl)-L-propanol 23 (1.6 g, 3.38 mmol) was allowed to stir in a mixture of TFA (5 ml) and CH₂Cl₂ (10 ml) at room temperature for 30 min and evaporated to dryness. The residue was dissolved in dry MeOH (10 ml) and evaporated again. The residue that obtained was dried over solid NaOH under vacuum overnight. The dried material was used as such for the next reaction.

To a stirred solution of glycolic acid (0.53 g, 7 mmol) in dry DMF (50 ml) was added 1-hydroxybenzotriazole (0.67 g, 5 mmol) and 1-ethyl-3-(3-dimethylaminopropyl)-carbodiimide hydrochloride (EDC) (1.91 g, 10 mmol). After stirring for 15 min, TEA (1.01 g, 10 mmol) and the above TFA salt in DMF (20 ml) were added at room temperature. The reaction mixture was stirred for 12 h and evaporated to dryness. The residue was partitioned between CH₂Cl₂ (150 ml) and water (100 ml), and extracted in CH₂Cl₂. The organic extract was washed with brine (50 ml), dried and evaporated to dryness. The residue was purified by flash chromatography over silica gel using CH₂Cl₂→acetone as the eluent. The fractions having the required product were collected and evaporated to give 1.35 g (92%) of foam. ¹HNMR (CDCl₃): 1.16 (d, 6H, IbCH₃), 1.94 (s, 3H, CH₃) 2.52 (m, 1H), 3.20 (bs, 1H), 3.80–4.30 (m, 6H), 4.56 (m, 1H), 7.14 (d, 2H, C₆H and NH), 7.50 (t, 2H, Ph), 7.64 (t, 1H, Ph) and 7.94 (d, 2H, Ph).

1-O-Isobutyryl-2-[(β-(4,4'-dimethoxytrityl)-O-acetyl) amino]-3-[N₃-benzoyl(thyminyl)-L-propanol (25)

1-O-Iso-butyryl-2-[(β-hydroxyacetyl)amino]-3-(N₃-benzoyl(thyminyl)-L-propanol 24 (1.2 g, 2.78 mmol) was dissolved in dry pyridine (50 ml) and allowed to stir at room temperature under argon atmosphere. To this stirred solution was added TEA (0.35 g, 3.5 mmol) and 4,4'-dimethoxytrityl chloride (1.18 g, 3.5 mmol). The reaction mixture was stirred at room temperature for 12 h, quenched with MeOH (10 ml) and evaporated to dryness. The residue was dissolved in EtOAc (150 ml), washed with 5% NaHCO₃ solution (100 ml), water (100 ml) and brine (50 ml). The organic extract was dried over Na₂SO₄ and evaporated to dryness. The residue was purified by flash chromatography over silica gel using CH₂Cl₂→EtOAc as the eluent. The pure fractions were pooled and evaporated to give 1.7 g (83%) of pure product. ¹HNMR (CDCl₃): 1.16 (d, 6H, IbCH₃), 1.94 (s, 3H, CH₃), 2.52 (m, 1H), 3.74 (s, 6H, 2.OCH₃), 3.80–4.30 (m, 6H), 4.56 (m, 1H), 6.82 (d, 4H, Ph), 7.14 (d, 2H, C₆H and NH) and 7.26–8.00 (m, 14H, Ph).

2-[(β-(4,4'-Dimethoxytrityl)-O-acetyl)amino]-3-thyminyl-propanol (26)

1-O-Isobutyryl-2-[(β-(4,4'-dimethoxytrityl)-O-acetyl) amino]- 3-[N₃-benzoyl (thyminyl)-L-propanol 25 (1.55 g, 2.05 mmol) was dissolved in MeOH (20 ml) and cooled to 0° C. in an ice bath. To this cold stirred solution was added 2N NaOH (5 ml, 10 mmol) and the stirring continued for 30 min at 0° C. The pH of the solution was adjusted to 7 with acetic acid and evaporated to dryness. The residue was partitioned between water (50 ml) and CH₂Cl₂ (150 ml) and extracted in CH₂Cl₂. The aqueous layer was extracted again with CH₂Cl₂ (50 ml). The combined organic extract was washed with brine (50 ml), dried and evaporated to dryness. The residue was purified by flash column chromatography over silica gel using CH₂Cl₂→acetone as the eluent. Yield: 1.0 g (99%). ¹HNMR (CDCl₃): 1.94 (s, 3H, CH₃), 3.74 (s, 6H, 2.OCH₃), 3.80–4.30 (m, 6H), 4.56 (m, 1H), 6.82 (d, 4H, Ph), 7.14 (d, 2H, C₆H and NH) and 7.26–8.00 (m, 14H, Ph).

2-[(β-(4,4'-Dimethoxytrityl)-O-acetyl)amino]-3-thyminyl-L-propan-1-O-(N,N-diisopropyl)-β-cyanoethylphosphoramidite (27)

2-[(β-(4,4'-Dimethoxytrityl)-O-acetyl)amino]-3-thyminyl-L-propanol 26 (1.00 g, 2.09 mmol) was dried over solid NaOH under vacuum overnight and dissolved in dry CH₂Cl₂ (50 ml). The solution was cooled to 0° C. under argon atmosphere. To this cold stirred solution was added N,N-diisopropylethylamine (0.54 g, 4.2 mmol) followed by 2-cyanoethyl-N,N-diisopropylchlorophosphoramidite (0.73 g, 3.1 mmol). The reaction mixture was stirred at 0° C. for 1 h and at room temperature for 2 h. The reaction was diluted with CH₂Cl₂ (100 ml) and the organic layer was washed with 5% NaHCO₃ solution (100 ml), water (100 ml) and brine (50 ml). The CH₂Cl₂ extract was dried and evaporated to dryness to give an oily residue. The residue was purified by flash chromatography over silica gel using CH₂Cl₂→EtOAc containing 0.1% TEA as the eluent. The pure fractions were pooled together and evaporated to give a foam. The foam was dried over solid NaOH under vacuum overnight. The dried foam was dissolved in dry CH₂Cl₂ (10 ml) and dropped into a stirred solution of dry hexane (800 ml) under argon during 30 min period. After the addition, the precipitate formed was stirred for additional 30 min and filtered, washed with dry hexane (100 ml) and the solid was dried over solid NaOH under vacuum for 4 h. Yield: 1.3 g (82%).

Example 29

(FIG. 29)

N^α-tert-Butyloxycarbonyl-O-benzylhydroxylamine (28)

O-Benzyl hydroxylamine hydrochloride (15.9 g, 100 mmol) was suspended in THF (150 ml) and water (50 ml) mixture. To this stirred mixture was added TEA (15.15 g, 150 mmol) followed by di-tert-butyldicarbonate (23.98 g, 110 mmol). The reaction mixture was stirred at room temperature for 12 h and evaporated to dryness. The residue was partitioned between EtOAc (250 ml) and water (200 ml), and extracted in EtOAc. The EtOAc extract was washed with potassium hydrogen sulfate (100 ml) and brine (100 ml), dried and evaporated to dryness to give 15 g (91%) of clear oil.

1-Chloro-2-(tetrahydropyranyl)oxy-ethane (29)

1-Chloro ethanol (8.06 g, 100 mmol) was dissolved in dry CH₂Cl₂ (100 ml) and cooled to 0° C. in an ice bath under argon. To this stirred solution was added dihydropyran (12.6 g, 150 mmol) followed by pyridinium -p-toluene -4-sulfonate (1.25 g, 5 mmol) and the stirring continued for overnight. The reaction mixture was evaporated to dryness and dissolved in EtOAc (200 ml). The EtOAC extract was washed with 5% NaHCO₃ solution (100 ml), water (100 ml) and brine (100 ml). The organic extract was dried and evaporated to dryness. The crude material was purified by flash chromatography over silica gel using hexane→CH₂Cl₂ as the eluent. The pure fractions collected together and evaporated to give 11 g (67%) of pure product.

N-tert-Butyloxycarbonyl-N-[(tetrahydropyranyl)oxy] ethyl-O-benzylhydroxylamine (30)

To a stirred solution of N-tert-butyloxycarbonyl-O-benzylhydroxylamine 28 (5.79 g, 25.96 mmol) in dry DMF (50 ml) was added NaH (60%, 1.2 g, 30 mmol) slowly during 15 min period under argon atmosphere at 0° C. The reaction was allowed to stir at 0° C. for 30 min and at room temperature for 1 h. 1-Chloro-2-(tetrahydropyranyl)oxy-ethane 29 (4.95 g, 30 mmol) was added and the reaction mixture was heated at 80° C. for 12 h. The reaction was cooled and evaporated to dryness. The residue was suspended in water (50 ml), pH of the solution adjusted to 7 and extracted in EtOAc (150 ml). The EtOAc extract was washed with water and brine, dried and evaporated to dryness. The residue was purified by flash chromatography over silica gel using hexane→$CH_2Cl_2$ as the eluent. The required fractions were collected and evaporated to give 6.0 g (66%) of an oily product. $^1$HNMR ($CDCl_3$): δ1.48 (s, 9H, Boc), 1.49–1.84 (m, 6H, 3.$CH_2$), 3.48–3.70 (m, 4H, 2.$CH_2$), 3.86 (m, 2H, $CH_2$), 4.60 (t, 1H, CH), 4.84 (s, 2H, $CH_2Ph$) and 7.32–7.42 (m, 5H, Ph).

N-tert-Butyloxycarbonyl-N-(2-hydroxy)ethyl]-O-benzylhydroxylamine (31)

A stirred solution of N-tert-Butyloxycarbonyl-N-[(tetrahydropyranyl)oxy]ethyl-O-benzylhydroxylamine 30 (3.51 g, 10 mmol) in THF: water: AcOH (1:1:1, 100 ml) was heated at 70° C. for 3 h. The reaction was cooled to 0° C. and the pH adjusted to 7 with solid $NaHCO_3$. The reaction mixture was extracted with EtOAc (2×75 ml). The combined organic extract was washed with water (100 ml) and brine (100 ml), dried and evaporated to dryness. The residue was purified by flash chromatography over silica gel using $CH_2Cl_2$→EtOAc as the eluent. The pure fractions were pooled and evaporated to give 2.5 g (94%) of foam. $^1$HNMR ($CDCl_3$): δ1.48 (s, 9H, Boc), 3.60 (t, 2H, $CH_2$), 3.74 (m, 2H, $CH_2$), 4.84 (s, 2H, $CH_2Ph$) and 7.32–7.42 (m, 5H, Ph).

N-tert-Butyloxycarbonyl-N-[[(2-isobutyryl)oxy[ethyl[-O-benzylhydroxylamine (32)

To a stirred solution of N-tert-butyloxycarbonyl-N-[(2-hydroxy)ethyl]-O-benzylhydroxylamine 31 (4.2 g, 16.6 mmol) in dry pyridine (50 ml) was added TEA (2.02 g, 20 mmol) followed by isobutyric anhydride (3.16 g, 20 mmol) at room temperature under argon atmosphere. The reaction mixture was stirred at room temperature for 12 h and evaporated to dryness. the residue was dissolved in EtOAc (200 ml), washed with 5% $NaHCO_3$ solution (100 ml), water and brine (50 ml). The organic extract was dried and evaporated to dryness. The residue was purified by flash chromatography over silica gel using $CH_2Cl_2$ as the eluent. The pure fractions collected and evaporated to give 4.5 g (80%) of pure compound. $^1$HNMR ($CDCl_3$): δ1.04 (d, 6H, Ib$CH_3$), 1.48 (s, 9H, Boc), 2.44 (m, 1H, IbCH), 3.60 (t, 2H, $CH_2$), 3.74 (m, 2H, $CH_2$), 4.84 (s, 2H, $CH_2Ph$) and 7.32–7.42 (m, 5H, Ph).

N-(Thyminylacetyl)-N-[[(2-isobutyryl)oxy]ethyl]-O-benzylhydroxylamine (33)

N-tert-Butyloxycarbonyl-N-[[(2-isobutyryl)oxy]ethyl]-O-benzylhydroxylamine 32 (5.0 g, 14.84 mmol) was dissolved in $CH_2Cl_2$ (10 ml) and allowed to stir in TFA (12 ml) for 30 min. The reaction mixture was evaporated to dryness and dissolved in dry methanol (10 ml). It was evaporated again to dryness and dried under vacuum over solid NaOH overnight. The dried material used as such for the next reaction without characterization.

Thymine acetic acid 5 (3.13 g, 17 mmol) was dissolved in dry DMF (75 ml) and cooled to −20° C. under argon. To this cold stirred solution was added N-methylmorpholine (2.02 g, 20 mmol) followed by isobutyl chloroformate (2.72 g, 20 mmol). After 15 min of stirring, a solution of the above TFA salt in dry DMF (50 ml) was neutralized with N-methylmorpholine (2.02 g, 20 mmol) and added immediately into the cold stirred solution of thymine acetic acid at once. The reaction mixture was stirred at −20° C. for 1 h, warmed to room temperature and the stirring continued overnight. The solution was evaporated to dryness and the residue dissolved in $CH_2Cl_2$ (250 ml) and water (100 ml), and extracted in $CH_2Cl_2$. The organic extract was washed with 5% $NaHCO_3$ solution (100 ml), water (100 ml) and brine (50 ml). The $CH_2Cl_2$ extract was dried and evaporated to dryness to give crude product. The crude product was purified by flash chromatography over silica gel using $CH_2Cl_2$→acetone as the eluent. The necessary fractions were collected and evaporated to give 4.0 g (70%) of the pure product. The pure product was crystallized from $CH_2Cl_2$/hexane. mp: 185–188° C. $^1$HNMR ($Me_2SO$-$d_6$): δ1.00 (d, 6H, Ib$CH_3$), 1.74 (s, 3H, $CH_3$), 2.44 (m, 1H, IbCH), 3.92 (m, 2H), 4.18 (t, 2H), 4.68 (bs, 2H), 4.98 (s, 2H), 7.34 (s, 1H, $C_6H$), 7.40–7.50 (m, 5H, Ph) and 11.32 (bs, 1H, NH).

Example 30

(FIG. 30)

(2R,4R)-2-Carbomethoxy-4-hydroxypyrrolidine (35)

In a 250 ml round bottom flask equipped with a magnetic stir bar and a reflex condenser were placed dry methanol (40 ml) and cooled in ice bath under argon atmosphere. To this stirred solution was added acetyl chloride (4.32 g, 55 mmol) followed by cis-4-hydroxy-D-proline 34 (5.00 g, 38.17 mmol). The resulting solution was heated at reflex for 7–8 h and cooled to room temperature. The solution was diluted with ether, and the resulting white solid was collected by suction, was with ether and dried under vacuum over solid NaOH. Yield; 6.9 g (100%) . $^1$HNMR ($CDCl_3$): 2.09 (2 dd, 1H), 2.34 (m, 1H), 3.49–3.73 (m, 3H), 3.79 (s, 3H, $CH_3$), 4.34 (m, 2H)

(2R,4R)-1-(tert-Butyloxycarbonyl)-2-carbomethoxy-4-hydroxypyrrolidine (36)

To a stirred solution of (2R,4R)-2-Carbomethoxy-4-hydroxypyrrolidine 35 (6.9 g, 38.12 mmol) in THF/water (8:2, 150 ml) was added TEA (10.1 g, 100 mmol) followed by di-tert-butyldicarbonate (10.9 g, 50 mmol) at room temperature. The reaction was stirred at room temperature for 6 h and evaporated to dryness. The residue was dissolved in EtOAc (200 ml) and washed with 0.5N potassium hydrogen sulfate (50 ml), water (100 ml) and brine (50 ml). The organic extract was dried over $Na_2SO_4$ and evaporated to dryness to give 7.8 g (84%) of an oily product. The oily product on drying gave colorless solid: mp: 75–77° C. $^1$HNMR ($CDCl_3$): 1.45 (s, 9H, Boc), 2.09 (2 dd, 1H), 2.34 (m, 1H), 3.49–3.73 (m, 3H), 3.79 (s, 3H, $CH_3$), 4.34 (m, 2H).

(2R,4R)-1-(tert-Butyloxycarbonyl)-2-hydroxymethyl-4-hydroxypyrrolidine (37)

(2R,4R)-1-(tert-Butyloxycarbonyl)-2-carbomethoxy-4-hydroxypyrrolidine 36 (7.0 g, 28.6 mmol) was dissolved in dry THF (100 ml) and cooled in ice salt bath under argon atmosphere. To this cold solution was added lithium borohydride (1.88 g, 85.8 mmol) in small portions during 15 min period. After the addition of lithium borohydride, the reaction mixture was allowed to stir at 0° C. for 1 h followed by 15 h at room temperature under argon. The solution was cooled to 0° C. and diluted with water (50 ml) and the pH was adjusted with AcOH to 6. The reaction was evaporated to dryness and dissolved in EtOAc (200 ml), washed with water (100 ml) and brine (100 ml). The EtOAc extract was dried and evaporated to dryness. The residue was purified by flash column chromatography over silica gel using $CH_2Cl_2$→EtOAc as the eluent. The pure fractions were collected and evaporated to dryness to afford 5.00 g (81%) of clear oil. The oil on standing gave colorless solid. mp: 95–97C. $^1$HNMR ($CDCl_3$): 1.45 (s, 9H, Boc), 1.90 (dd, 1H), 2.34 (m, 1H), 3.40 –3.62 (m, 3H), 4.00 (m, 2H), 4.28 (bs, 1H), 4.44 (m, 1H).

(2R,4R)-1-(tert-Butyloxycarbonyl)-2-(4,4'-Dimethoxytrityl) oxymethyl-4-hydroxypyrrolidine (38)

(2R,4R)-1-(tert-Butyloxycarbonyl)-2-hydroxymethyl-4-hydroxypyrrolidine 37 (4.4 g, 20.28 mmol) was dissolved in dry pyridine (50 ml) and allowed to stir under argon atmosphere. To this stirred solution was added TEA (2.53 g, 25 mmol) followed by 4,4'-dimethoxytrityl chloride (7.45 g, 22 mmol). The reaction mixture was stirred at room temperature for 12 h and quenched with MeOH (10 ml). The solution was evaporated to dryness and dissolved in EtOAc (200 ml). The EtOAc layer was washed with 5% $NaHCO_3$ solution (100 ml), water (100 ml) and brine. The organic extract was dried over anhydrous $Na_2SO_4$ and evaporated to dryness. The residue was purified by flash chromatography over silica gel using hexane→EtOAc as the eluent. The required fractions were pooled together and evaporated to give 8.09 g (100%) of an orange foam. $^1$HNMR ($CDCl_3$): 1.45 (s, 9H, Boc), 1.90 (dd, 1H), 2.34 (m, 1H), 3.40–3.62 (m, 3H), 3.74 (s, 6H, 2.$OCH_3$), 4.00 (m, 2H), 4.28 (bs, 1H), 4.44 (m, 1H), 6.82 (d, 4H, Ph), and 7.26–8.00 (m, 9H, Ph).

(2R,4R)-1-(tert-Butyloxycarbonyl)-2-(4,4'-Dimethoxytrityl) oxymethyl-4-[(p-toluenesulfonyl)oxy] pyrrolidine (39)

(2R,4R)-1-(tert-Butyloxycarbonyl)-2-(4,4'-Dimethoxytrityl) oxymethyl-4-hydroxypyrrolidine 38 (8.09 g, 20.27 mmol) was dissolved in dry pyridine/$CH_2Cl_2$ (2:1, 200 ml) and chilled in an ice bath under argon atmosphere. To this cold solution was added TEA (3.03 g, 30 mmol) followed by p-toluenesulphonyl chloride (5.7 g, 30 mmol). The reaction mixture was allowed to stir at 0° C. for 3 h and below 30° C. for 8 h. The reaction mixture was evaporated to dryness, partitioned between EtOAc (200 ml) and 5% $NaHCO_3$ solution (100 ml), and extracted in EtOAc. The EtOAc extract was washed with water (100 ml) and brine (100 ml), dried and evaporated to dryness. The crude product was purified by flash chromatography over silica gel using hexane→EtOAc as the eluent. The pure fractions were pooled together and evaporated to give 12.2 g (89%) of an orange oil. $^1$HNMR ($CDCl_3$): 1.45 (s, 9H, Boc), 1.90 (dd, 1H), 2.34 (m, 1H), 2.40 (s, 3H, $CH_3$), 3.40–3.62 (m, 3H), 3.74 (s, 6H, 2.$OCH_3$), 4.00 (m, 2H), 4.28 (bs, 1H), 4.44 (m, 1H), 6.82 (d, 4H, Ph), and 7.26–8.00 (m, 13H, Ph).

(2R,4S)-1-(tert-Butyloxycarbonyl)-2-(4,4'-Dimethoxytrityl) oxymethyl-4-azido-pyrrolidine (40)

(2R,4R)-1-(tert-Butyloxycarbonyl)-2-(4,4'-Dimethoxytrityl)oxymethyl-4-[(p-toluenesulfonyl)oxy] pyrrolidine 39 (5.1 g, 7.58 mmol) was dissolved in dimethylformamide (50 ml) and diluted with water (5 ml). To this stirred solution was added sodium azide (0.65 g, 10 mmol) and heated at 80° C. for 8 h. It was cooled and evaporated to dryness. The residue was partitioned between $CH_2Cl_2$ (200 ml) and water (100 ml), and extracted in $CH_2Cl_2$. The organic extract was washed with brine (50 ml), dried over $Na_2SO_4$ and evaporated to dryness. The crude product was purified by flash chromatography over silica gel using hexane→EtOAc as the eluent. The pure fractions were pooled together and evaporated to give 3.8 g (92%) of a clear oil. $^1$HNMR ($CDCl_3$): 1.45 (s, 9H, Boc), 1.90 (dd, 1H), 2.34 (m, 1H), 3.40–3.62 (m, 3H), 3.74 (s, 6H, 2.$OCH_3$), 4.00 (m, 2H), 4.28 (bs, 1H), 4.44 (m, 1H), 6.82 (d, 4H, Ph), and 7.26–7.80 (m, 9H, Ph).

(2R,4S)-1-(tert-Butyloxycarbonyl)-2-hydroxymethy-4-amino-pyrrolidine (41)

(2R,4S)-1-(tert-Butyloxycarbonyl)-2-(4,4'-Dimethoxytrityl)oxymethyl-4-azido-pyrrolidine 40 (2.72 g, 5 mmol) in methanol (75 ml) was hydrogenated in the presence of 10% palladium on charcoal (0.3 g) at room temperature and 5 atm pressure. After 12 h, the catalyst was filtered, washed with methanol (20 ml) and the solvent removed under vacuum. Yield 1.0 g (93%). $^1$HNMR ($CDCl_3$): 1.45 (s, 9H, Boc), 1.90 (dd, 1H), 2.34 (m, 1H), 3.40–3.62 (m, 3H), 4.00 (m, 2H), 4.28 (bs, 1H) and 4.44 (m, 1H).

(2R,4S)-1-(tert-Butyloxycarbonyl)-2-hydroxymethyl-4-phthalimido-pyrrolidine (42)

(2R,4S)-1-(tert-Butyloxycarbonyl)-2-hydroxymethyl-4-amino-pyrrolidine 41 (1.00 g, 4.63 mmol) was dissolved in dry methanol (20 ml) and treated with N-ethoxycarbonyl phthalimide (1.09 g, 5 mmol) at room temperature. The reaction mixture was stirred for 6 h and evaporated to dryness the residue was purified by flash chromatography over silica gel using $CH_2Cl_2$→EtOAc as the eluent. The pure fractions were collected and evaporated to give 1.5 g (94%) of pure compound as foam. $^1$HNMR ($CDCl_3$): 1.45 (s, 9H, Boc), 1.90 (dd, 1H), 2.34 (m, 1H), 3.40–3.62 (m, 3H), 4.00 (m, 2H), 4.28 (bs, 1H), 4.44 (m, 1H) and 7.3–7.6 (m, 4H, Ph).

(2R,4S)-1-(tert-Butyloxycarbonyl)-2-[$N_3$-benzoyl (thymin-1-yl)] methyl-4-phthalimido-pyrrolidine (43)

To a stirred solution of $N_3$-benzoylthymine 20 (1.15 g, 5 mmol) in dry THF (70 ml) under argon was added triphenyl phosphine (2.62 g, 10 mmol) and (2R,4S)-1-(tert-Butyloxycarbonyl)-2-hydroxymethyl-4-phthalimido-pyrrolidine (1.4 g, 4.05 mmol) at room temperature. After 15 min, diethylazodicarboxylate (1.74 g, 10 mmol) was added slowly during 10 min period. The reaction mixture was covered with aluminum foil and allowed to stir at room temperature under argon for 24 h. The solvent was evaporated to dryness and the residue dissolved in EtOAc (150 ml). The organic extract was washed with 5% $NaHCO_3$ solution (100 ml), water (100 ml) and brine (100 ml), and dried over anhydrous $Na_2SO_4$. The dried EtOAc extract was evaporated to dryness to give an orange oil. The crude product was purified by flash chromatography over silica gel using hexane→EtOAc as the eluent. The fraction having the required product was pooled and evaporated to give a pale pink oil. Yield: 2.0 g (89%). $^1$HNMR ($CDCl_3$): 1.41 (s, 9H, Boc), 1.72 (s, 3H, $CH_3$), 1.90 (dd, 1H), 2.34 (m, 1H), 3.40–3.62 (m, 3H), 4.00 (m, 2H), 4.28 (bs, 1H), 4.44 (m, 1H), 7.06 (s, 1H, $C_6H$) and 7.20–7.60 (m, 9H, Ph).

Example 31

Synthesis of Oligonucleotides

Oligonucleotides containing modified amino acid nucleic acid backbones were synthesized on an automated DNA synthesizer (Applied Biosystems model 394) using standard phosphoramidite chemistry. β-Cyanoethyl phosphoramidities, synthesis reagents and CPG polystyrene colums were purchased from Applied Biosystems (Foster City, Calif.). For phosphorothioate oligonucleotides, the standard oxidation bottle was replaced with tetraethylthiuram disulfide/acetonitrile, and the standard ABI phosphorothiate program was used for the stepwise thiation of the phosphate linkages. After cleavage from the controlled pore glass column, the protecting groups were removed by treating the oligonucleotides with concentrated ammonium hydroxide at 55° C. for 8 hrs. The oligonucleotides (DMT-on) were purified by HPLC using a reverse phase semiprep $C_8$ column (ABI) with a linear gradient of 5% acetonitrile in 0.1M triethylammonium acetate (buffer A) and acetonitrile (buffer B). The DMT protecting group was cleaved by treatment with 80% acetic acid and the product was ethanol precipitated. The purity of the products were checked by HPLC using an analytical $C_{18}$ column (Beckman). The amino acid nucleic acid monomers were incorporated at the 3'-end, 5'-end and in the middle of a DNA sequence with a coupling efficiency of 100%. A homo polymer containing 16 amino acid modified thymine was also prepared with out any problem.

Example 32

Hybridization analysis

The ability of the amino acid modified oligonucleotides of the invention to hybridize to their complementary RNA and DNA sequences is determined by thermal melting analysis. The RNA complement is synthesized by Genset corporation (La Jolla, Calif.) and purified by denaturing urea PAGE. Natural antisense oligonucleotides or those containing functionalized at specific locations are added to either the RNA or DNA complement at stoichiometric concentrations to form hybrid duplexes. The absorbance (260 nm) hyperchromicity dependence on temperature upon duplex to random coil transition is monitored using Varian Cary 1E UV-Visible spectrophotometer. The measurements are performed in a buffer of 10 mM Na-phosphate, pH 7.4, 0.1 mM EDTA, and NaCl to yield an ionic strength of either 0.1N or 1.0M. Data are analysed by a graphic representation of 1/Tm vs ln[Ct], where [Ct] is the total oligonucleotide concentration. From this analysis the thermodynamic parameters are determined. Based on the information gained concerning the stability of the duplex or hetero-duplex formed, the placement of modified pyrimidine into oligonucleotides is assessed for its effects on helix stability. Modifications that drastically alter the stability of the hybrid exhibit reductions or enhancements in the free energy (delta G) and decisions concerning their usefulness in antisense oligonucleotides are made.

Hybridization studies were conducted with oligonucleotides containing amino acid nucleic acid backbone at 3'-end as well as at the 5'-end. Preliminary studies showed that the modified oligonucleotides form duplex with their complementary RNA and DNA sequences like unmodified oligonucleotides.

Example 33

Nuclease Resistance

Natural, phosphorothioate and modified oligonucleotides of the invention are assessed for their resistance to serum nucleases by incubation of the oligonucleotides in media containing various concentrations of fetal calf serum or adult human serum. Labeled oligonucleotides are incubated for various times, treated with protease K and then analyzed by gel electrophoresis on 20% polyacrylamide-urea denaturing gels and subsequent autoradiography or phosphor-imaging. Autoradiograms are quantitated by laser densitometry. Based upon the location of the modifications and the known length of the oligonucleotide it is possible to determine the effect of the particular modification on nuclease degradation. For the cytoplasmic nucleases, a HL60 cell line is used. A post-mitochondrial supernatant is prepared by differential centrifugation and the labeled oligonucleotides are incubated in this supernatant for various times. Following the incubation, oligonucleotides are assessed for degradation as outlined above for serum nucleolytic degradation. Autoradiography results are quantitated for comparison of the unmodified i.e., phosphorothioate and the modified oligonucleotides.

Preliminary studies on the amino acid modified oligonucleotides showed that they are resistant to Snake Venom Phosphodiesterase.

Incorporation by Reference

All patents, patents applications, and publications cited are incorporated herein by reference.

Equivalents

The foregoing written specification is considered to be sufficient to enable one skilled in the art to practice the invention. Indeed, various modifications of the above-described makes for carrying out the invention which are obvious to those skilled in the field of molecular biology, organic chemistry, or related fields are intended to be within the scope of the following claims.

What is claimed is:

1. A monomer of formula 1 in any of Groups I–V, which, when polymerized, adopts a rigid conformation via intramolecular Hydrogen bonding, and thereby mimics ribose puckering:

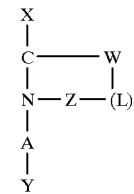

Formula 1

Group I, where:
- X is $CHR_2OH$ where $R_2$ is H, lower alkyl amine or lower alkyl imidazole;
- Y is Base-$(CH_2)n$-, where Base is a non-halogenated purine, and n is 1 to 7 C atoms;
- A is carbonyl;
- Z is H or $OR_3$, where $R_3$ is H, lower alkyl, lower alkyl amine or lower alkyl imidazole;
- W is $CHR_4OH$, where $R_4$ is H or lower alkyl amine or lower alkyl imidazole;
- N is N (nitrogen); and
- L is nothing;

Group II, where:
- X is Base-$(CH_2)n$-, where Base is a non-halogenated purine, and n is 1 to 7 C atoms;
- Y is $CHR_2OH$ where $R_2$ is H, lower alkyl amine or lower alkyl imidazole;
- A is carbonyl or $CH_2$;
- Z is H or $OR_3$, where $R_3$ is H, lower alkyl, lower alkyl amine or lower alkyl imidazole;
- W is $CHR_4OH$, where $R_4$ is H or lower alkyl amine or lower alkyl imidazole;
- N is N (nitrogen); and
- L is nothing;

Group III, where:
- X is $CHR_2OH$ where $R_2$ is H, lower alkyl amine or lower alkyl imidazole;
- Y is Base-(CH2)n-, where Base is a non-halogenated purine, and n is 1 to 7 C atoms;
- A is $CH_2$;
- Z is OH or $OR_3$ and $R_3$ is H, lower alkyl, lower alkyl amine or lower alkyl imidazole;
- W is $CHR_4OH$, where $R_4$ is H or lower alkyl amine or lower alkyl imidazole;
- N is N (nitrogen); and
- L is nothing;

Group IV, where:
- X is Base-$(CH_2)n$-, where Base is a non-halogenated purine, and n is 1 to 7 C atoms;
- Y is COOH or $CHR_2OH$ where $R_2$ is H, lower alkyl amine or lower alkyl imidazole;
- A is carbonyl or $CH_2$;
- Z is $CH_2$;

W is $CH_2$;

N is N (nitrogen); and

L is $CHNHR_5$ where $R_5$ is H, OH or $OR_3$, and $R_3$ is H, lower alkyl, lower alkyl amine or lower alkyl imidazole; and Group V, where:

X is $CH_2OH$, $CH_2NH_2$, $CONH_2$ or COOH;

Y is nothing;

Z is $CH_2$ or $CHO-L_1-B$;

W is O, S or $CH_2$;

N is CH; and

L and A are independently COOH, CHCOOH, $CHCH_2COOH$, $NH_2$, $CHNH_2$, $L_1-NH-L_2-B$ or $CH-L_1-NH-L_2-B$; where B is H or a purine, and $L_1$ and $L_2$ are independently $(CH_2)_n$ or $(CH_2)_nCO$, where n=–0, 1, 2 or 3.

2. An oligomer comprising at two adjacent monomers according to claim 1 such that internucleotide linkages occur between W and X in Group I, W and Y in Group II, W and Z in Group III, L and Y in Group IV, and L and A in Group V, wherein such oligonucleotide selectively forms a fully complementary duplex with a nucleotide.

3. The oligonucleotide according to claim 2, wherein the internucleotide linkage comprises a phosphodiester.

4. The oligonucleotide according to claim 2, wherein the internucleotide linkage comprises a phosphorothioate.

5. The oligonucleotide according to claim 2, wherein the internucleotide linkage comprises a phosphoramidate.

6. The oligonucleotide according to claim 2, wherein the internucleotide linkage comprises a hydroxamate.

7. The oligonucleotide according to claim 2, distinguishable into a plurality of monomers wherein at least one of the monomers comprises a 2'-deoxyribose nucleoside, and further comprising at least two different internucleotide linkages from the group consisting of phosphodiester, phosphorothioate, phosphoramidate and hydroxamate.

8. The oligonucleotide according to claim 2, having a 2'-deoxyribose nucleoside pentafuranosyl ring wherein the ring oxygen is replaced with one of S, $CH_2$ or $NR_6$, where $R_6$ is acetyl, lower alkyl, carbonyl, carbonyl lower alkyl amine, or carbonyl lower alkyl imidazole.

9. The oligonucleotide of claim 2, wherein at least one monomer satisfies Group V of claim 1, and a maximum of fifty monomers are selected from 2'-deoxyribonucleoside, ribonuceloside and 2'-methylribonucleoside.

* * * * *